(12) United States Patent
Stout et al.

(10) Patent No.: US 11,098,097 B2
(45) Date of Patent: *Aug. 24, 2021

(54) RECOMBINANT FILAGGRIN POLYPEPTIDES FOR CELL IMPORTATION

(71) Applicant: Research Development Foundation, Carson City, NV (US)

(72) Inventors: J. Timothy Stout, Portland, OR (US); Binoy Appukuttan, Portland, OR (US); Trevor McFarland, Portland, OR (US)

(73) Assignee: Research Development Foundation, Carson City, NV (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/242,487

(22) Filed: Jan. 8, 2019

(65) Prior Publication Data

US 2019/0127430 A1   May 2, 2019

Related U.S. Application Data

(63) Continuation of application No. 13/511,267, filed as application No. PCT/US2010/057592 on Nov. 22, 2010, now Pat. No. 10,336,797.

(60) Provisional application No. 61/263,604, filed on Nov. 23, 2009.

(51) Int. Cl.
| | |
|---|---|
| *C07K 14/47* | (2006.01) |
| *A61K 8/64* | (2006.01) |
| *A61Q 19/00* | (2006.01) |
| *A61K 38/00* | (2006.01) |
| *A61Q 17/04* | (2006.01) |
| *A61Q 19/04* | (2006.01) |

(52) U.S. Cl.
CPC ............ *C07K 14/4713* (2013.01); *A61K 8/64* (2013.01); *A61Q 19/005* (2013.01); *A61Q 19/008* (2013.01); *A61K 38/00* (2013.01); *A61Q 17/04* (2013.01); *A61Q 19/00* (2013.01); *A61Q 19/04* (2013.01)

(58) Field of Classification Search
None
See application file for complete search history.

(56) References Cited

U.S. PATENT DOCUMENTS

| | | | | |
|---|---|---|---|---|
| 3,463,302 | A * | 8/1969 | Preston ................... | B65D 83/00 206/361 |
| 8,338,386 | B2 | 12/2012 | McLean et al. | |
| 2003/0032593 | A1 * | 2/2003 | Wender .................. | A61K 47/64 514/1.2 |
| 2003/0072795 | A1 | 4/2003 | Steinert et al. | |
| 2003/0124159 | A1 | 7/2003 | Jenkins et al. | |
| 2003/0124553 | A1 | 7/2003 | Ginger | |
| 2004/0106120 | A1 | 6/2004 | Tazi-Ahnini et al. | |
| 2004/0186045 | A1 | 9/2004 | Rothbard et al. | |
| 2005/0053637 | A1 | 3/2005 | Ma'Or et al. | |
| 2009/0176810 | A1 | 7/2009 | Shin et al. | |
| 2010/0017896 | A1 | 1/2010 | McLean et al. | |
| 2010/0210578 | A1 | 8/2010 | McLean et al. | |
| 2012/0010226 | A1 | 1/2012 | Shin et al. | |

FOREIGN PATENT DOCUMENTS

| | | |
|---|---|---|
| WO | WO 1994/018945 | 9/1994 |
| WO | WO 2003/078470 | 9/2003 |
| WO | WO2007/063024 | * 6/2007 |
| WO | WO 2007/068946 | 6/2007 |
| WO | WO 2011/038210 | 3/2011 |
| WO | WO 2012/077037 | 6/2012 |

OTHER PUBLICATIONS

Aberg et al., "Involucrin expression is decreased in Hailey-Hailey keratinocytes owing to increased involucrin mRNA degradation," *J. Invest. Derm.*, 127:1973-1979, 2007.
Angelova-Fischer, et al., "Distinct barrier integrity phenotypes in filaggrin-related atopic eczema following sequential tape stripping and lipid profiling," *Exp. Dermatol.*, 20:351-6, 2011.
Barker, et al., "Null mutations in the filaggrin gene (FLG) determine major susceptibility to early-onset atopic dermatitis that persists into adulthood," *J. Invest. Dermatol.*, 127:564-7, 2007.
Brown, et al., "Filaggrin null mutations and childhood atopic eczema: a population-based case-control study," *J. Allergy Clin. Immunol.*, 121:940-6, 2008.
Brown, et al., "Loss-of-function variants in the filaggrin gene are a significant risk factor for peanut allergy," *J. Allergy Clin. Immunol.*, 127:661-7, 2011.
Candi, et al., "The cornified envelope: a model of cell death in the skin," *Nat. Rev. Mol. Cell. Biol.*, 6:328-40, 2005.
Chen et al., "Topical delivery of hyaluronic acid into skin using SPACE-peptide carriers," *Journal of Controlled Release*, 173:67-74, 2014.
Chen, et al., "Wide spectrum of filaggrin-null mutations in atopic dermatitis highlights differences between Singaporean Chinese and European populations," *Br. J. Dermatol.*, 165:106-14, 2011.
Denecker, et al., "Caspase-14 protects against epidermal UVB photodamage and water loss," *Nat. Cell. Biol.*, 9:666-74, 2007.
Desai et al., "$^{31}$P solid-state NMR based monitoring of permeation of cell penetrating peptides into skin," *European Journal of Pharmaceutics and Biopharmaceutics*, [article in press], http://dx.doi.org/10.1016/j.ejpb.2013.05.003, 2013.

(Continued)

*Primary Examiner* — James H Alstrum-Acevedo
*Assistant Examiner* — Tara L Martinez
(74) *Attorney, Agent, or Firm* — Parker Highlander PLLC

(57) ABSTRACT

Disclosed are recombinant polypeptides that include (a) a filaggrin amino acid sequence and (b) a cell importation signal sequence that includes a motif of two to fifteen amino acids, wherein the motif includes at least one arginine residue and at least one methionine residue. Also disclosed are nucleic acids encoding the recombinant polypeptides of the present invention, and compositions that include the recombinant polypeptides and nucleic acids of the present invention. Methods of treating or preventing a skin disease or skin disorder using the compositions of the present invention are also included, as well as kits that include a sealed containing that includes a recombinant polypeptide of the present invention.

20 Claims, No Drawings
Specification includes a Sequence Listing.

(56) References Cited

OTHER PUBLICATIONS

European Extended Search Report for European Application 10832312.2 dated Aug. 7, 2013.
Fleckman, et al., "Keratinocytes cultured from subjects with ichthyosis vulgaris are phenotypically abnormal," *J. Invest. Dermatol.*, 88:640-5, 1987.
Gan, et al., "Organization, structure, and polymorphisms of the human profilaggrin gene," *Biochemistry*, 29:9432-40, 1990.
Hansmann et al., "Murine filaggrin-2 is involved in epithelial barrier function and down-regulated in metabolically induced skin barrier dysfunction," *Exp. Dermatology*, 21:271-276, 2012.
Hedayati, et al., "Specific IgE against Alternaria alternata in atopic dermatitis and asthma patients," *Eur. Rev. Med. Pharmacol. Sci.*, 13:187-91, 2009.
Hogan, et al., "Skin barrier function and its importance at the start of the atopic march," *J. Allergy*, pp. 1-7, 2012.
Hoste et al., "Caspase-14 is required for filaggrin degradation to natural moisturizing factors in the skin," *Journal of Investigative Dermatology*, 131:2233-2241, 2011.
Hou et al., "Transdermal delivery of proteins mediated by non-covalently associated arginine-rich intracellular delivery peptides," *Experimental Dermatology*, 16:999-1006, 2007.
International Search Report and Written Opinion, issued in PCT/US2010/057592, dated Aug. 2, 2011.
Irvine, "Fleshing out filaggrin phenotypes," *J. Invest. Dermatol.*, 127:504-7, 2007.
Irvine, A . . . , "Crossing barriers; restoring barriers? Filaggrin protein replacement takes a bow," *Journal of Investigative Dermatology*, 134:313-314, 2014.
Ishida-Yamamoto, "Loricrin keratoderma: a novel disease entity characterized by nuclear accumulation of mutant loricrin," *J. Dermatol. Sci*, 31:3-8, 2003.
Kanda et al., "Characterization of canine filaggrin: gene structure and protein expression in dog skin," *Vet. Dermatol.*, 24:25-e7, 2013.
Keller et al., "Relationships between Cargo, Cell Penetrating Peptides and Cell Type for Uptake of Non-Covalent Complexes into Live Cells," *Pharmaceuticals*, 6:184-203, 2013.
Kezic, et al., "Loss-of-function mutations in the filaggrin gene lead to reduced level of natural moisturizing factor in the stratum corneum," *J. Invest. Dermatol.*, 128:2117-9, 2008.
Kim et al., "Enhancement of keratinocyte differentiation by rose absolute oil." *Ann Dermatol.*, 22:255-61, 2010.
Kim et al., "TNF-α downregulates filaggrin and loricrin through c-Jun N-terminal kinase role for TNF-α antagonists to improve skin barrier," *J Invest Dermatol.*, 131:1272-9, 2011.
Lingren et al., "Cell-penetrating peptides," *TiPS*, 21:99-103, 2000.
Liou et al., "Protein transduction in human cells is enhanced by cell-penetrating peptides fused with an endosomolytic HA2 sequence," *Peptides*, 37:273-284, 2012.
Lucas Meyer Cosmetics, "Phospholipid Based Emulsifiers for Skin Care," Jul. 2008.
Mae and Langel, "Cell-penetrating peptides as vectors for peptide, protein and oligonucleotide delivery," *Current Opinion in Pharmacology*, 6(5):509-514, 2006.
Manabe, et al., "Interaction of filaggrin differentiation with keratin filaments during advanced stages of normal human epidermal and in ichthyosis vulgaris," *Differentiation*, 48:43-50, 1991.
Marsella and Samuelson, "Unravelling the skin barrier: a new paradigm for atopic dermatitis and house dust mites," *Vet. Detmatol.*, 20:533-40, 2009.
McGrath, "Filaggrin and the great epidermal barrier grief," *Aus. J. Derm.*, 49:67-74, 2008.
McLean, "The allergy gene: how a mutation in a skin protein revealed a link between eczema and asthma," *F1000 Med. Rep.*, 3:2, 2011.
Nasrollahi et al., "Cell-penetrating peptides as a novel transdermal drug delivery system," *Chem. Biol. Drug Des.*, 80:639-646, 2012.
Nomura, et al., "Unique mutations in the filaggrin gene in Japanese patients with ichthyosis vulgaris and atopic dermatitis," *J. Allergy Clin. Immunol.*, 119:434-40, 2007.
O'Regan, et al., "Raman profiles of the stratum corneum define 3 filaggrin genotype-determined atopic dermatitis endophenotypes," *J. Allergy Clin. Immunol.*, 126:574-80, 2010.
Office Communication issued in Australian Patent Application No. 2010321784, dated Nov. 27, 2013.
Office Communication issued in Australian Patent Application No. 2014203006, dated Jun. 23, 2015.
Office Communication issued in Australian Patent Application No. 2014203006, dated Sep. 15, 2015.
Office Communication issued in Australian Patent Application No. 2014203006, dated Jan. 18, 2016.
Office Communication issued in Canadian Patent Application No. 2,781,537, dated Nov. 3, 2016.
Office Communication issued in Canadian Patent Application No. 2,781,537, dated Dec. 27, 2017.
Office Communication issued in Canadian Patent Application No. 2,781,537, dated Jan. 7, 2019.
Office Communication issued in European Patent Application No. 10832312.2, dated Apr. 14, 2014.
Office Communication issued in European Patent Application No. 10832312.2, dated Sep. 14, 2015.
Office Communication issued in U.S. Appl. No. 13/511,267, dated Oct. 26, 2018.
Office Communication issued in U.S. Appl. No. 13/511,267, dated Nov. 17, 2016.
Office Communication issued in U.S. Appl. No. 13/511,267, dated Feb. 1, 2016.
Office Communication issued in U.S. Appl. No. 13/511,267, dated Sep. 17, 2015.
Office Communication issued in U.S. Appl. No. 13/511,267, dated Mar. 5, 2015.
Office Communication issued in U.S. Appl. No. 13/511,267, dated Jan. 13, 2015.
Office Communication issued in U.S. Appl. No. 13/511,267, dated Jul. 29, 2014.
Office Communication issued in U.S. Appl. No. 13/511,267, dated Nov. 15, 2013.
Office Communication issued in U.S. Appl. No. 13/511,267, dated Aug. 2, 2013.
Pena-Penabad et al., "Altered expression of immunoreactive involucrin in lamellar ichthyosis," *Eur. J. of Derm.*, 9:197-201, 1999.
Presland, et al., "Characterization of the human epidermal profilaggrin gene. Genomic organization and identification of an S-100-like calcium binding domain at the amino terminus," *J. Biol. Chem.*, 267:23772-81, 1992.
Presland, et al., "Loss of normal profilaggrin and filaggrin in flaky tail (ft/ft) mice: an animal model for the filaggrin-deficient skin disease ichthyosis vulgaris," *J. Invest. Dermatol.*, 115:1072-81, 2000.
Rawlings and Harding, "Loss of normal profilaggrin and filaggrin in flaky tail (ft/ft) mice: an animal mode for the filaggrin-deficient skin disease ichthyosis vulgaris," *Dermatol. Ther.*, 17 Suppl. 1:43-8, 2004.
Rothnagel and Steinert, "The structure of the gene for mouse filaggrin and a comparison of the repeating units," *J. Biol. Chem.*, 265:1862-5, 1990.
Ruether, et al., "Filaggrin loss-of-function variant contributes to atopic dermatitis risk in the population of Northern Germany," *Br. J. Dermatol.*, 155:1093-4, 2006.
Sandilands, et al., "Filaggrin in the frontline: role in skin barrier function and disease," *J. Cell Sci.*, 122:1285-94, 2009.
Smith, et al., "Loss-of-function mutations in the gene encoding filaggrin cause ichthyosis vulgaris," *Nat. Genet.*, 38:337-42, 2006.
Spergel, "From atopic dermatitis to asthma: the atopic march," *Ann. Allergy Asthma. Immunol.*, 105:99-106, 2010.
Stout et al., "Recombinant filaggrin is internalized and processed to correct filaggrin deficiency," *Journal of Investigative Dermatology*, doi:10.1038/jid.2013.284, E-published Jun. 21, 2013.

(56) References Cited

OTHER PUBLICATIONS

Sybert, et al., "Ichthyosis vulgaris: identification of a defect in synthesis of filaggrin correlated with an absence of keratohyalin granules," *J. Invest. Dermatol.*, 94:191-4, 1985.

Tünnemann et al., "Cargo-dependent mode of uptake and bioavailability of TAT-containing proteins and peptides in living cells," *FASEB J.*, 20:1775-1784, 2006.

Wallbrecher et al., "The stoichiometry of peptide-heparan sulfate binding as a determinant of uptake efficiency of cell-penetrating peptides," *Cellular and Molecular Life Sciences*, published online doi:10.1007/s00018-013-1517-8, Nov. 24, 2013.

Wang et al., "Recent progress of cell-penetrating peptides as new carriers for intracellular cargo delivery," *Journal of Controlled Release*, 174:126-136, 2014.

Weidinger, et al., "Loss-of-function variations within the filaggrin gene predispose for atopic dermatitis with allergic sensitizations," *J. Allergy Clin. Immunol.*, 118:214-9, 2006.

Wells and Kerr, "Clinical features of autosomal dominant and sex-linked ichthyosis in an English population," *Br. Med. J.*, 1:947-50, 1966.

Zorko and Langel, "Cell-penetrating peptides: mechanism and kinetics of cargo delivery," *Advanced Drug Delivery Reviews*, 57(4):529-545, 2005.

\* cited by examiner

RECOMBINANT FILAGGRIN POLYPEPTIDES FOR CELL IMPORTATION

The present application is a continuation of U.S. application Ser. No. 13/511,267, filed May 22, 2012, which is a national phase application under 35 U.S.C. § 371 of International Application No. PCT/US2010/057592, filed Nov. 22, 2010, which claims benefit of priority to U.S. Provisional Application Ser. No. 61/263,604, filed Nov. 23, 2009, the entire contents of each of which are hereby incorporated by reference.

BACKGROUND OF THE INVENTION

1. Field of the Invention

The present invention relates generally to the fields of protein chemistry, intracellular protein transport, skin care, and the treatment and prevention of skin disease. More particularly, it concerns methods, compositions, and kits employing recombinant filaggrin polypeptides that include an attached cell importation signal sequence, or nucleic acids encoding a filaggrin polypeptide with an attached cell importation signal sequence.

2. Description of Related Art

Skin diseases are a common cause of morbidity in the U.S. For example, ichthyosis vulgaris and atopic dermatitis have a combined incidence of 1 in 250. They are the most common disorders of keratinization. These diseases are characterized by hyperlinearity, keratosis pilaris and itchy, scaly, often inflamed skin. Ichthyosis vulgaris and atopic dermatitis are also associated with one of the most common single-gene disorders in humans, a disorder of the filaggren (FLG) gene.

FLG is a 3-exon gene located in the Epidermal Differentiation Complex (EDC) on chromosome 1q21. In healthy patients, the FLG gene codes for the (pro) filaggrin protein, a protein essential for proper keratinization and squamification of epithelial cells, formation of epidermal barrier, and hydration. In almost fifty percent of patients with these diseases, however, one of two nonsense mutations have been present in exon 3 (R501X and 2282de14) (Hoffjan, 2007). These mutations disable the profilaggrin polyprotein from being proteolytically cleaved to the functioning FLG protein. FLG protein is expressed in the cytoplasm of epithelial cells; it is absent from the nucleus in vivo. A correlation between the number of filaggrin repeats and the predisposition to dry skin has also been shown (see U.S. Patent App. Publ. No. 2003/0124553). Administration of a polypeptide comprising a profilaggrin has been proposed as a treatment for dry skin (U.S. Patent Appl. Pub. No. 2003/0124553).

Despite the information available concerning FLG and its role in skin disease, there is a need for more effective methods of treating diseases or disorders of the skin.

SUMMARY OF THE INVENTION

The present invention is in part based on the finding that the uptake of a filaggrin polypeptide into a cell can be surprisingly and effectively enhanced by attaching a cell importation signal sequence to the filaggrin polypeptide. The cell importation sequence, for example, may be a sequence comprising a motif of two to fifteen amino acids, wherein the motif includes at least one arginine residue and at least one methionine residue. Compositions that include the polypeptides of the present invention have improved therapeutic efficacy compared to polypeptides that do not include the cell importation signal sequence.

Some embodiments of the present invention include a recombinant polypeptide that includes (a) a filaggrin amino acid sequence; and (b) a cell importation signal sequence including a motif of two to fifteen amino acids, wherein the motif includes at least one arginine residue and at least one methionine residue. The filaggrin amino acid sequence may include any number of amino acids of a native filaggrin protein. In some embodiments, for example, the filaggrin amino acid sequence includes 20, 30, 40, 50, 60, 70, 80, 90, 100, 120, 130, 150, 150, 160, 170, 180, 190, 200, 210, 220, 230, 240, 250, 260, 270, 280, 290, 300, 310, 320, 330, 340 or more consecutive amino acids of any of the amino acid sequences set forth in Table 2 below, or any range of amino acids derivable therein, so long as the filaggrin amino acid sequence when conjugated to a cell importation signal sequence retains at least some of the function of a native filaggrin amino acid sequence conjugated to the same cell importation sequence. Non-limiting functions of a native filaggrin amino acid sequence include reduction in peeling of skin, reduction of skin redness, reduction of itching of skin, reduction of crusting of skin, reduction in dryness of skin, reduction in scaling of skin, reduction of skin inflammation, reducing of skin cracking, reduction of blistering of skin, reduction of scarring of skin, reduction of oozing of skin, and reduction of bleeding of skin.

In some embodiments, the filaggrin amino acid sequence includes any of the amino acid sequences set forth in Table 2. In particular embodiments, the filaggrin amino acid sequence includes SEQ ID NO:1.

In some embodiments, the filaggrin amino acid sequence has at least about 80%, 81%, 82%, 83, 84%, 85%, 86%, 87%, 88%, 89%, 90%, 91%, 92%, 93%, 94%, 95%, 96%, 97%, 98%, 99% or 100% sequence identity with a native filaggrin amino acid sequence, or any range of percent sequence identify derivable therein. Examples of filaggrin sequences are set forth in Table 2 below. In particular embodiments, the filaggrin amino acid sequence has at least about 80%, 81%, 82%, 83, 84%, 85%, 86%, 87%, 88%, 89%, 90%, 91%, 92%, 93%, 94%, 95%, 96%, 97%, 98%, 99% or 100% sequence identity with SEQ ID NO:1. "Sequence identity" is defined as the percentage of amino acid residues in a candidate sequence that are identical with the amino acid residues at corresponding positions in a native polypeptide sequence, after aligning the sequences and introducing gaps if necessary, to achieve the maximum percent sequence identity, and not considering any conservative substitutions as part of the sequence identity. The % sequence identity values may be generated by the NCBI BLAST2.0 software as defined by Altschul et al. (1997). The parameters are set to default values, with the exception of Penalty for mismatch, which is set to −1.

Regarding the cell importation sequence, in some embodiments, the amino acid sequence includes an arginine residue covalently attached to a methionine residue. In some embodiments, the arginine residue and the methionine residue are separated by 1, 2, 3, 4, 5, 6, 7, or 8 intervening amino acid residues. In a particular embodiment, the cell importation sequence comprises SEQ ID NO:23.

In some embodiments, the polypeptide includes a linker between the filaggrin amino acid sequence and the cell importation amino acid sequence. The linker may be any linker known to those of ordinary skill in the art. Some non-limiting examples of linkers are discussed in the specification below.

In some embodiments, the polypeptide includes SEQ ID NO:21 or SEQ ID NO:22. In a specific embodiment, the polypeptide is SEQ ID NO:21.

The polypeptide may be further defined as a fusion protein of the filaggrin amino acid sequence and the cell importation amino acid sequence. The filaggrin amino acid sequence may be attached to the N-terminus of the cell importation signal sequence, or it may be attached to the C-terminus of the cell importation signal sequence.

Other embodiments of the present invention include a nucleic acid that includes a nucleic acid sequence that encodes a chimeric polypeptide as set forth above. Further embodiments include a nucleic acid that encodes a filaggrin amino acid sequence. The filaggrin amino acid sequence is any filaggrin amino acid sequence as set forth herein. In some embodiments, the nucleic acid is comprised in a viral vector. Non-limiting examples of viral vectors include lentiviral vectors, adeno-associated viral vectors, and adenoviral vectors.

Other embodiments of the present invention concern a skin-care composition that includes an effective amount of a polypeptide that includes a filaggrin amino acid sequence and a cell importation signal sequence, or a nucleic acid encoding a polypeptide of the present invention as set forth above. The polypeptide may be any of the aforementioned polypeptide chimeras. The nucleic acid may be any of the aforementioned nucleic acids.

In some embodiments, the composition further includes a lipid component. The lipid component may have a net neutral charge. It may be include only neutral lipids, or it may optionally include cationic and anionic lipids such that the net charge of the lipids in the lipid component is neutral.

The lipid component may include a neutral lipid. For example, the neutral lipid may be a neutral phospholipid. Non-limiting examples of neutral phospholipids include phosphatidylcholine or phosphatidylethanolamine. Other examples of neutral phospholipids include 1,2-dioleoyl-sn-glycero-3-phosphatidylcholine (DOPC), egg phosphatidylcholine ("EPC"), dilauryloylphosphatidylcholine ("DLPC"), dimyristoylphosphatidylcholine ("DMPC"), dipalmitoylphosphatidylcholine ("DPPC"), distearoylphosphatidylcholine ("DSPC"), 1-myristoyl-2-palmitoyl phosphatidylcholine ("MPPC"), 1-palmitoyl-2-myristoyl phosphatidylcholine ("PMPC"), 1-palmitoyl-2-stearoyl phosphatidylcholine ("PSPC"), 1-stearoyl-2-palmitoyl phosphatidylcholine ("SPPC"), dimyristyl phosphatidylcholine ("DMPC"), 1,2-distearoyl-sn-glycero-3-phosphocholine ("DAPC"), 1,2-diarachidoyl-sn-glycero-3-phosphocholine ("DBPC"), 1,2-dieicosenoyl-sn-glycero-3-phosphocholine ("DEPC"), palmitoyloeoyl phosphatidylcholine ("POPC"), lysophosphatidylcholine, dilinoleoylphosphatidylcholine distearoylphophatidylethanolamine ("DSPE"), dimyristoyl phosphatidylethanolamine ("DMPE"), dipalmitoyl phosphatidylethanolamine ("DPPE"), palmitoyloeoyl phosphatidylethanolamine ("POPE"), and lysophosphatidylethanolamine.

The lipid component may include a negatively charged lipid. For example, the negatively charged lipid may be a negatively charged phospholipid. Non-limiting examples of negatively charged phospholipids include phosphatidylserine and phosphatidylglycerol. Other examples include dimyristoyl phosphatidylserine ("DMPS"), dipalmitoyl phosphatidylserine ("DPPS"), brain phosphatidylserine ("BPS"), dilauryloylphosphatidylglycerol ("DLPG"), dimyristoylphosphatidylglycerol ("DMPG"), dipalmitoylphosphatidylglycerol ("DPPG"), distearoylphosphatidylglycerol ("DSPG"), and dioleoylphosphatidylglycerol ("DOPG").

The lipid component may optionally include cholesterol of polyethyleneglycol (PEG).

Other possible lipid components include cationic lipids. Non-limiting examples of cationic lipids include 1,2-dioleyl-3-trymethylammoniumpropane (DOTAP), 1,2-dioleoyl-3-dimethylammonium-propane (DODAP), dimethyldioctadecylammonium bromide (DDAB), N-[1-(2, 3-dioleyloxy)propyl]-N,N,N-trimethylammonium chloride (DOTMA), and DC-cholesterol.

The lipid component may include a single type of lipid, or it may include two or more distinct types of lipids. In some embodiments, the composition includes liposomes. Liposomes are discussed in detail elsewhere in this specification.

In some embodiments, the composition is a solution, an emulsion, a cream, a lotion, a gel, or an ointment. The emulsion may be an oil-in-water emulsion or a water-in-oil emulsion.

The composition may include any amount of chimeric polypeptide or nucleic acid encoding a chimeric polypeptide as set forth herein. For example, in some embodiments, the composition includes from about 0.001% to about 5.0% by weight of polypeptide.

The present invention also generally concerns methods of delivering a filaggrin polypeptide into a cell, comprising contacting a cell with any of the aforementioned chimeric polypeptides, wherein the filaggrin polypeptide is delivered into the cell. The cell may be any type of cell. In particular embodiments, the cell is a skin cell. For example, the skin cell may be a basal cell, a squamous cell, a melanocyte, or a keratinocyte.

The invention also in part concerns methods of treating or preventing a skin disease or skin disorder in a subject, involving administering to a subject an effective amount of a composition that includes (a) a recombinant chimeric polypeptide as set forth above or (b) a nucleic acid encoding any of the aforementioned chimeric polypeptides. The subject may be any subject, but in particular embodiments the subject is a mammal. Non-limiting examples of mammals include mice, rats, rabbits, cats, dogs, sheep, goats, pigs, horses, cows, primates, and humans. In particular embodiments, the subject is a human. For example, the human may have or be at risk of developing a skin disease or disorder. In some embodiments, the human is a patient with a skin disease. Non-limiting examples of skin diseases are set forth elsewhere in this specification. In particular embodiments, the skin disease is ichthyosis vulgaris or atopic dermatitis.

The composition may be administered to the subject using any method known to those of ordinary skill in the art. In particular embodiments, administering involves topically applying the composition to a skin surface of the subject. The skin surface may be a mucosal surface, or it may be a skin surface that does not include mucosa. The mucosa may include oral mucosa, vaginal mucosa, cervical mucosa, or anal mucosa.

The compositions set forth herein may optionally include one or more additional agents that can be applied in the treatment or prevention of a skin disease or disorder in a subject. Non-limiting examples of additional agents include a moisturizer, an exfoliating agent, an anti-inflammatory agent, or an antimicrobial agent. Others are detailed elsewhere in this specification. In some embodiments, the composition includes a lipid component, including any of the lipid components as set forth above. The composition may optionally include liposomes.

The composition may be formulated in any manner known to those of ordinary skill in the art. In some embodiments, the composition is a solution, an emulsion, a cream, a lotion, a gel, or an ointment. The emulsion may be an oil-in-water emulsion or a water-in-oil emulsion. The composition may include any amount of active ingredient(s). For example, the composition may include from about 0.001% to about 5.0% by weight of chimeric polypeptide or other ingredient.

Other aspects of the present invention concern kits. The kit may include a sealed container that includes a recombinant polypeptide as set forth above, or a nucleic acid encoding a recombinant polypeptide as set forth above. The sealed container may be any type of sealed container. Non-limiting examples of sealed containers include a vial, a bottle, a dispenser, or a package. The kit may optionally include an applicator. The kit may include a sealed container that includes any of the compositions as set forth herein.

It is specifically contemplated that any limitation discussed with respect to one embodiment of the invention may apply to any other embodiment of the invention. Furthermore, any composition of the invention may be used in any method of the invention, and any method of the invention may be used to produce or to utilize any composition of the invention.

The use of the term "or" in the claims is used to mean "and/or" unless explicitly indicated to refer to alternatives only or the alternative are mutually exclusive, although the disclosure supports a definition that refers to only alternatives and "and/or."

Throughout this application, the term "about" is used to indicate that a value includes the standard deviation of error for the device and/or method being employed to determine the value.

As used herein the specification, "a" or "an" may mean one or more, unless clearly indicated otherwise. As used herein in the claim(s), when used in conjunction with the word "comprising," the words "a" or "an" may mean one or more than one. As used herein "another" may mean at least a second or more.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DESCRIPTION OF ILLUSTRATIVE EMBODIMENTS

The present invention is in part based on the finding that the therapeutic efficacy of filaggrin as an agent to treat or prevent skin disease can be significantly improved by attaching a cell importation signal sequence to the filaggrin polypeptide. The cell importation sequence may include, for example, a motif of two to fifteen amino acids that include at least one arginine residue and at least one methionine residue. These polypeptides, and nucleic acids encoding these polypeptides, have application in the treatment or prevention of a wide variety of conditions, including skin diseases or disorders associated with abnormal keratinization or abnormal epidermal differentiation.

A. POLYPEPTIDES

1. Polypeptides in General

The present invention concerns polypeptides that includes a filaggrin amino acid sequence and a cell importation signal sequence. As used herein, a "polypeptide" generally is defined herein to refer to a peptide sequence of about 2 to about 10,000 or more amino acid residues.

The term "amino acid" not only encompasses the 20 common amino acids in naturally synthesized proteins, but also includes any modified, unusual, or synthetic amino acid. One of ordinary skill in the art would be familiar with modified, unusual, or synthetic amino acids. Examples of modified and unusual amino acids are shown on Table 1 below.

TABLE 1

Modified and Unusual Amino Acids

| Abbr. | Amino Acid | Abbr. | Amino Acid |
|---|---|---|---|
| Aad | 2-Aminoadipic acid | EtAsn | N-Ethylasparagine |
| Baad | 3-Aminoadipic acid | Hyl | Hydroxylysine |
| Bala | β-alanine, β-Amino-propionic acid | AHyl | allo-Hydroxylysine |
| Abu | 2-Aminobutyric acid | 3Hyp | 3-Hydroxyproline |
| 4Abu | 4-Aminobutyric acid, piperidinic acid | 4Hyp | 4-Hydroxyproline |
| Acp | 6-Aminocaproic acid | Ide | Isodesmosine |
| Ahe | 2-Aminoheptanoic acid | AIle | allo-Isoleucine |
| Aib | 2-Aminoisobutyric acid | MeGly | N-Methylglycine, sarcosine |
| Baib | 3-Aminoisobutyric acid | MeIle | N-Methylisoleucine |
| Apm | 2-Aminopimelic acid | MeLys | 6-N-Methyllysine |
| Dbu | 2,4-Diaminobutyric acid | MeVal | N-Methylvaline |
| Des | Desmosine | Nva | Norvaline |
| Dpm | 2,2'-Diaminopimelic acid | Nle | Norleucine |
| Dpr | 2,3-Diaminopropionic acid | Orn | Ornithine |
| EtGly | N-Ethylglycine | | |

The polypeptides that are included in the methods set forth herein are chimeric in that they comprise a filaggrin amino acid sequence and a cell importation signal sequence. The polypeptides set forth herein may comprise one or more cell importation signal sequences, which may or may not be identical. Similarly, the polypeptides set forth herein may comprise one or more filaggrin amino acid sequences, which may or may not be identical.

In certain embodiments of the present invention, the polypeptide is a fusion polypeptide that includes a filaggrin amino acid sequence linked at the N- or C-terminus to a cell importation signal sequence. In other embodiments, the polypeptide comprises a linker interposed between the filaggrin amino acid sequence and the cell importation signal sequence. Linkers are discussed in greater detail in the specification below.

Furthermore, the polypeptides set forth herein may comprises a sequence of any number of additional amino acid residues at either the N-terminus or C-terminus of the amino acid sequence that includes the filaggrin amino acid sequence and the cell importation signal sequence. For example, there may be an amino acid sequence of about 3 to about 10,000 or more amino acid residues at either the N-terminus, the C-terminus, or both the N-terminus and C-terminus of the amino acid sequence that includes the filaggrin amino acid sequence and the cell importation signal sequence.

The polypeptide may include the addition of an immunologically active domain, such as an antibody epitope or other tag, to facilitate targeting or purification of the polypeptide. The use of 6×His and GST (glutathione S transferase) as tags is well known. Inclusion of a cleavage site at or near the fusion junction will facilitate removal of the extraneous polypeptide after purification. Other amino acid sequences that may be included in the polypeptide include functional domains, such as active sites from enzymes such as a hydrolase, glycosylation domains, cellular targeting signals or transmembrane regions. The polypeptide may further include one or more additional tissue-targeting moieties.

The polypeptides of the present invention may possess deletions and/or substitutions of amino acids relative to the native sequence; thus, sequences with a deletion, sequences with a substitution, and sequences with a deletion and a substitution are contemplated for inclusion in the polypeptides of the present invention. In some embodiments, these polypeptides may further include insertions or added amino acids, such as linkers.

Substitutional or replacement variants typically contain the exchange of one amino acid for another at one or more sites within the protein and may be designed to modulate one or more properties of the polypeptide, particularly to increase its efficacy or specificity. Substitutions of this kind preferably are conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

In addition to a deletion or substitution, the polypeptides may possess an insertion one or more residues. This may include the addition of one or more amino acid residues.

The term "biologically functional equivalent" is well understood in the art and is further defined in detail herein. Accordingly, sequences that have between about 70% and about 80%, or between about 81% and about 90%, or even between about 91% and about 99% of amino acids that are identical or functionally equivalent to the amino acids of the native filaggrin amino acid sequence or cell importation signal sequence are included, provided the biological activity of the native sequence is maintained.

Thus, the filaggrin amino acid sequence may be a biologically functionally equivalent to the native counterparts. For example, the filaggrin amino acid sequence may be functionally equivalent in terms of ability to maintain epidermal health. In some embodiments, the filaggrin amino acid sequence may have greater biological activity than their native counterparts.

The following is a discussion based upon changing of the amino acids of a polypeptide to create an equivalent, or even an improved, second-generation molecule. For example, certain amino acids may be substituted for other amino acids in a polypeptide without appreciable loss of function, such as ability to interact with an endothelial cell of a blood vessel. Since it is the interactive capacity and nature of a polypeptide that defines that polypeptide's biological functional activity, certain amino acid substitutions can be made in a polypeptide sequence and nevertheless produce a polypeptide with like properties.

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still produce a biologically equivalent and immunologically equivalent protein. In such changes, the substitution of amino acids whose hydrophilicity values are within ±2 is preferred, those that are within ±1 are particularly preferred, and those within ±0.5 are even more particularly preferred.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

2. Filaggrin Amino Acid Sequences

The filaggrin amino acid sequences contemplated for inclusion in the polypeptides, compositions, and methods of the present invention may be obtained from any source. For example, the filaggrin amino acid may be obtained from a natural source or may be chemically synthesized. The filaggrin amino acid sequence may be from any species. For example, it may be a mammalian filaggrin amino acid sequence. Non-limiting examples include mouse, rat, rabbit, goat, sheep, horse, cow, dog, cat, primate, or human amino acid sequence. In preferred embodiments, the filaggrin amino acid sequence is a human amino acid sequence. Non-limiting examples of filaggrin proteins are set forth in Table 2.

TABLE 2

Examples of Filaggrin Protein Sequences

| Sequence | GenBank Accession No. | SEQ ID NO: |
|---|---|---|
| Filaggrin, *Homo sapiens* |  | 1 |
| Filaggrin, *Homo sapiens* | NP_002007 | 2 |
| Filaggrin, *Homo sapiens* | AAA52454 | 3 |
| Filaggrin, *Homo sapiens* | CAI19595 | 4 |
| Filaggrin, *Homo sapiens* | P20930 | 5 |
| Filaggrin, *Mus musculus* |  | 6 |
| Filaggrin, *Mus musculus* | AAM23016 | 7 |
| Filaggrin, *Mus musculus* | AAA75559 | 8 |
| Filaggrin, *Mus musculus* | AAA37626 | 9 |
| Filaggrin, *Mus musculus* | AAA37625 | 10 |
| Filaggrin, *Mus musculus* | XP_485270 | 11 |
| Filaggrin, *Mus musculus* | P11088 | 12 |
| Filaggrin, *Mus musculus* | EDL00668.1 | 13 |
| Filaggrin, *Rattus norvegicus* | EDL87862 | 14 |

TABLE 2-continued

Examples of Filaggrin Protein Sequences

| Sequence | GenBank Accession No. | SEQ ID NO: |
|---|---|---|
| Filaggrin, *Pan troglodytes* | XP_001134714 | 15 |
| Filaggrin, *Pan troglodytes* | XP_513808 | 16 |
| Filaggrin, *Bos taurus* | XP_001255583 | 17 |
| Filaggrin, *Macaca mulatta* | XP_001101725.1 | 18 |
| Filaggrin, *Macaca mulatta* | XP_001109011.1 | 19 |

3. Cell Importation Signal Sequences

Any cell importation signal sequence that facilitates entry of a filaggrin amino acid sequence into a cell is contemplated as a cell importation signal sequence of the present invention. In some embodiments, the signal sequence includes a motif of two to fifteen amino acids, wherein the motif includes at least one arginine amino acid residue and at least one methionine amino acid residue. The arginine amino acid residue and the methionine amino acid residue may be consecutive residues within the motif, or they may be separated by one or more intervening amino acids. In some embodiments of the recombinant polypeptides of the present invention, the polypeptide includes more than one motif of two to fifteen amino acids, where each motif includes at least one arginine amino acid residue and at least one methionine amino acid residue. The motifs may include identical amino acid sequences or may have distinct amino acid sequences. Methionine/arginine-rich repeat motifs are discussed in Datar et al. (1993). Non-limiting examples of filaggrin proteins are set forth in Table 3.

TABLE 3

Examples of Cell Importation Signal Sequences

| Sequence | SEQ ID NO: |
|---|---|
| RMRRMRRMRR | 23 |
| RGRRGRRGRR | 24 |
| RRRRRRRRRR | 25 |
| RARRARRARR | 26 |
| RTRRTRRTRR | 27 |
| RSRRSRRSRR | 28 |
| RVRRVRRVRR | 29 |
| RKRRKRRKRR | 30 |
| RRRRRR | 31 |
| RRRRRRR | 32 |
| RRRRRRRR | 33 |
| RRRRRRRRR | 34 |
| RRRRRRRRRR | 35 |
| RRRRRRRRRRR | 36 |
| RRRRRRRRRRRR | 37 |
| RRRRRRRRRRRRR | 38 |

4. Methods of Polypeptide Synthesis

In certain embodiments of the present invention, the polypeptide is encoded by a single recombinant nucleic acid sequence using recombinant techniques. In other embodiments, the filaggrin amino acid sequence and the cell importation signal sequence are encoded by separate nucleic acid sequences, and subsequently joined by chemical conjugation. In further embodiments, the polypeptide has been synthesized de novo.

a. Recombinant Techniques

In certain embodiments of the present invention, the chimeric polypeptide is encoded by a single recombinant polynucleotide using recombinant techniques well-known to those of ordinary skill in the art. The polynucleotide may include a sequence of additional nucleic acids that direct the expression of the chimeric polypeptide in appropriate host cells.

Due to the inherent degeneracy of the genetic code, other DNA sequences that encode substantially the same or a functionally equivalent amino acid sequence, may be used in the practice of the invention of the cloning and expression of the chimeric protein. Such DNA sequences include those capable of hybridizing to the chimeric sequences or their complementary sequences under stringent conditions. In one embodiment, the phrase "stringent conditions" as used herein refers to those hybridizing conditions that (1) employ low ionic strength and high temperature for washing, for example, 0.015 M NaCl/0.0015 M sodium citrate/0.1% SDS at 50° C.; (2) employ during hybridization a denaturing agent such as formamide, for example, 50% (vol/vol) formamide with a 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C.; or (3) employ 50% formamide, 5×SSC (0.75 M NaCl, 0.075 M Sodium pyrophosphate, 5×Denhardt's solution, sonicated salmon sperm DNA (50 µg/ml), 0.1% SDS, and 10% dextran sulfate at 42° C., with washes at 42° C. in 0.2×SSC and 0.1% SDS.

Altered DNA sequences that may be used in accordance with the invention include deletions, additions or substitutions of different nucleotide residues resulting in a sequence that encodes the same or a functionally equivalent polynucleotide. The polynucleotide may contain deletions, additions or substitutions of amino acid residues within a chimeric sequence, which result in a silent change thus producing a functionally equivalent chimeric polynucleotide. Such amino acid substitutions may be made on the basis of similarity in polarity, charge, solubility, hydrophobicity, hydrophilicity, and/or the amphipathic nature of the residues involved, as discussed above.

The DNA sequences of the invention may be engineered in order to alter a chimeric coding sequence for a variety of ends, including but not limited to, alterations that modify processing and expression of the gene product. For example, mutations may be introduced using techniques that are well known in the art, e.g., site-directed mutagenesis, to insert new restriction sites, to alter glycosylation patterns, phosphorylation, etc.

In order to express a biologically active chimeric polypeptide, the nucleotide sequence coding for a chimeric polypeptide, or a functional equivalent, is inserted into an appropriate expression vector, i.e., a vector that contains the necessary elements for the transcription and translation of the inserted coding sequence. The chimeric gene products as well as host cells or cell lines transfected or transformed with recombinant chimeric expression vectors can be used for a variety of purposes. These include, but are not limited to, generating antibodies (i.e., monoclonal or polyclonal) that bind to epitopes of the proteins to facilitate their purification.

Methods that are well known to those skilled in the art can be used to construct expression vectors containing the chimeric coding sequence and appropriate transcriptional/translational control signals. These methods include in vitro recombinant DNA techniques, synthetic techniques and in vivo recombination/genetic recombination. See, for example, the techniques described in Sambrook et al., 2001.

A variety of host-expression vector systems may be utilized to express the chimeric polypeptide coding sequence. These include but are not limited to microorganisms such as bacteria transformed with recombinant bacteriophage DNA, plasmid DNA or cosmid DNA expression vectors containing the chimeric protein coding sequence; yeast transformed with recombinant yeast expression vectors containing the chimeric protein coding sequence; insect cell systems infected with recombinant virus expression vectors (e.g., baculovirus) containing the chimeric protein coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the chimeric protein coding sequence; or animal cell systems. It should be noted that since most apoptosis-inducing proteins cause programmed cell death in mammalian cells, it is preferred that the chimeric protein of the invention be expressed in prokaryotic or lower eukaryotic cells. Section 6 illustrates that IL2-Bax may be efficiently expressed in E. coli.

The expression elements of each system vary in their strength and specificities. Depending on the host/vector system utilized, any of a number of suitable transcription and translation elements, including constitutive and inducible promoters, may be used in the expression vector. For example, when cloning in bacterial systems, inducible promoters such as pL of bacteriophage λ, plac, ptrp, ptac (ptrp-lac hybrid promoter; cytomegalovirus promoter) and the like may be used; when cloning in insect cell systems, promoters such as the baculovirus polyhedrin promoter may be used; when cloning in plant cell systems, promoters derived from the genome of plant cells (e.g., heat shock promoters; the promoter for the small subunit of RUBISCO; the promoter for the chlorophyll α/β binding protein) or from plant viruses (e.g., the 35S RNA promoter of CaMV; the coat protein promoter of TMV) may be used; when cloning in mammalian cell systems, promoters derived from the genome of mammalian cells (e.g., metallothionein promoter) or from mammalian viruses (e.g., the adenovirus late promoter; the vaccinia virus 7.5K promoter) may be used; when generating cell lines that contain multiple copies of the chimeric DNA, SV40-, BPV- and EBV-based vectors may be used with an appropriate selectable marker.

In bacterial systems a number of expression vectors may be advantageously selected depending upon the use intended for the chimeric polypeptide expressed. For example, when large quantities of chimeric polypeptide are to be produced, vectors that direct the expression of high levels of protein products that are readily purified may be desirable. Such vectors include but are not limited to the E. coli expression vector pUR278 (Ruther et al., 1983), in which the chimeric protein coding sequence may be ligated into the vector in frame with the lacZ coding region so that a hybrid AS-lacZ protein is produced; pIN vectors (Van Heeke and Schuster, 1989); and the like.

An alternative expression system that could be used to express chimeric polypeptide is an insect system. In one such system, Autographa californica nuclear polyhidrosis virus (AcNPV) is used as a vector to express foreign genes. The virus grows in Spodoptera frugiperda cells. The chimeric protein coding sequence may be cloned into non-essential regions (for example the polyhedrin gene) of the virus and placed under control of an AcNPV promoter (for example the polyhedrin promoter). Successful insertion of the chimeric polypeptide coding sequence will result in inactivation of the polyhedrin gene and production of non-occluded recombinant virus (i.e., virus lacking the proteinaceous coat coded for by the polyhedrin gene). These recombinant viruses are then used to infect Spodoptera frugiperda cells in which the inserted gene is expressed. (e.g., see Smith et al., 1983; U.S. Pat. No. 4,215,051).

Specific initiation signals may also be required for efficient translation of the inserted chimeric protein coding sequence. These signals include the ATG initiation codon and adjacent sequences. In cases where the entire chimeric gene, including its own initiation codon and adjacent sequences, is inserted into the appropriate expression vector, no additional translational control signals may be needed. However, in cases where the chimeric protein coding sequence does not include its own initiation codon, exogenous translational control signals, including the ATG initiation codon, must be provided. Furthermore, the initiation codon must be in phase with the reading frame of the chimeric protein coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. The presence of consensus N-glycosylation sites in a chimeric protein may require proper modification for optimal chimeric protein function. Different host cells have characteristic and specific mechanisms for the post-translational processing and modification of proteins. Appropriate cell lines or host systems can be chosen to ensure the correct modification and processing of the chimeric protein. To this end, eukaryotic host cells which possess the cellular machinery for proper processing of the primary transcript, glycosylation, and phosphorylation of the chimeric protein may be used. Such mammalian host cells include but are not limited to CHO, VERO, BHK, HeLa, COS, MDCK, 293, W138, and the like.

For long-term, high-yield production of recombinant chimeric polypeptides, stable expression is preferred. For example, cell lines that stably express the chimeric polypeptide may be engineered. Rather than using expression vectors that contain viral originals of replication, host cells can be transformed with a chimeric coding sequence controlled by appropriate expression control elements (e.g., promoter, enhancer, sequences, transcription terminators, polyadenylation sites, etc.), and a selectable marker. Following the introduction of foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines.

A number of selection systems may be used, including but not limited to the herpes simplex virus thymidine kinase (Wigler et al., 1977), hypoxanthine-guanine phosphoribosyltransferase (Szybalski and Szybalski, 1962), and adenine phosphoribosyltransferase (Lowy et al., 1980) genes can be employed in tk-, hgprt- or aprt-cells, respectively. Also, antimetabolite resistance can be used as the basis of selection for dhfr, which confers resistance to methotrexate (Wigler et al., 1980; O'Hare et al., 1981); gpt, which confers resistance to mycophenolic acid (Mulligan and Berg, 1981); neo, which confers resistance to the aminoglycoside G-418 (Colbere-Garapin et al., 1981); and hygro, which confers resistance to hygromycin (Santerre et al., 1984) genes. Additional selectable genes have been described, namely trpB, which allows cells to utilize indole in place of tryptophan; hisD, which allows cells to utilize histinol in place of histidine (Hartman and Mulligan, 1988); and ODC (ornithine decarboxylase) which confers resistance to the ornithine decarboxylase inhibitor, 2-(difluoromethyl)-DL-ornithine, DFMO (see McConlogue, 1986).

b. De Novo Synthesis

In an alternate embodiment of the invention, the chimeric polypeptide could be synthesized de novo in whole or in part, using chemical methods well known in the art (see, for example, Caruthers et al., 1980; Crea and Horn, 1980; and Chow and Kempe, 1981). For example, the component amino acid sequences can be synthesized by solid phase techniques, cleaved from the resin, and purified by preparative high performance liquid chromatography followed by chemical linkage to form a chimeric protein. (e.g., see Creighton, 1983). The composition of the synthetic peptides may be confirmed by amino acid analysis or sequencing (e.g., the Edman degradation procedure; see Creighton, 1983).

Polypeptide synthesis techniques are well known to those of skill in the art (see, e.g., Bodanszky et al., 1976). These synthetic methods involve the sequential addition of one or more amino acid residues or suitable protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group, such as lysine.

Using solid phase synthesis as an example, the protected or derivatized amino acid is attached to an inert solid support through its unprotected carboxyl or amino group. The protecting group of the amino or carboxyl group is then selectively removed and the next amino acid in the sequence having the complementary (amino or carboxyl) group suitably protected is admixed and reacted with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to provide the final peptide. Such protecting group moieties may be used in the course of synthesis, but they are removed before the peptides are used. Additional reactions may be necessary, as described elsewhere, to form intramolecular linkages to restrain conformation.

c. Linkers

Alternatively, the two moieties of the chimeric polypeptide produced by synthetic or recombinant methods may be conjugated by linkers according to methods well known in the art (Brinkmann and Pastan, 1994). As used herein, a "linker" is a chemical or peptide or polypeptide that links an endothelial targeting amino acid sequence with a cytotoxic amino acid sequence.

The two coding sequences can be fused directly without any linker or by using a flexible polylinker, such as one composed of the pentamer Gly-Gly-Gly-Gly-Ser (SEQ ID NO:39) repeated 1 to 3 times. Such linker has been used in constructing single chain antibodies (scFv) by being inserted between VH and VL (Bird et al., 1988; Huston et al., 1988). The linker is designed to enable the correct interaction between two beta-sheets forming the variable region of the single chain antibody. Other linkers which may be used include Glu-Gly-Lys-Ser-Ser-Gly-Ser-Gly-Ser-Glu-Ser-Lys-Val-Asp (SEQ ID NO:40) (Chaudhary et al., 1990) and Lys-Glu-Ser-Gly-Ser-Val-Ser-Ser-Glu-Gln-Leu-Ala-Gln-Phe-Arg-Ser-Leu-Asp (SEQ ID NO:41) (Bird et al., 1988).

Multiple peptides or polypeptides may also be joined via a biologically-releasable bond, such as a selectively-cleavable linker or amino acid sequence. For example, peptide linkers that include a cleavage site for an enzyme preferentially located or active within a tumor environment are contemplated. Exemplary forms of such peptide linkers are those that are cleaved by urokinase, plasmin, thrombin, Factor IXa, Factor Xa, or a metallaproteinase, such as collagenase, gelatinase, or stromelysin. Alternatively, polypeptides may be joined to an adjuvant. It can be considered as a general guideline that any linker known to those of ordinary skill in the art is contemplated for use as a linker in the present invention.

It is contemplated that cross-linkers may be implemented with the polypeptide molecules of the present invention. Cross-linking reagents are used to form molecular bridges that tie together functional groups of two different molecules, e.g., a stabilizing and coagulating agent. To link two different polypeptides in a step-wise manner, hetero-bifunctional cross-linkers can be used that eliminate unwanted homopolymer formation. Bifunctional cross-linking reagents have been extensively used for a variety of purposes including preparation of affinity matrices, modification and stabilization of diverse structures, identification of binding sites, and structural studies. In the context of the invention, such cross-linker may be used to stabilize the polypeptide or to render it more useful as a therapeutic, for example, by improving the polypeptide's targeting capability or overall efficacy. Cross-linkers may also be cleavable, such as disulfides, acid-sensitive linkers, and others. Homobifunctional reagents that carry two identical functional groups proved to be highly efficient in inducing cross-linking between identical and different macromolecules or subunits of a macromolecule, and linking of polypeptides to specific binding sites on binding partners. Heterobifunctional reagents contain two different functional groups. By taking advantage of the differential reactivities of the two different functional groups, cross-linking can be controlled both selectively and sequentially. The bifunctional cross-linking reagents can be divided according to the specificity of their functional groups, e.g., amino, sulfhydryl, guanidino, indole, carboxyl specific groups. Of these, reagents directed to free amino groups have become especially popular because of their commercial availability, ease of synthesis and the mild reaction conditions under which they can be applied. A majority of heterobifunctional cross-linking reagents contains a primary amine-reactive group and a thiol-reactive group.

In another example, heterobifunctional cross-linking reagents and methods of using the cross-linking reagents are described (U.S. Pat. No. 5,889,155, specifically incorporated herein by reference in its entirety). The cross-linking reagents combine a nucleophilic hydrazide residue with an electrophilic maleimide residue, allowing coupling in one example, of aldehydes to free thiols. The cross-linking reagent can be modified to cross-link various functional groups and is thus useful for cross-linking polypeptides and sugars. In instances where a particular polypeptide, such as gelonin, does not contain a residue amenable for a given cross-linking reagent in its native sequence, conservative genetic or synthetic amino acid changes in the primary sequence can be utilized. Table 4 details certain exemplary hetero-bifunctional cross-linkers considered useful in the present invention.

TABLE 4

HETERO-BIFUNCTIONAL CROSS-LINKERS

| Linker | Reactive Toward | Advantages and Applications | Spacer Arm Length\after cross-linking |
|---|---|---|---|
| SMPT | Primary amines Sulfhydryls | Greater stability | 11.2 A |
| SPDP | Primary amines Sulfhydryls | Thiolation Cleavable cross-linking | 6.8 A |
| LC-SPDP | Primary amines Sulfhydryls | Extended spacer arm | 15.6 A |
| Sulfo-LC-SPDP | Primary amines Sulfhydryls | Extended spacer arm Water-soluble | 15.6 A |
| SMCC | Primary amines Sulfhydryls | Stable maleimide reactive group Enzyme-antibody conjugation Hapten-carrier protein conjugation | 11.6 A |
| Sulfo-SMCC | Primary amines Sulfhydryls | Stable maleimide reactive group Water-soluble Enzyme-antibody conjugation | 11.6 A |
| MBS | Primary amines Sulfhydryls | Enzyme-antibody conjugation Hapten-carrier protein conjugation | 9.9 A |
| Sulfo-MBS | Primary amines Sulfhydryls | Water-soluble | 9.9 A |
| SIAB | Primary amines Sulfhydryls | Enzyme-antibody conjugation | 10.6 A |
| Sulfo-SIAB | Primary amines Sulfhydryls | Water-soluble | 10.6 A |
| SMPB | Primary amines Sulfhydryls | Extended spacer arm Enzyme-antibody conjugation | 14.5 A |
| Sulfo-SMPB | Primary amines Sulfhydryls | Extended spacer arm Water-soluble | 14.5 A |
| EDC/Sulfo-NHS | Primary amines Carboxyl groups | Hapten-Carrier conjugation | 0 |
| ABH | Carbohydrates Nonselective | Reacts with sugar groups | 11.9 A | d. Protein Purification

In certain embodiments of the present invention, the polypeptide has been purified. Generally, "purified" will refer to a polypeptide composition that has been subjected to fractionation to remove various other components, and which composition substantially retains its expressed biological activity. Where the term "substantially purified" is used, this designation will refer to a composition in which the polypeptide or peptide forms the major component of the composition, such as constituting about 50% to about 99.9% or more of the proteins in the composition.

Various methods for quantifying the degree of purification of the polypeptide will be known to those of skill in the art in light of the present disclosure. Exemplary techniques include high performance liquid chromatography, ion exchange chromatography, gel electrophoresis, affinity chromatography and the like. The actual conditions used to purify a particular polypeptide will depend, in part, on factors such as net charge, hydrophobicity, hydrophilicity, etc., and will be apparent to those having skill in the art.

For affinity chromatography purification, any antibody that specifically binds the polypeptide may be used. For the production of antibodies, various host animals, including but not limited to rabbits, mice, rats, etc., may be immunized by injection with a chimeric protein or a fragment thereof. The protein may be attached to a suitable carrier, such as bovine serum albumin (BSA), by means of a side chain functional group or linkers attached to a side chain functional group. Various adjuvants may be used to increase the immunological response, depending on the host species, including but not limited to, Freund's (complete and incomplete), mineral gels such as aluminum hydroxide, surface active substances such as lysolecithin, pluronic polyols, polyanions, peptides, oil emulsions, keyhold limpet hemocyanin, dinitrophenol, and potentially useful human adjuvants such as BCG (bacilli Calmetter-Guerin) and *Corynebacterium parvum*.

Monoclonal antibodies to a chimeric polypeptide may be prepared using any technique that provides for the production of antibody molecules by continuous cell lines in culture. These include but are not limited to the hybridoma technique originally described by Kohler and Milstein (1975), the human B-cell hybridoma technique (Cote et al., 1983), and the EBV-hybridoma technique (Cole et al., 1985). In addition, techniques developed for the production of "chimeric antibodies" (Morrison et al., 1984; Neuberger et al., 1984; Takeda et al., 1985) by splicing the genes from a mouse antibody molecule of appropriate antigen specificity together with genes from a human antibody molecule of appropriate biological activity can be used. Alternatively, techniques described for the production of single chain antibodies (U.S. Pat. No. 4,946,778) can be adapted to produce chimeric protein-specific single chain antibodies for chimeric protein purification and detection.

B. NUCLEIC ACIDS

The present invention includes nucleic acids that include a nucleic acid sequence that encodes a recombinant polypeptide of the present invention.

The term "nucleic acid" is well known in the art. A "nucleic acid" as used herein will generally refer to a molecule (i.e., a strand) of DNA, RNA or a derivative or analog thereof, comprising a nucleobase. A nucleobase includes, for example, a naturally occurring purine or pyrimidine base found in DNA (e.g., an adenine "A," a guanine "G," a thymine "T" or a cytosine "C") or RNA (e.g., an A, a G, an uracil "U" or a C). The term "nucleic acid" encompass the terms "oligonucleotide" and "polynucleotide," each as a subgenus of the term "nucleic acid." The term "oligonucleotide" refers to a molecule of between 3 and about 100 nucleobases in length. The term "polynucleotide" refers to at least one molecule of greater than about 100 nucleobases in length.

These definitions refer to a single-stranded or double-stranded nucleic acid molecule. Double stranded nucleic acids are formed by fully complementary binding, although in some embodiments a double stranded nucleic acid may be formed by partial or substantial complementary binding. Thus, a nucleic acid may encompass a double-stranded molecule that comprises one or more complementary strand(s) or "complement(s)" of a particular sequence, typically comprising a molecule. As used herein, a single stranded nucleic acid may be denoted by the prefix "ss" and a double stranded nucleic acid by the prefix "ds".

1. Nucleobases

As used herein a "nucleobase" refers to a heterocyclic base, such as for example a naturally occurring nucleobase (i.e., an A, T, G, C or U) found in at least one naturally occurring nucleic acid (i.e., DNA and RNA), and naturally or non-naturally occurring derivative(s) and analogs of such a nucleobase. A nucleobase generally can form one or more hydrogen bonds ("anneal" or "hybridize") with at least one naturally occurring nucleobase in manner that may substitute for naturally occurring nucleobase pairing (e.g., the hydrogen bonding between A and T, G and C, and A and U).

"Purine" and/or "pyrimidine" nucleobase(s) encompass naturally occurring purine and/or pyrimidine nucleobases and also derivative(s) and analog(s) thereof, including but not limited to, those a purine or pyrimidine substituted by one or more of an alkyl, caboxyalkyl, amino, hydroxyl, halogen (i.e., fluoro, chloro, bromo, or iodo), thiol or alkylthiol moeity. Preferred alkyl (e.g., alkyl, caboxyalkyl, etc.) moeities comprise of from about 1, about 2, about 3, about 4, about 5, to about 6 carbon atoms. A nucleobase may be comprised in a nucleside or nucleotide, using any chemical or natural synthesis method described herein or known to one of ordinary skill in the art.

2. Nucleosides

As used herein, a "nucleoside" refers to an individual chemical unit comprising a nucleobase covalently attached to a nucleobase linker moiety. A non-limiting example of a "nucleobase linker moiety" is a sugar comprising 5-carbon atoms (i.e., a "5-carbon sugar"), including but not limited to a deoxyribose, a ribose, an arabinose, or a derivative or an analog of a 5-carbon sugar. Non-limiting examples of a derivative or an analog of a 5-carbon sugar include a 2'-fluoro-2'-deoxyribose or a carbocyclic sugar where a carbon is substituted for an oxygen atom in the sugar ring.

Different types of covalent attachment(s) of a nucleobase to a nucleobase linker moiety are known in the art. By way of non-limiting example, a nucleoside comprising a purine (i.e., A or G) or a 7-deazapurine nucleobase typically covalently attaches the 9 position of a purine or a 7-deazapurine to the 1'-position of a 5-carbon sugar. In another non-limiting example, a nucleoside comprising a pyrimidine nucleobase (i.e., C, T or U) typically covalently attaches a 1 position of a pyrimidine to a 1'-position of a 5-carbon sugar (Kornberg and Baker, 1992).

3. Nucleotides

As used herein, a "nucleotide" refers to a nucleoside further comprising a "backbone moiety". A backbone moiety generally covalently attaches a nucleotide to another molecule comprising a nucleotide, or to another nucleotide to form a nucleic acid. The "backbone moiety" in naturally occurring nucleotides typically comprises a phosphorus moiety, which is covalently attached to a 5-carbon sugar. The attachment of the backbone moiety typically occurs at either the 3'- or 5'-position of the 5-carbon sugar. However, other types of attachments are known in the art, particularly when a nucleotide comprises derivatives or analogs of a naturally occurring 5-carbon sugar or phosphorus moiety.

4. Nucleic Acid Analogs

A nucleic acid may comprise, or be composed entirely of, a derivative or analog of a nucleobase, a nucleobase linker moiety and/or backbone moiety that may be present in a naturally occurring nucleic acid. As used herein a "derivative" refers to a chemically modified or altered form of a naturally occurring molecule, while the terms "mimic" or "analog" refer to a molecule that may or may not structurally resemble a naturally occurring molecule or moiety, but possesses similar functions. As used herein, a "moiety" generally refers to a smaller chemical or molecular component of a larger chemical or molecular structure. Nucleobase, nucleoside and nucleotide analogs or derivatives are well known in the art, and have been described (see for example, Scheit, 1980, incorporated herein by reference).

Additional non-limiting examples of nucleosides, nucleotides, or nucleic acids comprising 5-carbon sugar and/or backbone moiety derivatives or analogs, include those in U.S. Pat. No. 5,681,947 which describes oligonucleotides comprising purine derivatives that form triple helixes with and/or prevent expression of dsDNA; U.S. Pat. Nos. 5,652,099 and 5,763,167 which describe nucleic acids incorporating fluorescent analogs of nucleosides found in DNA or RNA, particularly for use as fluorescent nucleic acids probes; U.S. Pat. No. 5,614,617 which describes oligonucleotide analogs with substitutions on pyrimidine rings that possess enhanced nuclease stability; U.S. Pat. Nos. 5,670,663, 5,872,232 and 5,859,221 which describe oligonucleotide analogs with modified 5-carbon sugars (i.e., modified 2'-deoxyfuranosyl moieties) used in nucleic acid detection; U.S. Pat. No. 5,446,137 which describes oligonucleotides comprising at least one 5-carbon sugar moiety substituted at the 4' position with a substituent other than hydrogen that can be used in hybridization assays; U.S. Pat. No. 5,886,165 which describes oligonucleotides with both deoxyribonucleotides with 3'-5' internucleotide linkages and ribonucleotides with 2'-5' internucleotide linkages; U.S. Pat. No. 5,714,606 which describes a modified internucleotide linkage wherein a 3'-position oxygen of the internucleotide linkage is replaced by a carbon to enhance the nuclease resistance of nucleic acids; U.S. Pat. No. 5,672,697 which describes oligonucleotides containing one or more 5' methylene phosphonate internucleotide linkages that enhance nuclease resistance; U.S. Pat. Nos. 5,466,786 and 5,792,847 which describe the linkage of a substituent moeity which may comprise a drug or label to the 2' carbon of an oligonucleotide to provide enhanced nuclease stability and ability to deliver drugs or detection moieties; U.S. Pat. No. 5,223,618 which describes oligonucleotide analogs with a 2 or 3 carbon backbone linkage attaching the 4' position and 3' position of adjacent 5-carbon sugar moiety to enhanced cellular uptake, resistance to nucleases and hybridization to target RNA; U.S. Pat. No. 5,470,967 which describes oligonucleotides comprising at least one sulfamate or sulfamide internucleotide linkage that are useful as nucleic acid hybridization probe; U.S. Pat. Nos. 5,378,825, 5,777,092, 5,623,070, 5,610,289 and 5,602,240 which describe oligonucleotides with three or four atom linker moeity replacing phosphodiester backbone moeity used for improved nuclease resistance, cellular uptake and regulating RNA expression; U.S. Pat. No. 5,858,988 which describes hydrophobic carrier agent attached to the 2'-0 position of oligonucleotides to enhanced their membrane permeability and stability; U.S. Pat. No. 5,214,136 which describes oligonucleotides conjugated to anthraquinone at the 5' terminus that possess enhanced hybridization to DNA or RNA; enhanced stability to nucleases; U.S. Pat. No. 5,700,922 which describes PNA-DNA-PNA chimeras wherein the DNA comprises 2'-deoxy-erythro-pentofuranosyl nucleotides for enhanced nuclease resistance, binding affinity, and ability to activate RNase H; and U.S. Pat. No. 5,708,154 which describes RNA linked to a DNA to form a DNA-RNA hybrid.

5. Polyether Nucleic Acids

In certain embodiments, it is contemplated that a nucleic acid comprising a derivative or analog of a nucleoside or nucleotide may be used in the methods and compositions of the invention. A non-limiting example is a "polyether nucleic acid", described in U.S. Pat. No. 5,908,845, incorporated herein by reference. In a polyether nucleic acid, one or more nucleobases are linked to chiral carbon atoms in a polyether backbone.

6. Preparation of Nucleic Acids

A nucleic acid may be made by any technique known to one of ordinary skill in the art, such as chemical synthesis, enzymatic production or biological production. Non-limiting examples of a synthetic nucleic acid (e.g., a synthetic oligonucleotide), include a nucleic acid made by in vitro chemically synthesis using phosphotriester, phosphite or phosphoramidite chemistry and solid phase techniques such as described in EP 266,032, incorporated herein by reference, or via deoxynucleoside H-phosphonate intermediates as described by Froehler et al., 1986 and U.S. Pat. No. 5,705,629, each incorporated herein by reference. In the methods of the present invention, one or more oligonucleotide may be used. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference.

A non-limiting example of an enzymatically produced nucleic acid include one produced by enzymes in amplification reactions such as PCR™ (see for example, U.S. Pat. Nos. 4,683,202 and 4,682,195, each incorporated herein by reference), or the synthesis of an oligonucleotide described in U.S. Pat. No. 5,645,897, incorporated herein by reference. A non-limiting example of a biologically produced nucleic acid includes a recombinant nucleic acid produced (i.e., replicated) in a living cell, such as a recombinant DNA vector replicated in bacteria (see for example, Sambrook et al. 2001, incorporated herein by reference).

7. Purification of Nucleic Acids

A nucleic acid may be purified on polyacrylamide gels, cesium chloride centrifugation gradients, or by any other means known to one of ordinary skill in the art (see for example, Sambrook et al., 2001, incorporated herein by reference).

In certain embodiments, the present invention concerns a nucleic acid that is an isolated nucleic acid. As used herein, the term "isolated nucleic acid" refers to a nucleic acid molecule (e.g., an RNA or DNA molecule) that has been isolated free of, or is otherwise free of, the bulk of the total genomic and transcribed nucleic acids of one or more cells. In certain embodiments, "isolated nucleic acid" refers to a nucleic acid that has been isolated free of, or is otherwise free of, bulk of cellular components or in vitro reaction components such as for example, macromolecules such as lipids or proteins, small biological molecules, and the like.

C. LIPID PREPARATIONS

Some embodiments of the present invention concern polypeptide- or nucleic acid-containing compositions that include a lipid component. A lipid component may include one type of lipid, or more than one type of lipid.

Lipids are fatty substances which may be naturally occurring or synthetic lipids. For example, lipids include the fatty droplets that naturally occur in the cytoplasm as well as the class of compounds which are well known to those of skill in the art which contain long-chain aliphatic hydrocarbons and their derivatives, such as fatty acids, alcohols, amines, amino alcohols, and aldehydes.

Some embodiments of the compositions of the present invention include liposomes. "Liposome" is a generic term encompassing a variety of unilamellar, multilamellar, and multivesicular lipid vehicles formed by the generation of enclosed lipid bilayers or aggregates. Liposomes may be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). However, the present invention also encompasses compositions that have different structures in solution than the normal vesicular structure. For example, the lipids may assume a micellar structure or merely exist as non-uniform aggregates of lipid molecules. Also contemplated are lipofectamine-nucleic acid complexes.

1. Neutral Liposomes

"Neutral liposomes or lipid composition" or "non-charged liposomes or lipid composition," as used herein, are defined as liposomes or lipid compositions having one or more lipids that yield an essentially-neutral, net charge (substantially non-charged). By "essentially neutral" or "essentially non-charged", it is meant that few, if any, lipids within a given population (e.g., a population of liposomes) include a charge that is not canceled by an opposite charge of another component (e.g., fewer than 10% of components include a non-canceled charge, more preferably fewer than 5%, and most preferably fewer than 1%). In certain embodiments of the present invention, a composition may be prepared wherein the lipid component of the composition is essentially neutral but is not in the form of liposomes.

In certain embodiments, neutral liposomes or lipid compositions may include mostly lipids and/or phospholipids that are themselves neutral. In certain embodiments, amphipathic lipids may be incorporated into or used to generate neutral liposomes or lipid compositions. For example, a neutral liposome may be generated by combining positively and negatively charged lipids so that those charges substantially cancel one another. For such a liposome, few, if any, charged lipids are present whose charge is not canceled by an oppositely-charged lipid (e.g., fewer than 10% of charged lipids have a charge that is not canceled, more preferably fewer than 5%, and most preferably fewer than 1%). It is also recognized that the above approach may be used to generate a neutral lipid composition wherein the lipid component of the composition is not in the form of liposomes.

2. Phospholipids

Lipid-containing compositions of the present invention may comprise phospholipids. In certain embodiments, a single kind or type of phospholipid may be used in the creation of lipid compositions such as liposomes (e.g., DOPC used to generate neutral liposomes). In other embodiments, more than one kind or type of phospholipid may be used.

Phospholipids include glycerophospholipids and certain sphingolipids. Phospholipids include, but are not limited to, dioleoylphosphatidylycholine ("DOPC"), egg phosphatidylcholine ("EPC"), dilauryloylphosphatidylcholine ("DLPC"), dimyristoylphosphatidylcholine ("DMPC"), dipalmitoylphosphatidylcholine ("DPPC"), distearoylphosphatidylcholine ("DSPC"), 1-myristoyl-2-palmitoyl phosphatidylcholine ("MPPC"), 1-palmitoyl-2-myristoyl phosphatidylcholine ("PMPC"), 1-palmitoyl-2-stearoyl phosphatidylcholine ("PSPC"), 1-stearoyl-2-palmitoyl phosphatidylcholine ("SPPC"), dilauryloylphosphatidylglycerol ("DLPG"), dimyristoylphosphatidylglycerol ("DMPG"), dipalmitoylphosphatidylglycerol ("DPPG"), distearoylphosphatidylglycerol ("DSPG"), distearoyl sphingomyelin ("DSSP"), distearoylphophatidylethanolamine ("DSPC"), dioleoylphosphatidylglycerol ("DOPG"), dimyristoyl phosphatidic acid ("DMPA"), dipalmitoyl phosphatidic acid ("DPPA"), dimyristoyl phosphatidylethanolamine ("DMPE"), dipalmitoyl phosphatidylethanolamine ("DPPE"), dimyristoyl phosphatidylserine ("DMPS"), dipalmitoyl phosphatidylserine ("DPPS"), brain phosphatidylserine ("BPS"), brain sphingomyelin ("BSP"), dipalmitoyl sphingomyelin ("DPSP"), dimyristyl phosphatidylcholine ("DMPC"), 1,2-distearoyl-sn-glycero-3-phosphocholine ("DAPC"), 1,2-diarachidoyl-sn-glycero-3-phosphocholine ("DBPC"), 1,2-dieicosenoyl-sn-glycero-3-phosphocholine ("DEPC"), dioleoylphosphatidylethanolamine ("DOPE"), palmitoyloeoyl phosphatidylcholine ("POPC"), palmitoyloeoyl phosphatidylethanolamine ("POPE"), lysophosphatidylcholine, lysophosphatidylethanolamine, and dilinoleoylphosphatidylcholine.

Phospholipids include, for example, phosphatidylcholines, phosphatidylglycerols, and phosphatidylethanolamines; because phosphatidylethanolamines and phosphatidyl cholines are non-charged under physiological conditions (i.e., at about pH 7), these compounds may be particularly useful for generating neutral liposomes. In certain embodiments, the phospholipid DOPC is used to produce non-charged liposomes or lipid compositions. In certain embodiments, a lipid that is not a phospholipid (e.g., a cholesterol) can also be used Phospholipids may be from natural or synthetic sources. However, phospholipids from natural sources, such as egg or soybean phosphatidylcholine, brain phosphatidic acid, brain or plant phosphatidylinositol, heart cardiolipin and plant or bacterial phosphatidylethanolamine are not used in certain embodiments as the primary phosphatide (i.e., constituting 50% or more of the total phosphatide composition) because this may result in instability and leakiness of the resulting liposomes.

3. Production of Liposomes

Liposomes and lipid compositions of the present invention can be made by different methods. For example, a nucleotide (e.g., siRNA) may be encapsulated in a neutral liposome using a method involving ethanol and calcium (Bailey and Sullivan, 2000). The size of the liposomes varies depending on the method of synthesis. A liposome suspended in an aqueous solution is generally in the shape of a spherical vesicle, and may have one or more concentric layers of lipid bilayer molecules. Each layer consists of a parallel array of molecules represented by the formula XY, wherein X is a hydrophilic moiety and Y is a hydrophobic moiety. In aqueous suspension, the concentric layers are arranged such that the hydrophilic moieties tend to remain in contact with an aqueous phase and the hydrophobic regions tend to self-associate. For example, when aqueous phases are present both within and without the liposome, the lipid molecules may form a bilayer, known as a lamella, of the arrangement XY-YX. Aggregates of lipids may form when the hydrophilic and hydrophobic parts of more than one lipid molecule become associated with each other. The size and shape of these aggregates will depend upon many different variables, such as the nature of the solvent and the presence of other compounds in the solution.

Lipids suitable for use according to the present invention can be obtained from commercial sources. For example, dimyristyl phosphatidylcholine ("DMPC") can be obtained from Sigma Chemical Co., dicetyl phosphate ("DCP") can be obtained from K & K Laboratories (Plainview, N.Y.); cholesterol ("Chol") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform may be used as the only solvent since it is more readily evaporated than methanol.

Liposomes within the scope of the present invention can be prepared in accordance with known laboratory techniques. In certain embodiments, liposomes are prepared by mixing liposomal lipids, in a solvent in a container (e.g., a glass, pear-shaped flask). The container will typically have a volume ten-times greater than the volume of the expected suspension of liposomes. Using a rotary evaporator, the solvent may be removed at approximately 40° C. under negative pressure. The solvent may be removed within about 5 minutes to 2 hours, depending on the desired volume of the liposomes. The composition can be dried further in a desiccator under vacuum. Dried lipids can be hydrated at approximately 25-50 mM phospholipid in sterile, pyrogen-free water by shaking until all the lipid film is resuspended. The aqueous liposomes can be then separated into aliquots, each placed in a vial, lyophilized and sealed under vacuum. Liposomes can also be prepared in accordance with other known laboratory procedures.

D. COMPOSITIONS

1. Combinations and Amounts of Ingredients

It is contemplated that the compositions of the present invention may include number of combinations of the polypeptides and nucleic acids disclosed throughout this specification. Additionally, the compositions can include any number of combinations of additional ingredients described throughout this specification. The concentrations of the polypeptides, nucleic acids, and additional ingredients can vary. In non-limiting embodiments, for example, the compositions can include in their final form, for example, at least about 0.0001%, 0.0002%, 0.0003%, 0.0004%, 0.0005%, 0.0006%, 0.0007%, 0.0008%, 0.0009%, 0.0010%, 0.0011%, 0.0012%, 0.0013%, 0.0014%, 0.0015%, 0.0016%, 0.0017%, 0.0018%, 0.0019%, 0.0020%, 0.0021%, 0.0022%, 0.0023%, 0.0024%, 0.0025%, 0.0026%, 0.0027%, 0.0028%, 0.0029%, 0.0030%, 0.0031%, 0.0032%, 0.0033%, 0.0034%, 0.0035%, 0.0036%, 0.0037%, 0.0038%, 0.0039%, 0.0040%, 0.0041%, 0.0042%, 0.0043%, 0.0044%, 0.0045%, 0.0046%, 0.0047%, 0.0048%, 0.0049%, 0.0050%, 0.0051%, 0.0052%, 0.0053%, 0.0054%, 0.0055%, 0.0056%, 0.0057%, 0.0058%, 0.0059%, 0.0060%, 0.0061%, 0.0062%, 0.0063%, 0.0064%, 0.0065%, 0.0066%, 0.0067%, 0.0068%, 0.0069%, 0.0070%, 0.0071%, 0.0072%, 0.0073%, 0.0074%, 0.0075%, 0.0076%, 0.0077%, 0.0078%, 0.0079%, 0.0080%, 0.0081%, 0.0082%, 0.0083%, 0.0084%, 0.0085%, 0.0086%, 0.0087%, 0.0088%, 0.0089%, 0.0090%, 0.0091%, 0.0092%, 0.0093%, 0.0094%, 0.0095%, 0.0096%, 0.0097%, 0.0098%, 0.0099%, 0.0100%, 0.0200%, 0.0250%, 0.0275%, 0.0300%, 0.0325%, 0.0350%, 0.0375%, 0.0400%, 0.0425%, 0.0450%, 0.0475%, 0.0500%, 0.0525%, 0.0550%, 0.0575%, 0.0600%, 0.0625%, 0.0650%, 0.0675%, 0.0700%, 0.0725%, 0.0750%, 0.0775%, 0.0800%, 0.0825%, 0.0850%, 0.0875%, 0.0900%, 0.0925%, 0.0950%, 0.0975%, 0.1000%, 0.1250%, 0.1500%, 0.1750%, 0.2000%, 0.2250%, 0.2500%, 0.2750%, 0.3000%, 0.3250%, 0.3500%, 0.3750%, 0.4000%, 0.4250%, 0.4500%, 0.4750%, 0.5000%, 0.5250%, 0.550%, 0.5750%, 0.6000%, 0.6250%, 0.6500%, 0.6750%, 0.7000%, 0.7250%, 0.7500%, 0.7750%, 0.8000%, 0.8250%, 0.8500%, 0.8750%, 0.9000%, 0.9250%, 0.9500%, 0.9750%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 60%, 65%, 70%, 75%, 80%, 85%, 90%, 95%, or 99% or more, or any range or integer derivable therein, of at least one of the polypeptides, nucleic acids, or other ingredients. In non-limiting aspects, the percentage of such ingredients can be calculated by weight or volume of the total weight of the compositions. The concentrations can vary depending on the desired effect of the compositions or on the product into which the compositions are incorporated.

2. Composition Vehicles

The compositions of the present invention can be formulated into all types of vehicles. Non-limiting examples of suitable vehicles include emulsions (e.g., water-in-oil, water-in-oil-in-water, oil-in-water, oil-in-water-in-oil, oil-in-water-in-silicone emulsions), creams, lotions, solutions (both aqueous and hydro-alcoholic), anhydrous bases (such as lip sticks, powders), gels, and ointments or by other method or any combination of the forgoing as would be known to one of ordinary skill in the art. Variations and other appropriate vehicles will be apparent to the skilled artisan and are appropriate for use in the present invention. In certain aspects, the concentrations and combinations of the ingredients be selected in such a way that the combinations are chemically compatible and do not form complexes which precipitate from the finished product.

It is also contemplated that the polypeptides and polynucleotides of the present invention and additional ingredients identified throughout this specification can be encapsulated for delivery to a target area such as skin. Non-limiting examples of encapsulation techniques include the use of liposomes, vesicles, and/or nanoparticles (e.g., biodegradable and non-biodegradable colloidal particles comprising polymeric materials in which the ingredient is trapped, encapsulated, and/or absorbed—examples include nanospheres, nanocapsules, and liposomes) that can be used as delivery vehicles to deliver such ingredients to skin (see, e.g., U.S. Pat. Nos. 6,387,398; 6,203,802; 5,411,744).

Also contemplated are pharmaceutically-acceptable or pharmacologically-acceptable compositions. The phrase "pharmaceutically-acceptable" or "pharmacologically-acceptable" includes compositions that do not produce an allergic or similar untoward reaction when administered to a human. Typically, such compositions are prepared either as topical compositions, liquid solutions or suspensions, solid forms suitable for solution in, or suspension in, liquid prior to use can also be prepared. Routes of administration can vary with the location and nature of the condition to be treated, and include, e.g., topical, inhalation, intradermal, transdermal, parenteral, intravenous, intramuscular, intranasal, subcutaneous, percutaneous, intratracheal, intraperitoneal, intratumoral, perfusion, lavage, direct injection, and oral administration and formulation.

3. Products

The compositions of the present invention can be incorporated into products. Non-limiting examples of products include skin care products, cosmetic products, food-based products, pharmaceutical products, etc. By way of example only, non-limiting skin care products include sunscreen products, sunless skin tanning products, hair products, fingernail products, moisturizing creams, moisturizing lotions, skin benefit creams and lotions, softeners, day lotions, gels, ointments, lipsticks, or other known skin care products or applications. Additionally, the cosmetic products can be formulated as leave-on or rinse-off products.

4. Additional Ingredients

Compositions of the present invention can optionally include additional ingredients. Non-limiting examples of additional ingredients include pharmaceutical ingredients and cosmetic ingredients (both active and non-active).

a. Pharmaceutical Ingredients

Pharmaceutical ingredients are also contemplated as being useful with the compositions of the present invention. Non-limiting examples of pharmaceutical ingredients include analgesics, anesthetics, antihistamines, anti-inflammatory agents including non-steroidal anti-inflammatory drugs, antibiotics, antifungals, antivirals, antimicrobials, anti-cancer actives, scabicides, pediculicides, antineoplastics, antiperspirants, antipruritics, antipsoriatic agents, antiseborrheic agents, biologically active proteins and peptides, burn treatment agents, cauterizing agents, depigmenting agents, depilatories, diaper rash treatment agents, enzymes, hair growth stimulants, hair growth retardants including DFMO and its salts and analogs, hemostatics, kerotolytics, canker sore treatment agents, cold sore treatment agents, dental and periodontal treatment agents, photosensitizing actives, skin protectant/barrier agents, steroids including hormones and corticosteroids, sunburn treatment agents, sunscreens, transdermal actives, nasal actives, vaginal actives, wart treatment agents, wound treatment agents, wound healing agents, etc.

Other pharmaceutical agents contemplated for inclusion in the compositions of the present invention include agents that can be applied in the treatment of ichthyosis vulgaris and atopic dermatitis. Examples include alpha hydroxy acids such as lactic and glycolic acid, retinoids, other vitamin A derivatives, calcineurin inhibitors, cyclosporine, interferon gamma-1b, or a topical or oral corticosteroid.

b. Cosmetic Ingredients

The CTFA International Cosmetic Ingredient Dictionary and Handbook (2004) describes a wide variety of non-limiting cosmetic ingredients that can be used in the context of the present invention. Examples of these ingredient classes include: fragrances (artificial and natural), dyes and color ingredients (e.g., Blue 1, Blue 1 Lake, Red 40, titanium dioxide, D&C blue no. 4, D&C green no. 5, D&C orange no. 4, D&C red no. 17, D&C red no. 33, D&C violet no. 2, D&C yellow no. 10, and D&C yellow no. 11), adsorbents, emulsifiers, stabilizers, lubricants, solvents, moisturizers (including, e.g., emollients, humectants, film formers, occlusive agents, and agents that affect the natural moisturization mechanisms of the skin), exfoliating agents, water-repellants, UV absorbers (physical and chemical absorbers such as paraaminobenzoic acid ("PABA") and corresponding PABA derivatives, titanium dioxide, zinc oxide, etc.), essential oils, vitamins (e.g., A, B, C, D, E, and K), trace metals (e.g., zinc, calcium and selenium), anti-irritants (e.g., steroids and non-steroidal anti-inflammatories), botanical extracts (e.g., aloe vera, chamomile, cucumber extract, *Ginkgo biloba, ginseng,* and rosemary), anti-microbial agents, antioxidants (e.g., BHT and tocopherol), chelating agents (e.g., disodium EDTA and tetrasodium EDTA), preservatives (e.g., methylparaben and propylparaben), pH adjusters (e.g., sodium hydroxide and citric acid), absorbents (e.g., aluminum starch octenylsuccinate, kaolin, corn starch, oat starch, cyclodextrin, talc, and zeolite), skin bleaching and lightening agents (e.g., hydroquinone and niacinamide lactate), humectants (e.g., glycerin, propylene glycol, butylene glycol, pentylene glycol, sorbitol, urea, and manitol), exfoliants (e.g., alpha-hydroxyacids, and beta-hydroxyacids such as lactic acid, glycolic acid, and salicylic acid; and salts thereof) waterproofing agents (e.g., magnesium/aluminum hydroxide stearate), skin conditioning agents (e.g., aloe extracts, allantoin, bisabolol, ceramides, dimethicone, hyaluronic acid, and dipotassium glycyrrhizate), thickening agents (e.g., substances which that can increase the viscosity of a composition such as carboxylic acid polymers, cross-linked polyacrylate polymers, polyacrylamide polymers, polysaccharides, and gums), and silicone containing compounds (e.g., silicone oils and polyorganosiloxanes).

E. DISEASES TO BE TREATED OR PREVENTED

The diseases or disorders contemplated for treatment or prevention using the polynucleotides and polypeptides of the present invention include any disease or disorder where increase in intracellular filaggrin is known or suspected to be of benefit. Non-limiting examples of such diseases include diseases or disorders of the skin. The disease or disorder may be dry skin, peeling skin, scaling skin, inflamed skin, cracked skin, chapped skin, acne, calluses, corns, canker sores, carbuncles, cellulitis, cold sores, dandruff, dermatitis, eczema, atopic dermatitis, contact dermatitis, seborrhoeic dermatitis, cradle cap, nummular dermatitis, stasis dermatitis, perioral dermatitis, dermatitis herpetiformis, epidermolysis bullosa, erythrasma, erysipelas, folliculitis, herpes infection, impetigo, ichthyosis, hyperhidrosis, jock itch, keloid, keratoacanthoma, actinic keratosis, keratosis pilaris, seborrheic keratosis, hyperkeratosis, lichen planus, pemphigus, photosensitivity, *pityriasis rosea,* psoriasis, rosacea, scabies, scleroderma, sebacious cyst, shingles, basal cell carcinoma, squamous cell carcinoma, and warts.

F. KITS

Kits are also contemplated as being used in certain aspects of the present invention. For instance, a polypeptide or nucleic acid of the present invention can be included in a kit. A kit can include a sealed container. Non-limiting examples of containers include a bottle, a metal tube, a laminate tube, a plastic tube, a dispenser, a pressurized container, a barrier container, a package, a compartment, a lipstick container, a compact container, cosmetic pans that can hold cosmetic compositions, or other types of containers such as injection or blow-molded plastic containers into which the dispersions or compositions or desired bottles, dispensers, or packages are retained. Other examples of containers include glass or plastic vials or bottles. The kit and/or container can include indicia on its surface. The indicia, for example, can be a word, a phrase, an abbreviation, a picture, or a symbol.

The containers can dispense a pre-determined amount of a composition of the present invention. In other embodiments, the container can be squeezed (e.g., metal, laminate, or plastic tube) to dispense a desired amount of the composition. The composition can be dispensed as a spray, an aerosol, a liquid, a fluid, or a semi-solid. The containers can have spray, pump, or squeeze mechanisms. A kit can also include instructions for using the kit and/or compositions. Instructions can include an explanation of how to apply, administer, use, and maintain the compositions.

G. COMBINATION TREATMENTS

In order to increase the effectiveness of polypeptide of the present invention, or expression construct coding therefor, it may be desirable to combine these compositions with other agents effective in the treatment or prevention of a disease or disorder where a filaggrin polypeptide may be of benefit. For example, the chimeric polypeptides of the present invention can be administered in conjunction with other treatment of a skin disease such as atopic dermatitis or ichthyosis vulgaris. Non-limiting examples of these diseases or conditions are as set forth above.

The therapy may precede or follow the other agent treatment by intervals ranging from minutes to weeks. The therapies may be administered concurrently. In embodiments where the second therapy is applied separately, one would generally ensure that a significant period of time did not expire between the time of each delivery, such that the two therapies would still be able to exert an advantageously combined effect on the cell. In such instances, it is contemplated that one may administer both therapies within about 12-24 h of each other and, more preferably, within about 6-12 h of each other. In some situations, it may be desirable to extend the time period for treatment significantly, however, where several d (2, 3, 4, 5, 6 or 7) to several wk (1, 2, 3, 4, 5, 6, 7 or 8) lapse between the respective administrations.

Various combinations may be employed, the polypeptide or polynucleotide of the present invention is "A" and the secondary agent is "B":

| | | | | | |
|---|---|---|---|---|---|
| A/B/A | B/A/B | B/B/A | A/A/B | A/B/B | B/A/A |
| A/B/B/B | B/A/B/B | B/B/B/A | B/B/A/B | A/A/B/B | A/B/A/B |
| A/B/B/A | B/B/A/A | B/A/B/A | B/A/A/B | A/A/A/B | B/A/A/A |
| A/B/A/A | A/A/B/A | | | | |

Administration of therapeutic agents and compositions of the present invention to a subject will follow general protocols for the administration of therapeutic agents, taking into account the toxicity, if any. It is expected that the treatment cycles would be repeated as necessary. It also is contemplated that various standard therapies may be applied in combination with the polypeptides and polynucleotides of the present invention. Non-limiting examples include the pharmaceutical agents set forth above. Other examples include procedures such as dermabrasion, laser therapy, laser resurfacing, ultraviolet treatment, and skin grafting.

H. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Treatment of Mouse Skin with Recombinant Filaggrin

The FLG protein was isolated, and several FLG peptides, consisting of partial or complete repeat regions, were created. These proteins were modified to contain a cell importation signal (made up of arginine methionine repeats—the "RMR" tag) that has been successfully employed to drive protein internalization by cells. The proteins that were synthesized include (1) human FLG with RMR tag; (2) mouse FLG with RMR tag; and (3) mouse FLG without RMR tag.

Multiple immunohistochemistry (IHC) experiments were performed to determine whether FLG with the RMR tag can be taken up by HEK 293 cells, a cell line derived from embryonic kidney cells. In these experiments, mouse FLG protein both with and without RMR importation signal were applied to HEK 293 cells at varying concentrations over varying time points. The FLG proteins were then stained with a FITC fluorescence stain and photographed under an Olympus IX81 confocal microscope. Preliminary staining experiments showed that FLG with the RMR tag are internalized into HEK 293 cells to a greater extent than FLG without the tag. In particular, MuFLG with RMR was shown to enter the cell at a higher rate than MuFLG without RMR after 4.5 hours observed and documented by imaging using an Olympus IX81 camera at 40×. While FLG without RMR are still taken up by the cells to a certain extent, possibly due to passive importation, higher fluorescence was found with the RMR tag than without it. Immunohistochemical staining showed that while FLG plus RMR is internalized, it remains in the cytoplasm. HEK 293 cells stained with FITC (green for FLG) and DAPI (blue for nucleus) staining showed that FLG+RMR enters the cell but is absent in the nucleus after 1 hour, thus documenting the robust internalization of FLG-RMR and its localization in the cytoplasm. It is worth noting that active FLG protein (RMR$^-$) is expressed in the cytoplasm yet absence from the nucleus in vivo.

Further studies are being conducted to examine the proteins on mouse and human keratinocyte cell lines. Cell lines being prepared include reconstructed human epidermis (RHE), a human derived keratinocyte polymer and mouse CL-177 keratinocytes. By techniques such as protein immunoblotting and immunohistochemistry, we will determine the amount and localization of FLG. To certify that FLG importation and expression can be duplicated in vivo testing of these proteins on mice is necessary.

To date, the FLG-RMR protein, mixed with a carrier solution (in this case, ABSORBASE cream), were tested on a flaky tail (ft) mouse model, a mouse model lacking the normal high molecular profilaggrin and cleaved filaggrin proteins resulting in dry, flaky skin. Initial experiments tested the efficiency of delivery and importation of the produced FLG-RMR peptides on flaky tail and normal C57Bl mice. The hair was shaved from the side of each mouse and FLG-RMR protein with carrier cream was applied. Twenty four hours after application of protein-carrier cream mixture, the treated skin area was biopsied and analyzed for changes in dermal layer phenotype and presence of FLG-RMR protein. Frozen sections from treated skin indicate that clear differences exist between the treated and untreated skin with the FLG-RMR protein as compared to the control.

Future experiments will include testing other carrier solutions and various concentrations of FLG-RMR at multiple time points to determine optimal conditions, and an experimental trial will be conducted. In this trial, flaky tail mice will be divided into four cohorts: (1) carrier with FLG protein and RMR tag; (2) carrier with FLG protein without RMR tag; (3) carrier only; (4) carrier with denatured protein and RMR tag. There will be five mice per cohort and the respective treatments will be applied on the tail, a shaved area of skin, and an unshaved area of skin after the mice have reached P60-P90. Various time points after the treatments have been applied, mice will be euthanized and dermal punch biopsies will be taken from each mouse. Immunoblotting experiments will be conducted to determine the amount of protein intake. By showing that FLG protein can be delivered via a carrier vehicle in a mouse model, clinical trials in humans are contemplated.

All of the methods disclosed and claimed herein can be made and executed without undue experimentation in light of the present disclosure. While the methods of this invention have been described in terms of preferred embodiments, it will be apparent to those of skill in the art that variations may be applied to the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,215,051
U.S. Pat. No. 4,554,101
U.S. Pat. No. 4,659,774
U.S. Pat. No. 4,682,195
U.S. Pat. No. 4,683,202
U.S. Pat. No. 4,816,571
U.S. Pat. No. 4,946,778

U.S. Pat. No. 4,959,463
U.S. Pat. No. 5,141,813
U.S. Pat. No. 5,214,136
U.S. Pat. No. 5,223,618
U.S. Pat. No. 5,264,566
U.S. Pat. No. 5,378,825
U.S. Pat. No. 5,411,744
U.S. Pat. No. 5,428,148
U.S. Pat. No. 5,446,137
U.S. Pat. No. 5,466,786
U.S. Pat. No. 5,470,967
U.S. Pat. No. 5,554,744
U.S. Pat. No. 5,574,146
U.S. Pat. No. 5,602,240
U.S. Pat. No. 5,602,244
U.S. Pat. No. 5,610,289
U.S. Pat. No. 5,614,617
U.S. Pat. No. 5,623,070
U.S. Pat. No. 5,645,897
U.S. Pat. No. 5,652,099
U.S. Pat. No. 5,670,663
U.S. Pat. No. 5,672,697
U.S. Pat. No. 5,681,947
U.S. Pat. No. 5,700,922
U.S. Pat. No. 5,705,629
U.S. Pat. No. 5,708,154
U.S. Pat. No. 5,714,606
U.S. Pat. No. 5,763,167
U.S. Pat. No. 5,777,092
U.S. Pat. No. 5,792,847
U.S. Pat. No. 5,858,988
U.S. Pat. No. 5,859,221
U.S. Pat. No. 5,872,232
U.S. Pat. No. 5,886,165
U.S. Pat. No. 5,889,155
U.S. Pat. No. 5,908,845
U.S. Pat. No. 6,203,802
U.S. Pat. No. 6,387,398
Altschul et al., *Nucleic Acids Res.*, 25:3389-3402, 1997.
Bailey and Sullivan, *Biochimica. Biophys. Acts.*, 239-252, 2000.
Bird et al., *Science*, 242:423-426, 1988.
Bittner et al., *Methods in Enzymol*, 153:516-544, 1987.
Bodanszky et al., *J. Antibiot.*, 29(5):549-53, 1976.
Brinkmann and Pastan, *Biochim. Biophys. Acta*, 1198(1):27-45, 1994.
Caruthers et al., *Nucleic Acids Symp. Ser.*, (7):215-223, 1980.
Chaudhary et al., *Proc. Natl. Acad. Sci. USA*, 87(3):1066-1070, 1990.
Chow and Kempe, *Nucleic Acids Res.*, 9(12):2807-2817, 1981.
Colbere-Garapin et al., *J. Mol. Biol.*, 150:1-14, 1981.
Cole et al., *J. Immunol. Methods*, 78(2):271-278, 1985.
Cote et al., *Proc. Natl. Acad. Sci. USA*, 80(7):2026-2030, 1983.
Crea and Horn, *Nucleic Acids Res.*, 8(10):2331-2348, 1980.
Creighton, In: *Proteins Structures And Molecular Principles*, W.H. Freeman and Co., N.Y. 50-60, 1983.
CTFA International Cosmetic Ingredient Dictionary and Handbook, 2004.
Datar et al., *Nucleic Acids Res.*, 21(3):439-446, 1993.
EP 266,032
Froehler et al., *Nucleic Acids Res.*, 14:5399-5407, 1986.
Ghosh and Bachhawat, In: *Liver Diseases, Targeted Diagnosis and Therapy Using Specific Receptors and Ligands*, Wu et al. (Eds.), Marcel Dekker, NY, 87-104, 1991.
Hartman and Mulligan, *Proc. Natl. Acad. Sci. USA*, 85:8047-8051, 1988.
Hoffjan, *Br. J. Dermatol.*, 157(3):441-9, 2007.
Huston et al., *Biochemistry*, 27(25):8945-8952, 1988.
Kohler and Milstein, *Nature*, 256:495-497, 1975.
Kornberg and Baker, In: *DNA Replication*, 2d Ed., Freeman, San Francisco, 1992.
Kyte and Doolittle, *J. Mol. Biol.*, 157(1):105-132, 1982.
Lowy et al., *Cell*, 22:817-823, 1980.
McConlogue, *Mol. Cell Biol.*, 6(8):2865-2871, 1986.
Morrison et al., *Proc. Natl. Acad. Sci. USA*, 81(21):6851-6855, 1984.
Mulligan and Berg, *Proc. Natl. Acad. Sci. USA*, 78(4):2072-2076, 1981.
Neuberger et al., *Nature*, 312(5995):604-608, 1984.
O'Hare et al., *Proc. Natl. Acad. Sci. USA*, 78: 1527, 1981.
Patent Publn. 2003/0124553
Ruther et al., *EMBO J.*, 2(10):1791-1794, 1983.
Sambrook and Russell, Molecular Cloning: A Laboratory Manual 3$^{rd}$ Ed., Cold Spring Harbor Laboratory Press, 2001.
Santerre et al., *Gene*, 30: 147-156, 1984.
Smith et al., *Gene*, 25(1):21-8, 1983.
Szybalski and Szybalski, *Proc. Natl. Acad. Sci. USA*, 48:2026-2034, 1962.
Takeda et al., *Nature*, 314(6010):452-454, 1985.
Van Heeke and Schuster, *J. Biol. Chem.*, 264(33):19475-19477, 1989.
Wigler et al., *Cell*, 11(1):223-232, 1977.
Wigler et al., *Proc. Natl. Acad. Sci. USA*, 77(6):3567-3570, 1980.

The invention claimed is:

1. A recombinant polypeptide comprising (a) a filaggrin amino acid sequence selected from the group consisting of SEQ ID NOs 1-19; and (b) a cell importation signal sequence selected from the group consisting of SEQ ID NOs 23-38.

2. The polypeptide of claim 1, wherein the filaggrin amino acid sequence comprises SEQ ID NO:1.

3. The polypeptide of claim 1, wherein the cell importation signal sequence comprises the amino acid sequence of RM or MR.

4. The polypeptide of claim 1, wherein the cell importation signal sequence comprises SEQ ID NO:23.

5. The polypeptide of claim 1, wherein the polypeptide comprises SEQ ID NO:21 or SEQ ID NO:22.

6. The polypeptide of claim 5, wherein the polypeptide consists of SEQ ID NO:21 or SEQ ID NO:22.

7. The polypeptide of claim 1, wherein the polypeptide is further defined as a fusion protein of the filaggrin amino acid sequence and the cell importation amino acid sequence.

8. The polypeptide of claim 1, wherein the filaggrin amino acid sequence is attached to the N-terminus of the cell importation signal sequence.

9. The polypeptide of claim 1, wherein the filaggrin amino acid sequence is attached to the C-terminus of the cell importation signal sequence.

10. A skin-care composition comprising an effective amount of a polypeptide as set forth in claim 1.

11. The composition of claim 10, comprising a lipid component.

12. The composition of claim 11, wherein the lipid component comprises a phospholipid.

13. The composition of claim 10, wherein the composition is a solution, an emulsion, a cream, a lotion, a gel, or an ointment.

14. The composition of claim 13, wherein the emulsion is an oil-in-water emulsion or a water-in-oil emulsion.

15. The composition of claim 10, wherein the composition comprises from about 0.001% to about 5.0% by weight of polypeptide.

16. A nucleic acid comprising a nucleic acid sequence encoding a polypeptide as set forth in claim 1.

17. A pharmaceutical composition comprising a polypeptide as set forth in claim 1.

18. A kit comprising a sealed container comprising a recombinant polypeptide as set forth in claim 1 or pharmaceutical composition of claim 17.

19. The kit of claim 18, wherein the sealed container is a vial, a bottle, a dispenser, or a package.

20. The kit of claim 18, further comprising an applicator.

* * * * *

SEQUENCE LISTING

<160> NUMBER OF SEQ ID NOS: 41

<210> SEQ ID NO 1
<211> LENGTH: 344
<212> TYPE: PRT
<213> ORGANISM: Homo sapiens

<400> SEQUENCE: 1

Arg Ser Gly Glu Thr Ser Gly Arg Ser Gly Ser Phe Leu Tyr Gln Val
1               5                   10                  15

Ser Thr His Glu Gln Ser Glu Ser Thr His Gly Gln Thr Ala Pro Ser
            20                  25                  30

-continued

Thr Gly Gly Arg Gln Gly Ser Arg His Glu Gln Ala Arg Asn Ser Ser
        35                  40                  45

Arg His Ser Ala Ser Gln Asp Gly Gln Asp Thr Ile Arg Gly His Pro
    50                  55                  60

Gly Ser Ser Arg Gly Arg Gln Gly Ser Tyr His Glu Gln Ser Val
65                  70                  75                  80

Asp Arg Ser Gly His Ser Gly Tyr His His Ser His Thr Thr Pro Gln
                85                  90                  95

Gly Arg Ser Asp Ala Ser His Gly Gln Ser Gly Pro Arg Ser Ala Ser
            100                 105                 110

Arg Gln Thr Arg Asn Glu Glu Gln Ser Gly Asp Gly Ser Arg His Ser
        115                 120                 125

Gly Ser Arg His His Glu Pro Ser Thr Arg Ala Gly Ser Ser Arg His
    130                 135                 140

Ser Gln Val Gly Gln Gly Glu Ser Ala Gly Ser Lys Thr Ser Arg Arg
145                 150                 155                 160

Gln Gly Ser Ser Val Ser Gln Asp Arg Asp Ser Glu Gly His Ser Glu
                165                 170                 175

Asp Ser Glu Arg Arg Ser Glu Ser Ala Ser Arg Asn His Tyr Gly Ser
            180                 185                 190

Ala Arg Glu Gln Ser Arg His Gly Ser Arg Asn Pro Arg Ser His Gln
        195                 200                 205

Glu Asp Arg Ala Ser His Gly His Ser Ala Glu Ser Ser Arg Gln Ser
    210                 215                 220

Gly Thr Arg His Ala Glu Thr Ser Ser Gly Gly Gln Ala Ala Ser Ser
225                 230                 235                 240

Gln Glu Gln Ala Arg Ser Ser Pro Gly Glu Arg His Gly Ser Arg His
                245                 250                 255

Gln Gln Ser Ala Asp Ser Ser Thr Asp Ser Gly Thr Gly Arg Arg Gln
            260                 265                 270

Asp Ser Ser Val Val Gly Asp Ser Gly Asn Arg Gly Ser Ser Gly Ser
        275                 280                 285

Gln Ala Ser Asp Ser Glu Gly His Ser Glu Glu Ser Asp Thr Gln Ser
    290                 295                 300

Val Ser Ala His Gly Gln Ala Gly Pro His Gln Gln Ser His Gln Glu
305                 310                 315                 320

Ser Thr Arg Gly Gln Ser Gly Glu Arg Ser Gly Arg Ser Gly Ser Phe
                325                 330                 335

Tyr Gln Val Ser Thr His Glu Gln
            340

<210> SEQ ID NO 2
<211> LENGTH: 4061
<212> TYPE: PRT
<213> ORGANISM: Homo sapiens

<400> SEQUENCE: 2

Met Ser Thr Leu Leu Glu Asn Ile Phe Ala Ile Ile Asn Leu Phe Lys
1               5                   10                  15

Gln Tyr Ser Lys Lys Asp Lys Asn Thr Asp Thr Leu Ser Lys Lys Glu
                20                  25                  30

Leu Lys Glu Leu Leu Glu Lys Glu Phe Arg Gln Ile Leu Lys Asn Pro
            35                  40                  45

Asp Asp Pro Asp Met Val Asp Val Phe Met Asp His Leu Asp Ile Asp
        50                  55                  60

```
His Asn Lys Lys Ile Asp Phe Thr Glu Phe Leu Leu Met Val Phe Lys
 65                  70                  75                  80

Leu Ala Gln Ala Tyr Tyr Glu Ser Thr Arg Lys Glu Asn Leu Pro Ile
                 85                  90                  95

Ser Gly His Lys His Arg Lys His Ser His His Asp Lys His Glu Asp
            100                 105                 110

Asn Lys Gln Glu Glu Asn Lys Glu Asn Arg Lys Arg Pro Ser Ser Leu
            115                 120                 125

Glu Arg Arg Asn Asn Arg Lys Gly Asn Lys Gly Arg Ser Lys Ser Pro
130                 135                 140

Arg Glu Thr Gly Gly Lys Arg His Glu Ser Ser Glu Lys Lys Glu
145                 150                 155                 160

Arg Lys Gly Tyr Ser Pro Thr His Arg Glu Glu Glu Tyr Gly Lys Asn
                165                 170                 175

His His Asn Ser Ser Lys Lys Glu Lys Asn Lys Thr Glu Asn Thr Arg
            180                 185                 190

Leu Gly Asp Asn Arg Lys Arg Leu Ser Glu Arg Leu Glu Glu Lys Glu
            195                 200                 205

Asp Asn Glu Glu Gly Val Tyr Asp Tyr Glu Asn Thr Gly Arg Met Thr
210                 215                 220

Gln Lys Trp Ile Gln Ser Gly His Ile Ala Thr Tyr Tyr Thr Ile Gln
225                 230                 235                 240

Asp Glu Ala Tyr Asp Thr Thr Asp Ser Leu Leu Glu Glu Asn Lys Ile
                245                 250                 255

Tyr Glu Arg Ser Arg Ser Ser Asp Gly Lys Ser Ser Ser Gln Val Asn
                260                 265                 270

Arg Ser Arg His Glu Asn Thr Ser Gln Val Pro Leu Gln Glu Ser Arg
            275                 280                 285

Thr Arg Lys Arg Arg Gly Ser Arg Val Ser Gln Asp Arg Asp Ser Glu
            290                 295                 300

Gly His Ser Glu Asp Ser Glu Arg His Ser Gly Ser Ala Ser Arg Asn
305                 310                 315                 320

His His Gly Ser Ala Trp Glu Gln Ser Arg Asp Gly Ser Arg His Pro
                325                 330                 335

Arg Ser His Asp Glu Asp Arg Ala Ser His Gly His Ser Ala Asp Ser
                340                 345                 350

Ser Arg Gln Ser Gly Thr Arg His Ala Glu Thr Ser Ser Arg Gly Gln
            355                 360                 365

Thr Ala Ser Ser His Glu Gln Ala Arg Ser Ser Pro Gly Glu Arg His
            370                 375                 380

Gly Ser Gly His Gln Gln Ser Ala Asp Ser Ser Arg His Ser Ala Thr
385                 390                 395                 400

Gly Arg Gly Gln Ala Ser Ser Ala Val Ser Asp Arg Gly His Arg Gly
                405                 410                 415

Ser Ser Gly Ser Gln Ala Ser Asp Ser Glu Gly His Ser Glu Asn Ser
            420                 425                 430

Asp Thr Gln Ser Val Ser Gly His Gly Lys Ala Gly Leu Arg Gln Gln
            435                 440                 445

Ser His Gln Glu Ser Thr Arg Gly Arg Ser Gly Glu Arg Ser Gly Arg
            450                 455                 460

Ser Gly Ser Ser Leu Tyr Gln Val Ser Thr His Glu Gln Pro Asp Ser
465                 470                 475                 480
```

-continued

Ala His Gly Arg Thr Gly Thr Ser Thr Gly Gly Arg Gln Gly Ser His
                    485                 490                 495

His Glu Gln Ala Arg Asp Ser Ser Arg His Ser Ala Ser Gln Glu Gly
                500                 505                 510

Gln Asp Thr Ile Arg Gly His Pro Gly Ser Ser Arg Gly Gly Arg Gln
                515                 520                 525

Gly Ser His His Glu Gln Ser Val Asn Arg Ser Gly His Ser Gly Ser
            530                 535                 540

His His Ser His Thr Thr Ser Gln Gly Arg Ser Asp Ala Ser His Gly
545                 550                 555                 560

Gln Ser Gly Ser Arg Ser Ala Ser Arg Gln Thr Arg Asn Glu Glu Gln
                565                 570                 575

Ser Gly Asp Gly Thr Arg His Ser Gly Ser Arg His His Glu Ala Ser
                580                 585                 590

Ser Gln Ala Asp Ser Ser Arg His Ser Gln Val Gly Gln Gly Gln Ser
            595                 600                 605

Ser Gly Pro Arg Thr Ser Arg Asn Gln Gly Ser Ser Val Ser Gln Asp
        610                 615                 620

Ser Asp Ser Gln Gly His Ser Glu Asp Ser Glu Arg Trp Ser Gly Ser
625                 630                 635                 640

Ala Ser Arg Asn His His Gly Ser Ala Gln Glu Gln Ser Arg Asp Gly
                645                 650                 655

Ser Arg His Pro Arg Ser His His Glu Asp Arg Ala Gly His Gly His
                660                 665                 670

Ser Ala Asp Ser Ser Arg Lys Ser Gly Thr Arg His Thr Gln Asn Ser
            675                 680                 685

Ser Ser Gly Gln Ala Ala Ser Ser His Glu Gln Ala Arg Ser Ser Ala
            690                 695                 700

Gly Glu Arg His Gly Ser Arg His Gln Leu Gln Ser Ala Asp Ser Ser
705                 710                 715                 720

Arg His Ser Gly Thr Gly His Gly Gln Ala Ser Ser Ala Val Arg Asp
                725                 730                 735

Ser Gly His Arg Gly Ser Ser Gly Ser Gln Ala Thr Asp Ser Glu Gly
                740                 745                 750

His Ser Glu Asp Ser Asp Thr Gln Ser Val Ser Gly His Gly Gln Ala
            755                 760                 765

Gly His His Gln Gln Ser His Gln Glu Ser Ala Arg Asp Arg Ser Gly
            770                 775                 780

Glu Arg Ser Arg Arg Ser Gly Ser Phe Leu Tyr Gln Val Ser Thr His
785                 790                 795                 800

Lys Gln Ser Glu Ser Ser His Gly Trp Thr Gly Pro Ser Thr Gly Val
                805                 810                 815

Arg Gln Gly Ser His His Glu Gln Ala Arg Asp Asn Ser Arg His Ser
                820                 825                 830

Ala Ser Gln Asp Gly Gln Asp Thr Ile Arg Gly His Pro Gly Ser Ser
                835                 840                 845

Arg Arg Gly Arg Gln Gly Ser His His Glu Gln Ser Val Asp Arg Ser
            850                 855                 860

Gly His Ser Gly Ser His Ser His Thr Thr Ser Gln Gly Arg Ser
865                 870                 875                 880

Asp Ala Ser Arg Gly Gln Ser Gly Ser Arg Ser Ala Ser Arg Thr Thr
                885                 890                 895

Arg Asn Glu Glu Gln Ser Arg Asp Gly Ser Arg His Ser Gly Ser Arg

-continued

```
                900             905             910
His His Glu Ala Ser Ser His Ala Asp Ile Ser Arg His Ser Gln Ala
            915             920             925
Gly Gln Gly Gln Ser Glu Gly Ser Arg Thr Ser Arg Arg Gln Gly Ser
        930             935             940
Ser Val Ser Gln Asp Ser Asp Ser Glu Gly His Ser Glu Asp Ser Glu
945             950             955             960
Arg Trp Ser Gly Ser Ala Ser Arg Asn His Arg Gly Ser Ala Gln Glu
            965             970             975
Gln Ser Arg His Gly Ser Arg His Pro Arg Ser His His Glu Asp Arg
        980             985             990
Ala Gly His Gly His Ser Ala Asp Ser Ser Arg Gln Ser Gly Thr Pro
    995             1000            1005
His Ala Glu Thr Ser Ser Gly Gly Gln Ala Ala Ser Ser His Glu
    1010            1015            1020
Gln Ala Arg Ser Ser Pro Gly Glu Arg His Gly Ser Arg His Gln
    1025            1030            1035
Gln Ser Ala Asp Ser Ser Arg His Ser Gly Ile Pro Arg Arg Gln
    1040            1045            1050
Ala Ser Ser Ala Val Arg Asp Ser Gly His Trp Gly Ser Ser Gly
    1055            1060            1065
Ser Gln Ala Ser Asp Ser Glu Gly His Ser Glu Glu Ser Asp Thr
    1070            1075            1080
Gln Ser Val Ser Gly His Gly Gln Asp Gly Pro His Gln Gln Ser
    1085            1090            1095
His Gln Glu Ser Ala Arg Asp Trp Ser Gly Gly Arg Ser Gly Arg
    1100            1105            1110
Ser Gly Ser Phe Ile Tyr Gln Val Ser Thr His Glu Gln Ser Glu
    1115            1120            1125
Ser Ala His Gly Arg Thr Arg Thr Ser Thr Gly Arg Arg Gln Gly
    1130            1135            1140
Ser His His Glu Gln Ala Arg Asp Ser Ser Arg His Ser Ala Ser
    1145            1150            1155
Gln Glu Gly Gln Asp Thr Ile Arg Ala His Pro Gly Ser Arg Arg
    1160            1165            1170
Gly Gly Arg Gln Gly Ser His His Glu Gln Ser Val Asp Arg Ser
    1175            1180            1185
Gly His Ser Gly Ser His Ser His Thr Thr Ser Gln Gly Arg
    1190            1195            1200
Ser Asp Ala Ser His Gly Gln Ser Gly Ser Arg Ser Ala Ser Arg
    1205            1210            1215
Gln Thr Arg Lys Asp Lys Gln Ser Gly Asp Gly Ser Arg His Ser
    1220            1225            1230
Gly Ser Arg His His Glu Ala Ala Ser Trp Ala Asp Ser Ser Arg
    1235            1240            1245
His Ser Gln Val Gly Gln Glu Gln Ser Gly Ser Arg Thr Ser
    1250            1255            1260
Arg His Gln Gly Ser Ser Val Ser Gln Asp Ser Asp Ser Glu Arg
    1265            1270            1275
His Ser Asp Asp Ser Glu Arg Leu Ser Gly Ser Ala Ser Arg Asn
    1280            1285            1290
His His Gly Ser Ser Arg Glu Gln Ser Arg Asp Gly Ser Arg His
    1295            1300            1305
```

```
Pro Gly Phe His Gln Glu Asp Arg Ala Ser His Gly His Ser Ala
    1310            1315                1320

Asp Ser Ser Arg Gln Ser Gly Thr His Thr Glu Ser Ser Ser
    1325            1330                1335

His Gly Gln Ala Val Ser Ser His Glu Gln Ala Arg Ser Ser Pro
    1340            1345                1350

Gly Glu Arg His Gly Ser Arg His Gln Gln Ser Ala Asp Ser Ser
    1355            1360                1365

Arg His Ser Gly Ile Gly His Arg Gln Ala Ser Ala Val Arg
    1370            1375                1380

Asp Ser Gly His Arg Gly Ser Ser Gly Ser Gln Val Thr Asn Ser
    1385            1390                1395

Glu Gly His Ser Glu Asp Ser Asp Thr Gln Ser Val Ser Ala His
    1400            1405                1410

Gly Gln Ala Gly Pro His Gln Gln Ser His Lys Glu Ser Ala Arg
    1415            1420                1425

Gly Gln Ser Gly Glu Ser Ser Gly Arg Ser Arg Ser Phe Leu Tyr
    1430            1435                1440

Gln Val Ser Ser His Glu Gln Ser Glu Ser Thr His Gly Gln Thr
    1445            1450                1455

Ala Pro Ser Thr Gly Gly Arg Gln Gly Ser Arg His Glu Gln Ala
    1460            1465                1470

Arg Asn Ser Ser Arg His Ser Ala Ser Gln Asp Gly Gln Asp Thr
    1475            1480                1485

Ile Arg Gly His Pro Gly Ser Ser Arg Gly Gly Arg Gln Gly Ser
    1490            1495                1500

Tyr His Glu Gln Ser Val Asp Arg Ser Gly His Ser Gly Tyr His
    1505            1510                1515

His Ser His Thr Thr Pro Gln Gly Arg Ser Asp Ala Ser His Gly
    1520            1525                1530

Gln Ser Gly Pro Arg Ser Ala Ser Arg Gln Thr Arg Asn Glu Glu
    1535            1540                1545

Gln Ser Gly Asp Gly Ser Arg His Ser Gly Ser Arg His His Glu
    1550            1555                1560

Pro Ser Thr Arg Ala Gly Ser Ser Arg His Ser Gln Val Gly Gln
    1565            1570                1575

Gly Glu Ser Ala Gly Ser Lys Thr Ser Arg Arg Gln Gly Ser Ser
    1580            1585                1590

Val Ser Gln Asp Arg Asp Ser Glu Gly His Ser Glu Asp Ser Glu
    1595            1600                1605

Arg Arg Ser Glu Ser Ala Ser Arg Asn His Tyr Gly Ser Ala Arg
    1610            1615                1620

Glu Gln Ser Arg His Gly Ser Arg Asn Pro Arg Ser His Gln Glu
    1625            1630                1635

Asp Arg Ala Ser His Gly His Ser Ala Glu Ser Ser Arg Gln Ser
    1640            1645                1650

Gly Thr Arg His Ala Glu Thr Ser Ser Gly Gly Gln Ala Ala Ser
    1655            1660                1665

Ser Gln Glu Gln Ala Arg Ser Ser Pro Gly Glu Arg His Gly Ser
    1670            1675                1680

Arg His Gln Gln Ser Ala Asp Ser Ser Thr Asp Ser Gly Thr Gly
    1685            1690                1695
```

-continued

```
Arg Arg Gln Asp Ser Ser Val Val Gly Asp Ser Gly Asn Arg Gly
1700                1705                1710

Ser Ser Gly Ser Gln Ala Ser Asp Ser Glu Gly His Ser Glu Glu
1715                1720                1725

Ser Asp Thr Gln Ser Val Ser Ala His Gly Gln Ala Gly Pro His
1730                1735                1740

Gln Gln Ser His Gln Glu Ser Thr Arg Gly Gln Ser Gly Glu Arg
1745                1750                1755

Ser Gly Arg Ser Gly Ser Phe Leu Tyr Gln Val Ser Thr His Glu
1760                1765                1770

Gln Ser Glu Ser Ala His Gly Arg Thr Gly Pro Ser Thr Gly Gly
1775                1780                1785

Arg Gln Arg Ser Arg His Glu Gln Ala Arg Asp Ser Ser Arg His
1790                1795                1800

Ser Ala Ser Gln Glu Gly Gln Asp Thr Ile Arg Gly His Pro Gly
1805                1810                1815

Ser Ser Arg Gly Gly Arg Gln Gly Ser His Tyr Glu Gln Ser Val
1820                1825                1830

Asp Ser Ser Gly His Ser Gly Ser His His Ser His Thr Thr Ser
1835                1840                1845

Gln Glu Arg Ser Asp Val Ser Arg Gly Gln Ser Gly Ser Arg Ser
1850                1855                1860

Val Ser Arg Gln Thr Arg Asn Glu Lys Gln Ser Gly Asp Gly Ser
1865                1870                1875

Arg His Ser Gly Ser Arg His His Glu Ala Ser Ser Arg Ala Asp
1880                1885                1890

Ser Ser Arg His Ser Gln Val Gly Gln Gly Gln Ser Ser Gly Pro
1895                1900                1905

Arg Thr Ser Arg Asn Gln Gly Ser Ser Val Ser Gln Asp Ser Asp
1910                1915                1920

Ser Gln Gly His Ser Glu Asp Ser Glu Arg Trp Ser Gly Ser Ala
1925                1930                1935

Ser Arg Asn His Leu Gly Ser Ala Trp Glu Gln Ser Arg Asp Gly
1940                1945                1950

Ser Arg His Pro Gly Ser His His Glu Asp Arg Ala Gly His Gly
1955                1960                1965

His Ser Ala Asp Ser Ser Arg Gln Ser Gly Thr Arg His Thr Glu
1970                1975                1980

Ser Ser Ser Arg Gly Gln Ala Ala Ser Ser His Glu Gln Ala Arg
1985                1990                1995

Ser Ser Ala Gly Glu Arg His Gly Ser His His Gln Leu Gln Ser
2000                2005                2010

Ala Asp Ser Ser Arg His Ser Gly Ile Gly His Gly Gln Ala Ser
2015                2020                2025

Ser Ala Val Arg Asp Ser Gly His Arg Gly Tyr Ser Gly Ser Gln
2030                2035                2040

Ala Ser Asp Ser Glu Gly His Ser Glu Asp Ser Asp Thr Gln Ser
2045                2050                2055

Val Ser Ala Gln Gly Lys Ala Gly Pro His Gln Gln Ser His Lys
2060                2065                2070

Glu Ser Ala Arg Gly Gln Ser Gly Glu Ser Ser Gly Arg Ser Gly
2075                2080                2085

Ser Phe Leu Tyr Gln Val Ser Thr His Glu Gln Ser Glu Ser Thr
```

```
            2090                2095                2100

His Gly Gln Ser Ala Pro Ser Thr Gly Arg Gln Gly Ser His
    2105                2110                2115

Tyr Asp Gln Ala Gln Asp Ser Ser Arg His Ser Ala Ser Gln Glu
    2120                2125                2130

Gly Gln Asp Thr Ile Arg Gly His Pro Gly Pro Ser Arg Gly Gly
    2135                2140                2145

Arg Gln Gly Ser His Gln Glu Gln Ser Val Asp Arg Ser Gly His
    2150                2155                2160

Ser Gly Ser His His Ser His Thr Thr Ser Gln Gly Arg Ser Asp
    2165                2170                2175

Ala Ser Arg Gly Gln Ser Gly Ser Arg Ser Ala Ser Arg Lys Thr
    2180                2185                2190

Tyr Asp Lys Glu Gln Ser Gly Asp Gly Ser Arg His Ser Gly Ser
    2195                2200                2205

His His His Glu Ala Ser Ser Trp Ala Asp Ser Ser Arg His Ser
    2210                2215                2220

Leu Val Gly Gln Gly Gln Ser Ser Gly Pro Arg Thr Ser Arg Pro
    2225                2230                2235

Arg Gly Ser Ser Val Ser Gln Asp Ser Asp Ser Glu Gly His Ser
    2240                2245                2250

Glu Asp Ser Glu Arg Arg Ser Gly Ser Ala Ser Arg Asn His His
    2255                2260                2265

Gly Ser Ala Gln Glu Gln Ser Arg Asp Gly Ser Arg His Pro Arg
    2270                2275                2280

Ser His His Glu Asp Arg Ala Gly His Gly His Ser Ala Glu Ser
    2285                2290                2295

Ser Arg Gln Ser Gly Thr His His Ala Glu Asn Ser Ser Gly Gly
    2300                2305                2310

Gln Ala Ala Ser Ser His Glu Gln Ala Arg Ser Ser Ala Gly Glu
    2315                2320                2325

Arg His Gly Ser His His Gln Gln Ser Ala Asp Ser Ser Arg His
    2330                2335                2340

Ser Gly Ile Gly His Gly Gln Ala Ser Ser Ala Val Arg Asp Ser
    2345                2350                2355

Gly His Arg Gly Ser Ser Gly Ser Gln Ala Ser Asp Ser Glu Gly
    2360                2365                2370

His Ser Glu Asp Ser Asp Thr Gln Ser Val Ser Ala His Gly Gln
    2375                2380                2385

Ala Gly Pro His Gln Gln Ser His Gln Glu Ser Thr Arg Gly Arg
    2390                2395                2400

Ser Ala Gly Arg Ser Gly Arg Ser Gly Ser Phe Leu Tyr Gln Val
    2405                2410                2415

Ser Thr His Glu Gln Ser Glu Ser Ala His Gly Arg Thr Gly Thr
    2420                2425                2430

Ser Thr Gly Gly Arg Gln Gly Ser His His Lys Gln Ala Arg Asp
    2435                2440                2445

Ser Ser Arg His Ser Thr Ser Gln Glu Gly Gln Asp Thr Ile His
    2450                2455                2460

Gly His Pro Gly Ser Ser Ser Gly Gly Arg Gln Gly Ser His Tyr
    2465                2470                2475

Glu Gln Leu Val Asp Arg Ser Gly His Ser Gly Ser His His Ser
    2480                2485                2490
```

```
His Thr Thr Ser Gln Gly Arg Ser Asp Ala Ser His Gly His Ser
2495                2500                2505

Gly Ser Arg Ser Ala Ser Arg Gln Thr Arg Asn Asp Glu Gln Ser
2510                2515                2520

Gly Asp Gly Ser Arg His Ser Gly Ser Arg His His Glu Ala Ser
2525                2530                2535

Ser Arg Ala Asp Ser Ser Gly His Ser Gln Val Gly Gln Gly Gln
2540                2545                2550

Ser Glu Gly Pro Arg Thr Ser Arg Asn Trp Gly Ser Ser Phe Ser
2555                2560                2565

Gln Asp Ser Asp Ser Gln Gly His Ser Glu Asp Ser Glu Arg Trp
2570                2575                2580

Ser Gly Ser Ala Ser Arg Asn His His Gly Ser Ala Gln Glu Gln
2585                2590                2595

Leu Arg Asp Gly Ser Arg His Pro Arg Ser His Gln Glu Asp Arg
2600                2605                2610

Ala Gly His Gly His Ser Ala Asp Ser Ser Arg Gln Ser Gly Thr
2615                2620                2625

Arg His Thr Gln Thr Ser Ser Gly Gly Gln Ala Ala Ser Ser His
2630                2635                2640

Glu Gln Ala Arg Ser Ser Ala Gly Glu Arg His Gly Ser His His
2645                2650                2655

Gln Gln Ser Ala Asp Ser Ser Arg His Ser Gly Ile Gly His Gly
2660                2665                2670

Gln Ala Ser Ser Ala Val Arg Asp Ser Gly His Arg Gly Tyr Ser
2675                2680                2685

Gly Ser Gln Ala Ser Asp Asn Glu Gly His Ser Glu Asp Ser Asp
2690                2695                2700

Thr Gln Ser Val Ser Ala His Gly Gln Ala Gly Ser His Gln Gln
2705                2710                2715

Ser His Gln Glu Ser Ala Arg Gly Arg Ser Gly Glu Thr Ser Gly
2720                2725                2730

His Ser Gly Ser Phe Leu Tyr Gln Val Ser Thr His Glu Gln Ser
2735                2740                2745

Glu Ser Ser His Gly Trp Thr Gly Pro Ser Thr Arg Gly Arg Gln
2750                2755                2760

Gly Ser Arg His Glu Gln Ala Gln Asp Ser Ser Arg His Ser Ala
2765                2770                2775

Ser Gln Asp Gly Gln Asp Thr Ile Arg Gly His Pro Gly Ser Ser
2780                2785                2790

Arg Gly Gly Arg Gln Gly Tyr His His Glu His Ser Val Asp Ser
2795                2800                2805

Ser Gly His Ser Gly Ser His Ser His Thr Ser Gln Gly
2810                2815                2820

Arg Ser Asp Ala Ser Arg Gly Gln Ser Gly Ser Arg Ser Ala Ser
2825                2830                2835

Arg Thr Thr Arg Asn Glu Glu Gln Ser Gly Asp Gly Ser Arg His
2840                2845                2850

Ser Gly Ser Arg His His Glu Ala Ser Thr His Ala Asp Ile Ser
2855                2860                2865

Arg His Ser Gln Ala Val Gln Gly Gln Ser Glu Gly Ser Arg Arg
2870                2875                2880
```

```
Ser Arg Arg Gln Gly Ser Ser Val Ser Gln Asp Ser Asp Ser Glu
    2885                2890                2895

Gly His Ser Glu Asp Ser Glu Arg Trp Ser Gly Ser Ala Ser Arg
    2900                2905                2910

Asn His His Gly Ser Ala Gln Glu Gln Leu Arg Asp Gly Ser Arg
    2915                2920                2925

His Pro Arg Ser His Gln Glu Asp Arg Ala Gly His Gly His Ser
    2930                2935                2940

Ala Asp Ser Ser Arg Gln Ser Gly Thr Arg His Thr Gln Thr Ser
    2945                2950                2955

Ser Gly Gly Gln Ala Ala Ser Ser His Glu Gln Ala Arg Ser Ser
    2960                2965                2970

Ala Gly Glu Arg His Gly Ser His His Gln Gln Ser Ala Asp Ser
    2975                2980                2985

Ser Arg His Ser Gly Ile Gly His Gly Gln Ala Ser Ser Ala Val
    2990                2995                3000

Arg Asp Ser Gly His Arg Gly Tyr Ser Gly Ser Gln Ala Ser Asp
    3005                3010                3015

Asn Glu Gly His Ser Glu Asp Ser Asp Thr Gln Ser Val Ser Ala
    3020                3025                3030

His Gly Gln Ala Gly Ser His Gln Gln Ser His Gln Glu Ser Ala
    3035                3040                3045

Arg Gly Arg Ser Gly Glu Thr Ser Gly His Ser Gly Ser Phe Leu
    3050                3055                3060

Tyr Gln Val Ser Thr His Glu Gln Ser Glu Ser Ser His Gly Trp
    3065                3070                3075

Thr Gly Pro Ser Thr Arg Gly Arg Gln Gly Ser Arg His Glu Gln
    3080                3085                3090

Ala Gln Asp Ser Ser Arg His Ser Ala Ser Gln Tyr Gly Gln Asp
    3095                3100                3105

Thr Ile Arg Gly His Pro Gly Ser Ser Arg Gly Gly Arg Gln Gly
    3110                3115                3120

Tyr His His Glu His Ser Val Asp Ser Ser Gly His Ser Gly Ser
    3125                3130                3135

His His Ser His Thr Thr Ser Gln Gly Arg Ser Asp Ala Ser Arg
    3140                3145                3150

Gly Gln Ser Gly Ser Arg Ser Ala Ser Arg Thr Thr Arg Asn Glu
    3155                3160                3165

Glu Gln Ser Gly Asp Ser Ser Arg His Ser Val Ser Arg His His
    3170                3175                3180

Glu Ala Ser Thr His Ala Asp Ile Ser Arg His Ser Gln Ala Val
    3185                3190                3195

Gln Gly Gln Ser Glu Gly Ser Arg Arg Ser Arg Arg Gln Gly Ser
    3200                3205                3210

Ser Val Ser Gln Asp Ser Asp Ser Glu Gly His Ser Glu Asp Ser
    3215                3220                3225

Glu Arg Trp Ser Gly Ser Ala Ser Arg Asn His Arg Gly Ser Val
    3230                3235                3240

Gln Glu Gln Ser Arg His Gly Ser Arg His Pro Arg Ser His His
    3245                3250                3255

Glu Asp Arg Ala Gly His Gly His Ser Ala Asp Arg Ser Arg Gln
    3260                3265                3270

Ser Gly Thr Arg His Ala Glu Thr Ser Ser Gly Gly Gln Ala Ala
```

-continued

```
            3275                3280                3285
Ser Ser His Glu Gln Ala Arg Ser Ser Pro Gly Glu Arg His Gly
    3290                3295                3300

Ser Arg His Gln Gln Ser Ala Asp Ser Ser Arg His Ser Gly Ile
    3305                3310                3315

Pro Arg Gly Gln Ala Ser Ser Ala Val Arg Asp Ser Arg His Trp
    3320                3325                3330

Gly Ser Ser Gly Ser Gln Ala Ser Asp Ser Glu Gly His Ser Glu
    3335                3340                3345

Glu Ser Asp Thr Gln Ser Val Ser Gly His Gly Gln Ala Gly Pro
    3350                3355                3360

His Gln Gln Ser His Gln Glu Ser Ala Arg Asp Arg Ser Gly Gly
    3365                3370                3375

Arg Ser Gly Arg Ser Gly Ser Phe Leu Tyr Gln Val Ser Thr His
    3380                3385                3390

Glu Gln Ser Glu Ser Ala His Gly Arg Thr Arg Thr Ser Thr Gly
    3395                3400                3405

Arg Arg Gln Gly Ser His His Glu Gln Ala Arg Asp Ser Ser Arg
    3410                3415                3420

His Ser Ala Ser Gln Glu Gly Gln Asp Thr Ile Arg Gly His Pro
    3425                3430                3435

Gly Ser Ser Arg Arg Gly Arg Gln Gly Ser His Tyr Glu Gln Ser
    3440                3445                3450

Val Asp Arg Ser Gly His Ser Gly Ser His His Ser His Thr Thr
    3455                3460                3465

Ser Gln Gly Arg Ser Asp Ala Ser Arg Gly Gln Ser Gly Ser Arg
    3470                3475                3480

Ser Ala Ser Arg Gln Thr Arg Asn Asp Glu Gln Ser Gly Asp Gly
    3485                3490                3495

Ser Arg His Ser Trp Ser His His His Glu Ala Ser Thr Gln Ala
    3500                3505                3510

Asp Ser Ser Arg His Ser Gln Ser Gly Gln Gly Gln Ser Ala Gly
    3515                3520                3525

Pro Arg Thr Ser Arg Asn Gln Gly Ser Ser Val Ser Gln Asp Ser
    3530                3535                3540

Asp Ser Gln Gly His Ser Glu Asp Ser Glu Arg Trp Ser Gly Ser
    3545                3550                3555

Ala Ser Arg Asn His Arg Gly Ser Ala Gln Glu Gln Ser Arg Asp
    3560                3565                3570

Gly Ser Arg His Pro Thr Ser His His Glu Asp Arg Ala Gly His
    3575                3580                3585

Gly His Ser Ala Glu Ser Ser Arg Gln Ser Gly Thr His His Ala
    3590                3595                3600

Glu Asn Ser Ser Gly Gly Gln Ala Ala Ser Ser His Glu Gln Ala
    3605                3610                3615

Arg Ser Ser Ala Gly Glu Arg His Gly Ser His His Gln Gln Ser
    3620                3625                3630

Ala Asp Ser Ser Arg His Ser Gly Ile Gly His Gly Gln Ala Ser
    3635                3640                3645

Ser Ala Val Arg Asp Ser Gly His Arg Gly Ser Ser Gly Ser Gln
    3650                3655                3660

Ala Ser Asp Ser Glu Gly His Ser Glu Asp Ser Asp Thr Gln Ser
    3665                3670                3675
```

-continued

```
Val Ser Ala His Gly Gln Ala Gly Pro His Gln Ser His Gln
3680            3685                3690

Glu Ser Thr Arg Gly Arg Ser Ala Gly Arg Ser Gly Arg Ser Gly
3695            3700                3705

Ser Phe Leu Tyr Gln Val Ser Thr His Glu Gln Ser Glu Ser Ala
3710            3715                3720

His Gly Arg Ala Gly Pro Ser Thr Gly Gly Arg Gln Gly Ser Arg
3725            3730                3735

His Glu Gln Ala Arg Asp Ser Ser Arg His Ser Ala Ser Gln Glu
3740            3745                3750

Gly Gln Asp Thr Ile Arg Gly His Pro Gly Ser Arg Arg Gly Gly
3755            3760                3765

Arg Gln Gly Ser Tyr His Glu Gln Ser Val Asp Arg Ser Gly His
3770            3775                3780

Ser Gly Ser His His Ser His Thr Thr Ser Gln Gly Arg Ser Asp
3785            3790                3795

Ala Ser His Gly Gln Ser Gly Ser Arg Ser Ala Ser Arg Glu Thr
3800            3805                3810

Arg Asn Glu Glu Gln Ser Gly Asp Gly Ser Arg His Ser Gly Ser
3815            3820                3825

Arg His His Glu Ala Ser Thr Gln Ala Asp Ser Ser Arg His Ser
3830            3835                3840

Gln Ser Gly Gln Gly Glu Ser Ala Gly Ser Arg Arg Ser Arg Arg
3845            3850                3855

Gln Gly Ser Ser Val Ser Gln Asp Ser Asp Ser Glu Ala Tyr Pro
3860            3865                3870

Glu Asp Ser Glu Arg Arg Ser Glu Ser Ala Ser Arg Asn His His
3875            3880                3885

Gly Ser Ser Arg Glu Gln Ser Arg Asp Gly Ser Arg His Pro Gly
3890            3895                3900

Ser Ser His Arg Asp Thr Ala Ser His Val Gln Ser Ser Pro Val
3905            3910                3915

Gln Ser Asp Ser Ser Thr Ala Lys Glu His Gly His Phe Ser Ser
3920            3925                3930

Leu Ser Gln Asp Ser Ala Tyr His Ser Gly Ile Gln Ser Arg Gly
3935            3940                3945

Ser Pro His Ser Ser Ser Tyr His Tyr Gln Ser Glu Gly Thr
3950            3955                3960

Glu Arg Gln Lys Gly Gln Ser Gly Leu Val Trp Arg His Gly Ser
3965            3970                3975

Tyr Gly Ser Ala Asp Tyr Asp Tyr Gly Glu Ser Gly Phe Arg His
3980            3985                3990

Ser Gln His Gly Ser Val Ser Tyr Asn Ser Asn Pro Val Val Phe
3995            4000                4005

Lys Glu Arg Ser Asp Ile Cys Lys Ala Ser Ala Phe Gly Lys Asp
4010            4015                4020

His Pro Arg Tyr Tyr Ala Thr Tyr Ile Asn Lys Asp Pro Gly Leu
4025            4030                4035

Cys Gly His Ser Ser Asp Ile Ser Lys Gln Leu Gly Phe Ser Gln
4040            4045                4050

Ser Gln Arg Tyr Tyr Tyr Tyr Glu
4055            4060
```

```
<210> SEQ ID NO 3
<211> LENGTH: 416
<212> TYPE: PRT
<213> ORGANISM: Homo sapiens

<400> SEQUENCE: 3

Ala Gly Pro His Gln Gln Ser His Gln Glu Ser Thr Arg Gly Arg Ser
1               5                   10                  15

Ala Gly Arg Ser Gly Arg Ser Gly Ser Phe Leu Tyr Gln Val Ser Thr
            20                  25                  30

His Glu Gln Ser Glu Ser Ala His Gly Arg Thr Gly Thr Ser Thr Gly
        35                  40                  45

Gly Arg Gln Gly Ser His His Gln Gln Ala Arg Asp Ser Ser Arg His
    50                  55                  60

Ser Thr Ser Gln Glu Gly Gln Asp Thr Ile His Gly His Arg Gly Ser
65                  70                  75                  80

Ser Ser Gly Gly Arg Gln Gly Ser His Tyr Glu Gln Leu Val Asp Arg
                85                  90                  95

Ser Gly His Ser Gly Ser His His Ser His Thr Thr Ser Gln Gly Arg
            100                 105                 110

Ser Asp Ala Ser His Gly His Ser Gly Ser Arg Ser Ala Ser Arg Gln
        115                 120                 125

Thr Arg Asn Asp Glu Gln Ser Gly Asp Gly Ser Arg His Ser Gly Ser
130                 135                 140

Arg His His Glu Ala Ser Ser Arg Ala Asp Ser Ser Gly His Ser Gln
145                 150                 155                 160

Val Gly Gln Gly Gln Ser Glu Gly Pro Arg Thr Ser Arg Asn Trp Gly
                165                 170                 175

Ser Ser Phe Ser Gln Asp Ser Asp Ser Gln Gly His Ser Glu Asp Ser
            180                 185                 190

Glu Arg Trp Ser Gly Ser Ala Ser Arg Asn His His Gly Ser Ala Gln
        195                 200                 205

Glu Gln Leu Arg Asp Gly Ser Arg His Pro Arg Ser His Gln Glu Asp
    210                 215                 220

Arg Ala Gly His Gly His Ser Ala Asp Ser Ser Arg Gln Ser Gly Thr
225                 230                 235                 240

Arg His Thr Gln Thr Ser Ser Gly Gly Gln Ala Ala Ser Ser His Glu
                245                 250                 255

Gln Ala Arg Ser Ser Ala Gly Asp Arg His Gly Ser His His Gln Gln
            260                 265                 270

Ser Ala Asp Ser Ser Arg His Ser Gly Ile Gly His Gly Gln Ala Ser
        275                 280                 285

Ser Ala Val Arg Asp Ser Gly His Arg Gly Tyr Ser Gly Ser Gln Ala
    290                 295                 300

Ser Asp Asn Glu Gly His Ser Glu Asp Ser Asp Thr Gln Ser Val Ser
305                 310                 315                 320

Ala His Gly Gln Ala Gly Ser His Gln Gln Ser His Gln Glu Ser Ala
                325                 330                 335

Arg Gly Arg Ser Gly Glu Thr Ser Gly His Ser Gly Ser Phe Leu Tyr
            340                 345                 350

Gln Val Ser Thr His Glu Gln Ser Glu Ser His Gly Trp Thr Gly
        355                 360                 365

Pro Ser Thr Arg Gly Arg Gln Gly Ser Arg His Glu Gln Ala Gln Asp
    370                 375                 380
```

-continued

Ser Ser Arg His Ser Ala Ser Gln Asp Gly Gln Asp Thr Ile Arg Gly
385                 390                 395                 400

His Pro Gly Ser Ser Arg Gly Gly Arg Gln Gly Tyr His His Glu Gln
                405                 410                 415

<210> SEQ ID NO 4
<211> LENGTH: 4061
<212> TYPE: PRT
<213> ORGANISM: Homo sapiens

<400> SEQUENCE: 4

Met Ser Thr Leu Leu Glu Asn Ile Phe Ala Ile Ile Asn Leu Phe Lys
1               5                   10                  15

Gln Tyr Ser Lys Lys Asp Lys Asn Thr Asp Thr Leu Ser Lys Lys Glu
            20                  25                  30

Leu Lys Glu Leu Leu Glu Lys Glu Phe Arg Gln Ile Leu Lys Asn Pro
        35                  40                  45

Asp Asp Pro Asp Met Val Asp Val Phe Met Asp His Leu Asp Ile Asp
    50                  55                  60

His Asn Lys Lys Ile Asp Phe Thr Glu Phe Leu Leu Met Val Phe Lys
65                  70                  75                  80

Leu Ala Gln Ala Tyr Tyr Glu Ser Thr Arg Lys Glu Asn Leu Pro Ile
                85                  90                  95

Ser Gly His Lys His Arg Lys His Ser His His Asp Lys Glu Asp
            100                 105                 110

Asn Lys Gln Glu Glu Asn Lys Glu Asn Arg Lys Arg Pro Ser Ser Leu
        115                 120                 125

Glu Arg Arg Asn Asn Arg Lys Gly Asn Lys Gly Arg Ser Lys Ser Pro
130                 135                 140

Arg Glu Thr Gly Gly Lys Arg His Glu Ser Ser Ser Glu Lys Lys Glu
145                 150                 155                 160

Arg Lys Gly Tyr Ser Pro Thr His Arg Glu Glu Glu Tyr Gly Lys Asn
                165                 170                 175

His His Asn Ser Ser Lys Lys Glu Lys Asn Lys Thr Glu Asn Thr Arg
            180                 185                 190

Leu Gly Asp Asn Arg Lys Arg Leu Ser Glu Arg Leu Glu Glu Lys Glu
        195                 200                 205

Asp Asn Glu Glu Gly Val Tyr Asp Tyr Glu Asn Thr Gly Arg Met Thr
    210                 215                 220

Gln Lys Trp Ile Gln Ser Gly His Ile Ala Thr Tyr Tyr Thr Ile Gln
225                 230                 235                 240

Asp Glu Ala Tyr Asp Thr Thr Asp Ser Leu Leu Glu Glu Asn Lys Ile
                245                 250                 255

Tyr Glu Arg Ser Arg Ser Ser Asp Gly Lys Ser Ser Ser Gln Val Asn
            260                 265                 270

Arg Ser Arg His Glu Asn Thr Ser Gln Val Pro Leu Gln Glu Ser Arg
        275                 280                 285

Thr Arg Lys Arg Arg Gly Ser Arg Val Ser Gln Asp Arg Asp Ser Glu
    290                 295                 300

Gly His Ser Glu Asp Glu Arg His Ser Gly Ser Ala Ser Arg Asn
305                 310                 315                 320

His His Gly Ser Ala Trp Glu Gln Ser Arg Asp Gly Ser Arg His Pro
                325                 330                 335

Arg Ser His Asp Glu Asp Arg Ala Ser His Gly His Ser Ala Asp Ser

```
            340                 345                 350
Ser Arg Gln Ser Gly Thr Arg His Ala Glu Thr Ser Ser Arg Gly Gln
            355                 360                 365
Thr Ala Ser Ser His Glu Gln Ala Arg Ser Ser Pro Gly Glu Arg His
            370                 375                 380
Gly Ser Gly His Gln Gln Ser Ala Asp Ser Ser Arg His Ser Ala Thr
385                 390                 395                 400
Gly Arg Gly Gln Ala Ser Ser Ala Val Ser Asp Arg Gly His Arg Gly
                405                 410                 415
Ser Ser Gly Ser Gln Ala Ser Asp Ser Glu Gly His Ser Glu Asn Ser
            420                 425                 430
Asp Thr Gln Ser Val Ser Gly His Gly Lys Ala Gly Leu Arg Gln Gln
            435                 440                 445
Ser His Gln Glu Ser Thr Arg Gly Arg Ser Gly Glu Arg Ser Gly Arg
            450                 455                 460
Ser Gly Ser Ser Leu Tyr Gln Val Ser Thr His Glu Gln Pro Asp Ser
465                 470                 475                 480
Ala His Gly Arg Thr Gly Thr Ser Thr Gly Gly Arg Gln Gly Ser His
                485                 490                 495
His Glu Gln Ala Arg Asp Ser Ser Arg His Ser Ala Ser Gln Glu Gly
            500                 505                 510
Gln Asp Thr Ile Arg Gly His Pro Gly Ser Ser Arg Gly Gly Arg Gln
            515                 520                 525
Gly Ser His His Glu Gln Ser Val Asn Arg Ser Gly His Ser Gly Ser
            530                 535                 540
His His Ser His Thr Thr Ser Gln Gly Arg Ser Asp Ala Ser His Gly
545                 550                 555                 560
Gln Ser Gly Ser Arg Ser Ala Ser Arg Gln Thr Arg Asn Glu Glu Gln
                565                 570                 575
Ser Gly Asp Gly Thr Arg His Ser Gly Ser Arg His His Glu Ala Ser
            580                 585                 590
Ser Gln Ala Asp Ser Ser Arg His Ser Gln Val Gly Gln Gly Gln Ser
            595                 600                 605
Ser Gly Pro Arg Thr Ser Arg Asn Gln Gly Ser Ser Val Ser Gln Asp
            610                 615                 620
Ser Asp Ser Gln Gly His Ser Glu Asp Ser Glu Arg Trp Ser Gly Ser
625                 630                 635                 640
Ala Ser Arg Asn His His Gly Ser Ala Gln Glu Gln Ser Arg Asp Gly
                645                 650                 655
Ser Arg His Pro Arg Ser His His Glu Asp Arg Ala Gly His Gly His
            660                 665                 670
Ser Ala Asp Ser Ser Arg Lys Ser Gly Thr Arg His Thr Gln Asn Ser
            675                 680                 685
Ser Gly Gln Ala Ala Ser Ser His Glu Gln Ala Arg Ser Ser Ala
            690                 695                 700
Gly Glu Arg His Gly Ser Arg His Gln Leu Gln Ser Ala Asp Ser Ser
705                 710                 715                 720
Arg His Ser Gly Thr Gly His Gly Gln Ala Ser Ser Ala Val Arg Asp
                725                 730                 735
Ser Gly His Arg Gly Ser Ser Gly Ser Gln Ala Thr Asp Ser Glu Gly
            740                 745                 750
His Ser Glu Asp Ser Asp Thr Gln Ser Val Ser Gly His Gly Gln Ala
            755                 760                 765
```

-continued

```
Gly His His Gln Gln Ser His Gln Glu Ser Ala Arg Asp Arg Ser Gly
    770                 775                 780

Glu Arg Ser Arg Arg Ser Gly Ser Phe Leu Tyr Gln Val Ser Thr His
785                 790                 795                 800

Lys Gln Ser Glu Ser Ser His Gly Trp Thr Gly Pro Ser Thr Gly Val
                805                 810                 815

Arg Gln Gly Ser His His Glu Gln Ala Arg Asp Asn Ser Arg His Ser
            820                 825                 830

Ala Ser Gln Asp Gly Gln Asp Thr Ile Arg Gly His Pro Gly Ser Ser
        835                 840                 845

Arg Arg Gly Arg Gln Gly Ser His His Glu Gln Ser Val Asp Arg Ser
    850                 855                 860

Gly His Ser Gly Ser His His Ser His Thr Thr Ser Gln Gly Arg Ser
865                 870                 875                 880

Asp Ala Ser Arg Gly Gln Ser Gly Ser Arg Ser Ala Ser Arg Thr Thr
                885                 890                 895

Arg Asn Glu Glu Gln Ser Arg Asp Gly Ser Arg His Ser Gly Ser Arg
            900                 905                 910

His His Glu Ala Ser Ser His Ala Asp Ile Ser Arg His Ser Gln Ala
        915                 920                 925

Gly Gln Gly Gln Ser Glu Gly Ser Arg Thr Ser Arg Arg Gln Gly Ser
    930                 935                 940

Ser Val Ser Gln Asp Ser Asp Ser Glu Gly His Ser Glu Asp Ser Glu
945                 950                 955                 960

Arg Trp Ser Gly Ser Ala Ser Arg Asn His Arg Gly Ser Ala Gln Glu
                965                 970                 975

Gln Ser Arg His Gly Ser Arg His Pro Arg Ser His His Glu Asp Arg
            980                 985                 990

Ala Gly His Gly His Ser Ala Asp  Ser Ser Arg Gln Ser  Gly Thr Pro
        995                 1000                1005

His Ala  Glu Thr Ser Ser Gly  Gly Gln Ala Ala Ser  Ser His Glu
    1010                1015                1020

Gln Ala  Arg Ser Ser Pro Gly  Glu Arg His Gly Ser  Arg His Gln
    1025                1030                1035

Gln Ser  Ala Asp Ser Ser Arg  His Ser Gly Ile Pro  Arg Arg Gln
    1040                1045                1050

Ala Ser  Ser Ala Val Arg Asp  Ser Gly His Trp Gly  Ser Ser Gly
    1055                1060                1065

Ser Gln  Ala Ser Asp Ser Glu  Gly His Ser Glu Glu  Ser Asp Thr
    1070                1075                1080

Gln Ser  Val Ser Gly His Gly  Gln Asp Gly Pro His  Gln Gln Ser
    1085                1090                1095

His Gln  Glu Ser Ala Arg Asp  Trp Ser Gly Gly Arg  Ser Gly Arg
    1100                1105                1110

Ser Gly  Ser Phe Ile Tyr Gln  Val Ser Thr His Glu  Gln Ser Glu
    1115                1120                1125

Ser Ala  His Gly Arg Thr Arg  Thr Ser Thr Gly Arg  Arg Gln Gly
    1130                1135                1140

Ser His  His Glu Gln Ala Arg  Asp Ser Ser Arg His  Ser Ala Ser
    1145                1150                1155

Gln Glu  Gly Gln Asp Thr Ile  Arg Ala His Pro Gly  Ser Arg Arg
    1160                1165                1170
```

| | | | | | | | | | | | |
|---|---|---|---|---|---|---|---|---|---|---|---|
| Gly | Gly | Arg | Gln | Gly | Ser | His | His | Glu | Gln | Ser | Val | Asp | Arg | Ser |
| | 1175 | | | | 1180 | | | | 1185 | | |
| Gly | His | Ser | Gly | Ser | His | His | Ser | His | Thr | Thr | Ser | Gln | Gly | Arg |
| | 1190 | | | | 1195 | | | | 1200 | | |
| Ser | Asp | Ala | Ser | His | Gly | Gln | Ser | Gly | Ser | Arg | Ser | Ala | Ser | Arg |
| | 1205 | | | | 1210 | | | | 1215 | | |
| Gln | Thr | Arg | Lys | Asp | Lys | Gln | Ser | Gly | Asp | Gly | Ser | Arg | His | Ser |
| | 1220 | | | | 1225 | | | | 1230 | | |
| Gly | Ser | Arg | His | His | Glu | Ala | Ala | Ser | Trp | Ala | Asp | Ser | Ser | Arg |
| | 1235 | | | | 1240 | | | | 1245 | | |
| His | Ser | Gln | Val | Gly | Gln | Glu | Gln | Ser | Ser | Gly | Ser | Arg | Thr | Ser |
| | 1250 | | | | 1255 | | | | 1260 | | |
| Arg | His | Gln | Gly | Ser | Ser | Val | Ser | Gln | Asp | Ser | Asp | Ser | Glu | Arg |
| | 1265 | | | | 1270 | | | | 1275 | | |
| His | Ser | Asp | Asp | Ser | Glu | Arg | Leu | Ser | Gly | Ser | Ala | Ser | Arg | Asn |
| | 1280 | | | | 1285 | | | | 1290 | | |
| His | His | Gly | Ser | Ser | Arg | Glu | Gln | Ser | Arg | Asp | Gly | Ser | Arg | His |
| | 1295 | | | | 1300 | | | | 1305 | | |
| Pro | Gly | Phe | His | Gln | Glu | Asp | Arg | Ala | Ser | His | Gly | His | Ser | Ala |
| | 1310 | | | | 1315 | | | | 1320 | | |
| Asp | Ser | Ser | Arg | Gln | Ser | Gly | Thr | His | His | Thr | Glu | Ser | Ser | Ser |
| | 1325 | | | | 1330 | | | | 1335 | | |
| His | Gly | Gln | Ala | Val | Ser | Ser | His | Glu | Gln | Ala | Arg | Ser | Ser | Pro |
| | 1340 | | | | 1345 | | | | 1350 | | |
| Gly | Glu | Arg | His | Gly | Ser | Arg | His | Gln | Gln | Ser | Ala | Asp | Ser | Ser |
| | 1355 | | | | 1360 | | | | 1365 | | |
| Arg | His | Ser | Gly | Ile | Gly | His | Arg | Gln | Ala | Ser | Ser | Ala | Val | Arg |
| | 1370 | | | | 1375 | | | | 1380 | | |
| Asp | Ser | Gly | His | Arg | Gly | Ser | Ser | Gly | Ser | Gln | Val | Thr | Asn | Ser |
| | 1385 | | | | 1390 | | | | 1395 | | |
| Glu | Gly | His | Ser | Glu | Asp | Ser | Asp | Thr | Gln | Ser | Val | Ser | Ala | His |
| | 1400 | | | | 1405 | | | | 1410 | | |
| Gly | Gln | Ala | Gly | Pro | His | Gln | Gln | Ser | His | Lys | Glu | Ser | Ala | Arg |
| | 1415 | | | | 1420 | | | | 1425 | | |
| Gly | Gln | Ser | Gly | Glu | Ser | Ser | Gly | Arg | Ser | Arg | Ser | Phe | Leu | Tyr |
| | 1430 | | | | 1435 | | | | 1440 | | |
| Gln | Val | Ser | Ser | His | Glu | Gln | Ser | Glu | Ser | Thr | His | Gly | Gln | Thr |
| | 1445 | | | | 1450 | | | | 1455 | | |
| Ala | Pro | Ser | Thr | Gly | Gly | Arg | Gln | Gly | Ser | Arg | His | Glu | Gln | Ala |
| | 1460 | | | | 1465 | | | | 1470 | | |
| Arg | Asn | Ser | Ser | Arg | His | Ser | Ala | Ser | Gln | Asp | Gly | Gln | Asp | Thr |
| | 1475 | | | | 1480 | | | | 1485 | | |
| Ile | Arg | Gly | His | Pro | Gly | Ser | Ser | Arg | Gly | Gly | Arg | Gln | Gly | Ser |
| | 1490 | | | | 1495 | | | | 1500 | | |
| Tyr | His | Glu | Gln | Ser | Val | Asp | Arg | Ser | Gly | His | Ser | Gly | Tyr | His |
| | 1505 | | | | 1510 | | | | 1515 | | |
| His | Ser | His | Thr | Thr | Pro | Gln | Gly | Arg | Ser | Asp | Ala | Ser | His | Gly |
| | 1520 | | | | 1525 | | | | 1530 | | |
| Gln | Ser | Gly | Pro | Arg | Ser | Ala | Ser | Arg | Gln | Thr | Arg | Asn | Glu | Glu |
| | 1535 | | | | 1540 | | | | 1545 | | |
| Gln | Ser | Gly | Asp | Gly | Ser | Arg | His | Ser | Gly | Ser | Arg | His | His | Glu |
| | 1550 | | | | 1555 | | | | 1560 | | |
| Pro | Ser | Thr | Arg | Ala | Gly | Ser | Ser | Arg | His | Ser | Gln | Val | Gly | Gln |

```
            1565                1570                1575

Gly Glu Ser Ala Gly Ser Lys Thr Ser Arg Arg Gln Gly Ser Ser
        1580                1585                1590

Val Ser Gln Asp Arg Asp Ser Glu Gly His Ser Glu Asp Ser Glu
    1595                1600                1605

Arg Arg Ser Glu Ser Ala Ser Arg Asn His Tyr Gly Ser Ala Arg
    1610                1615                1620

Glu Gln Ser Arg His Gly Ser Arg Asn Pro Arg Ser His Gln Glu
    1625                1630                1635

Asp Arg Ala Ser His Gly His Ser Ala Glu Ser Ser Arg Gln Ser
    1640                1645                1650

Gly Thr Arg His Ala Glu Thr Ser Ser Gly Gly Gln Ala Ala Ser
    1655                1660                1665

Ser Gln Glu Gln Ala Arg Ser Ser Pro Gly Glu Arg His Gly Ser
    1670                1675                1680

Arg His Gln Gln Ser Ala Asp Ser Ser Thr Asp Ser Gly Thr Gly
    1685                1690                1695

Arg Arg Gln Asp Ser Ser Val Val Gly Asp Ser Gly Asn Arg Gly
    1700                1705                1710

Ser Ser Gly Ser Gln Ala Ser Asp Ser Glu Gly His Ser Glu Glu
    1715                1720                1725

Ser Asp Thr Gln Ser Val Ser Ala His Gly Gln Ala Gly Pro His
    1730                1735                1740

Gln Gln Ser His Gln Glu Ser Thr Arg Gly Gln Ser Gly Glu Arg
    1745                1750                1755

Ser Gly Arg Ser Gly Ser Phe Leu Tyr Gln Val Ser Thr His Glu
    1760                1765                1770

Gln Ser Glu Ser Ala His Gly Arg Thr Gly Pro Ser Thr Gly Gly
    1775                1780                1785

Arg Gln Arg Ser Arg His Glu Gln Ala Arg Asp Ser Ser Arg His
    1790                1795                1800

Ser Ala Ser Gln Glu Gly Gln Asp Thr Ile Arg Gly His Pro Gly
    1805                1810                1815

Ser Ser Arg Gly Gly Arg Gln Gly Ser His Tyr Glu Gln Ser Val
    1820                1825                1830

Asp Ser Ser Gly His Ser Gly Ser His His Ser His Thr Thr Ser
    1835                1840                1845

Gln Glu Arg Ser Asp Val Ser Arg Gly Gln Ser Gly Ser Arg Ser
    1850                1855                1860

Val Ser Arg Gln Thr Arg Asn Glu Lys Gln Ser Gly Asp Gly Ser
    1865                1870                1875

Arg His Ser Gly Ser Arg His His Glu Ala Ser Ser Arg Ala Asp
    1880                1885                1890

Ser Ser Arg His Ser Gln Val Gly Gln Gly Gln Ser Ser Gly Pro
    1895                1900                1905

Arg Thr Ser Arg Asn Gln Gly Ser Ser Val Ser Gln Asp Ser Asp
    1910                1915                1920

Ser Gln Gly His Ser Glu Asp Ser Glu Arg Trp Ser Gly Ser Ala
    1925                1930                1935

Ser Arg Asn His Leu Gly Ser Ala Trp Glu Gln Ser Arg Asp Gly
    1940                1945                1950

Ser Arg His Pro Gly Ser His His Glu Asp Arg Ala Gly His Gly
    1955                1960                1965
```

-continued

His Ser Ala Asp Ser Ser Arg Gln Ser Gly Thr Arg His Thr Glu
    1970            1975                1980

Ser Ser Ser Arg Gly Gln Ala Ala Ser Ser His Glu Gln Ala Arg
    1985            1990                1995

Ser Ser Ala Gly Glu Arg His Gly Ser His His Gln Leu Gln Ser
    2000            2005                2010

Ala Asp Ser Ser Arg His Ser Gly Ile Gly His Gly Gln Ala Ser
    2015            2020                2025

Ser Ala Val Arg Asp Ser Gly His Arg Gly Tyr Ser Gly Ser Gln
    2030            2035                2040

Ala Ser Asp Ser Glu Gly His Ser Glu Asp Ser Asp Thr Gln Ser
    2045            2050                2055

Val Ser Ala Gln Gly Lys Ala Gly Pro His Gln Gln Ser His Lys
    2060            2065                2070

Glu Ser Ala Arg Gly Gln Ser Gly Glu Ser Ser Gly Arg Ser Gly
    2075            2080                2085

Ser Phe Leu Tyr Gln Val Ser Thr His Glu Gln Ser Glu Ser Thr
    2090            2095                2100

His Gly Gln Ser Ala Pro Ser Thr Gly Gly Arg Gln Gly Ser His
    2105            2110                2115

Tyr Asp Gln Ala Gln Asp Ser Ser Arg His Ser Ala Ser Gln Glu
    2120            2125                2130

Gly Gln Asp Thr Ile Arg Gly His Pro Gly Pro Ser Arg Gly Gly
    2135            2140                2145

Arg Gln Gly Ser His Gln Glu Gln Ser Val Asp Arg Ser Gly His
    2150            2155                2160

Ser Gly Ser His His Ser His Thr Thr Ser Gln Gly Arg Ser Asp
    2165            2170                2175

Ala Ser Arg Gly Gln Ser Gly Ser Arg Ser Ala Ser Arg Lys Thr
    2180            2185                2190

Tyr Asp Lys Glu Gln Ser Gly Asp Gly Ser Arg His Ser Gly Ser
    2195            2200                2205

His His His Glu Ala Ser Ser Trp Ala Asp Ser Ser Arg His Ser
    2210            2215                2220

Leu Val Gly Gln Gly Gln Ser Ser Gly Pro Arg Thr Ser Arg Pro
    2225            2230                2235

Arg Gly Ser Ser Val Ser Gln Asp Ser Asp Ser Glu Gly His Ser
    2240            2245                2250

Glu Asp Ser Glu Arg Arg Ser Gly Ser Ala Ser Arg Asn His His
    2255            2260                2265

Gly Ser Ala Gln Glu Gln Ser Arg Asp Gly Ser Arg His Pro Arg
    2270            2275                2280

Ser His His Glu Asp Arg Ala Gly His Gly His Ser Ala Glu Ser
    2285            2290                2295

Ser Arg Gln Ser Gly Thr His His Ala Glu Asn Ser Ser Gly Gly
    2300            2305                2310

Gln Ala Ala Ser Ser His Glu Gln Ala Arg Ser Ser Ala Gly Glu
    2315            2320                2325

Arg His Gly Ser His His Gln Gln Ser Ala Asp Ser Ser Arg His
    2330            2335                2340

Ser Gly Ile Gly His Gly Gln Ala Ser Ser Ala Val Arg Asp Ser
    2345            2350                2355

```
Gly His Arg Gly Ser Ser Gly Ser Gln Ala Ser Asp Ser Glu Gly
    2360                2365                2370

His Ser Glu Asp Ser Asp Thr Gln Ser Val Ser Ala His Gly Gln
    2375                2380                2385

Ala Gly Pro His Gln Gln Ser His Gln Glu Ser Thr Arg Gly Arg
    2390                2395                2400

Ser Ala Gly Arg Ser Gly Arg Ser Gly Ser Phe Leu Tyr Gln Val
    2405                2410                2415

Ser Thr His Glu Gln Ser Glu Ser Ala His Gly Arg Thr Gly Thr
    2420                2425                2430

Ser Thr Gly Gly Arg Gln Gly Ser His His Lys Gln Ala Arg Asp
    2435                2440                2445

Ser Ser Arg His Ser Thr Ser Gln Glu Gly Gln Asp Thr Ile His
    2450                2455                2460

Gly His Pro Gly Ser Ser Ser Gly Gly Arg Gln Gly Ser His Tyr
    2465                2470                2475

Glu Gln Leu Val Asp Arg Ser Gly His Ser Gly Ser His His Ser
    2480                2485                2490

His Thr Thr Ser Gln Gly Arg Ser Asp Ala Ser His Gly His Ser
    2495                2500                2505

Gly Ser Arg Ser Ala Ser Arg Gln Thr Arg Asn Asp Glu Gln Ser
    2510                2515                2520

Gly Asp Gly Ser Arg His Ser Gly Ser Arg His His Glu Ala Ser
    2525                2530                2535

Ser Arg Ala Asp Ser Ser Gly His Ser Gln Val Gly Gln Gly Gln
    2540                2545                2550

Ser Glu Gly Pro Arg Thr Ser Arg Asn Trp Gly Ser Ser Phe Ser
    2555                2560                2565

Gln Asp Ser Asp Ser Gln Gly His Ser Glu Asp Ser Glu Arg Trp
    2570                2575                2580

Ser Gly Ser Ala Ser Arg Asn His His Gly Ser Ala Gln Glu Gln
    2585                2590                2595

Leu Arg Asp Gly Ser Arg His Pro Arg Ser His Gln Glu Asp Arg
    2600                2605                2610

Ala Gly His Gly His Ser Ala Asp Ser Ser Arg Gln Ser Gly Thr
    2615                2620                2625

Arg His Thr Gln Thr Ser Ser Gly Gly Gln Ala Ala Ser Ser His
    2630                2635                2640

Glu Gln Ala Arg Ser Ser Ala Gly Glu Arg His Gly Ser His His
    2645                2650                2655

Gln Gln Ser Ala Asp Ser Ser Arg His Ser Gly Ile Gly His Gly
    2660                2665                2670

Gln Ala Ser Ser Ala Val Arg Asp Ser Gly His Arg Gly Tyr Ser
    2675                2680                2685

Gly Ser Gln Ala Ser Asp Asn Glu Gly His Ser Glu Asp Ser Asp
    2690                2695                2700

Thr Gln Ser Val Ser Ala His Gly Gln Ala Gly Ser His Gln Gln
    2705                2710                2715

Ser His Gln Glu Ser Ala Arg Gly Arg Ser Gly Glu Thr Ser Gly
    2720                2725                2730

His Ser Gly Ser Phe Leu Tyr Gln Val Ser Thr His Glu Gln Ser
    2735                2740                2745

Glu Ser Ser His Gly Trp Thr Gly Pro Ser Thr Arg Gly Arg Gln
```

-continued

```
            2750                2755                2760
Gly Ser Arg His Glu Gln Ala Gln Asp Ser Ser Arg His Ser Ala
            2765                2770                2775
Ser Gln Asp Gly Gln Asp Thr Ile Arg Gly His Pro Gly Ser Ser
            2780                2785                2790
Arg Gly Gly Arg Gln Gly Tyr His His Glu His Ser Val Asp Ser
            2795                2800                2805
Ser Gly His Ser Gly Ser His His Ser His Thr Thr Ser Gln Gly
            2810                2815                2820
Arg Ser Asp Ala Ser Arg Gly Gln Ser Gly Ser Arg Ser Ala Ser
            2825                2830                2835
Arg Thr Thr Arg Asn Glu Glu Gln Ser Gly Asp Gly Ser Arg His
            2840                2845                2850
Ser Gly Ser Arg His His Glu Ala Ser Thr His Ala Asp Ile Ser
            2855                2860                2865
Arg His Ser Gln Ala Val Gln Gly Gln Ser Glu Gly Ser Arg Arg
            2870                2875                2880
Ser Arg Arg Gln Gly Ser Ser Val Ser Gln Asp Ser Asp Ser Glu
            2885                2890                2895
Gly His Ser Glu Asp Ser Glu Arg Trp Ser Gly Ser Ala Ser Arg
            2900                2905                2910
Asn His His Gly Ser Ala Gln Glu Gln Leu Arg Asp Gly Ser Arg
            2915                2920                2925
His Pro Arg Ser His Gln Glu Asp Arg Ala Gly His Gly His Ser
            2930                2935                2940
Ala Asp Ser Ser Arg Gln Ser Gly Thr Arg His Thr Gln Thr Ser
            2945                2950                2955
Ser Gly Gly Gln Ala Ala Ser Ser His Glu Gln Ala Arg Ser Ser
            2960                2965                2970
Ala Gly Glu Arg His Gly Ser His His Gln Gln Ser Ala Asp Ser
            2975                2980                2985
Ser Arg His Ser Gly Ile Gly His Gly Gln Ala Ser Ser Ala Val
            2990                2995                3000
Arg Asp Ser Gly His Arg Gly Tyr Ser Gly Ser Gln Ala Ser Asp
            3005                3010                3015
Asn Glu Gly His Ser Glu Asp Ser Asp Thr Gln Ser Val Ser Ala
            3020                3025                3030
His Gly Gln Ala Gly Ser Gln Gln Ser His Gln Glu Ser Ala
            3035                3040                3045
Arg Gly Arg Ser Gly Glu Thr Ser Gly His Ser Gly Ser Phe Leu
            3050                3055                3060
Tyr Gln Val Ser Thr His Glu Gln Ser Glu Ser Ser His Gly Trp
            3065                3070                3075
Thr Gly Pro Ser Thr Arg Gly Arg Gln Gly Ser Arg His Glu Gln
            3080                3085                3090
Ala Gln Asp Ser Ser Arg His Ser Ala Ser Gln Tyr Gly Gln Asp
            3095                3100                3105
Thr Ile Arg Gly His Pro Gly Ser Ser Arg Gly Gly Arg Gln Gly
            3110                3115                3120
Tyr His His Glu His Ser Val Asp Ser Ser Gly His Ser Gly Ser
            3125                3130                3135
His His Ser His Thr Thr Ser Gln Gly Arg Ser Asp Ala Ser Arg
            3140                3145                3150
```

-continued

```
Gly Gln Ser Gly Ser Arg Ser Ala Ser Arg Thr Thr Arg Asn Glu
    3155                3160                3165
Glu Gln Ser Gly Asp Ser Ser Arg His Ser Val Ser Arg His His
    3170                3175                3180
Glu Ala Ser Thr His Ala Asp Ile Ser Arg His Ser Gln Ala Val
    3185                3190                3195
Gln Gly Gln Ser Glu Gly Ser Arg Arg Ser Arg Arg Gln Gly Ser
    3200                3205                3210
Ser Val Ser Gln Asp Ser Asp Ser Glu Gly His Ser Glu Asp Ser
    3215                3220                3225
Glu Arg Trp Ser Gly Ser Ala Ser Arg Asn His Arg Gly Ser Val
    3230                3235                3240
Gln Glu Gln Ser Arg His Gly Ser Arg His Pro Arg Ser His His
    3245                3250                3255
Glu Asp Arg Ala Gly His Gly His Ser Ala Asp Arg Ser Arg Gln
    3260                3265                3270
Ser Gly Thr Arg His Ala Glu Thr Ser Ser Gly Gly Gln Ala Ala
    3275                3280                3285
Ser Ser His Glu Gln Ala Arg Ser Ser Pro Gly Glu Arg His Gly
    3290                3295                3300
Ser Arg His Gln Gln Ser Ala Asp Ser Ser Arg His Ser Gly Ile
    3305                3310                3315
Pro Arg Gly Gln Ala Ser Ser Ala Val Arg Asp Ser Arg His Trp
    3320                3325                3330
Gly Ser Ser Gly Ser Gln Ala Ser Asp Ser Glu Gly His Ser Glu
    3335                3340                3345
Glu Ser Asp Thr Gln Ser Val Ser Gly His Gly Gln Ala Gly Pro
    3350                3355                3360
His Gln Gln Ser His Gln Glu Ser Ala Arg Asp Arg Ser Gly Gly
    3365                3370                3375
Arg Ser Gly Arg Ser Gly Ser Phe Leu Tyr Gln Val Ser Thr His
    3380                3385                3390
Glu Gln Ser Glu Ser Ala His Gly Arg Thr Arg Thr Ser Thr Gly
    3395                3400                3405
Arg Arg Gln Gly Ser His His Glu Gln Ala Arg Asp Ser Ser Arg
    3410                3415                3420
His Ser Ala Ser Gln Glu Gly Gln Asp Thr Ile Arg Gly His Pro
    3425                3430                3435
Gly Ser Ser Arg Arg Gly Arg Gln Gly Ser His Tyr Glu Gln Ser
    3440                3445                3450
Val Asp Arg Ser Gly His Ser Gly Ser His His Ser His Thr Thr
    3455                3460                3465
Ser Gln Gly Arg Ser Asp Ala Ser Arg Gly Gln Ser Gly Ser Arg
    3470                3475                3480
Ser Ala Ser Arg Gln Thr Arg Asn Asp Glu Gln Ser Gly Asp Gly
    3485                3490                3495
Ser Arg His Ser Trp Ser His His His Glu Ala Ser Thr Gln Ala
    3500                3505                3510
Asp Ser Ser Arg His Ser Gln Ser Gly Gln Gly Gln Ser Ala Gly
    3515                3520                3525
Pro Arg Thr Ser Arg Asn Gln Gly Ser Ser Val Ser Gln Asp Ser
    3530                3535                3540
```

-continued

Asp Ser Gln Gly His Ser Glu Asp Ser Glu Arg Trp Ser Gly Ser
3545                3550                3555

Ala Ser Arg Asn His Arg Gly Ser Ala Gln Glu Gln Ser Arg Asp
3560                3565                3570

Gly Ser Arg His Pro Thr Ser His His Glu Asp Arg Ala Gly His
3575                3580                3585

Gly His Ser Ala Glu Ser Ser Arg Gln Ser Gly Thr His His Ala
3590                3595                3600

Glu Asn Ser Ser Gly Gly Gln Ala Ala Ser Ser His Glu Gln Ala
3605                3610                3615

Arg Ser Ser Ala Gly Glu Arg His Gly Ser His His Gln Gln Ser
3620                3625                3630

Ala Asp Ser Ser Arg His Ser Gly Ile Gly His Gly Gln Ala Ser
3635                3640                3645

Ser Ala Val Arg Asp Ser Gly His Arg Gly Ser Ser Gly Ser Gln
3650                3655                3660

Ala Ser Asp Ser Glu Gly His Ser Glu Asp Ser Asp Thr Gln Ser
3665                3670                3675

Val Ser Ala His Gly Gln Ala Gly Pro His Gln Gln Ser His Gln
3680                3685                3690

Glu Ser Thr Arg Gly Arg Ser Ala Gly Arg Ser Gly Arg Ser Gly
3695                3700                3705

Ser Phe Leu Tyr Gln Val Ser Thr His Glu Gln Ser Glu Ser Ala
3710                3715                3720

His Gly Arg Ala Gly Pro Ser Thr Gly Gly Arg Gln Gly Ser Arg
3725                3730                3735

His Glu Gln Ala Arg Asp Ser Ser Arg His Ser Ala Ser Gln Glu
3740                3745                3750

Gly Gln Asp Thr Ile Arg Gly His Pro Gly Ser Arg Arg Gly Gly
3755                3760                3765

Arg Gln Gly Ser Tyr His Glu Gln Ser Val Asp Arg Ser Gly His
3770                3775                3780

Ser Gly Ser His His Ser His Thr Thr Ser Gln Gly Arg Ser Asp
3785                3790                3795

Ala Ser His Gly Gln Ser Gly Ser Arg Ser Ala Ser Arg Glu Thr
3800                3805                3810

Arg Asn Glu Glu Gln Ser Gly Asp Gly Ser Arg His Ser Gly Ser
3815                3820                3825

Arg His His Glu Ala Ser Thr Gln Ala Asp Ser Ser Arg His Ser
3830                3835                3840

Gln Ser Gly Gln Gly Glu Ser Ala Gly Ser Arg Arg Ser Arg Arg
3845                3850                3855

Gln Gly Ser Ser Val Ser Gln Asp Ser Asp Ser Glu Ala Tyr Pro
3860                3865                3870

Glu Asp Ser Glu Arg Arg Ser Glu Ser Ala Ser Arg Asn His His
3875                3880                3885

Gly Ser Ser Arg Glu Gln Ser Arg Asp Gly Ser Arg His Pro Gly
3890                3895                3900

Ser Ser His Arg Asp Thr Ala Ser His Val Gln Ser Ser Pro Val
3905                3910                3915

Gln Ser Asp Ser Ser Thr Ala Lys Glu His Gly His Phe Ser Ser
3920                3925                3930

Leu Ser Gln Asp Ser Ala Tyr His Ser Gly Ile Gln Ser Arg Gly

```
                    3935                3940                3945

Ser Pro His Ser Ser Ser  Tyr His Tyr Gln  Ser Glu Gly Thr
    3950                3955                3960

Glu Arg Gln Lys Gly Gln  Ser Gly Leu Val Trp  Arg His Gly Ser
    3965                3970                3975

Tyr Gly Ser Ala Asp Tyr  Asp Tyr Gly Glu Ser  Gly Phe Arg His
    3980                3985                3990

Ser Gln His Gly Ser Val  Ser Tyr Asn Ser Asn  Pro Val Val Phe
    3995                4000                4005

Lys Glu Arg Ser Asp Ile  Cys Lys Ala Ser Ala  Phe Gly Lys Asp
    4010                4015                4020

His Pro Arg Tyr Tyr Ala  Thr Tyr Ile Asn Lys  Asp Pro Gly Leu
    4025                4030                4035

Cys Gly His Ser Ser Asp  Ile Ser Lys Gln Leu  Gly Phe Ser Gln
    4040                4045                4050

Ser Gln Arg Tyr Tyr Tyr  Tyr Glu
    4055                4060

<210> SEQ ID NO 5
<211> LENGTH: 4061
<212> TYPE: PRT
<213> ORGANISM: Homo sapiens

<400> SEQUENCE: 5

Met Ser Thr Leu Leu Glu Asn Ile Phe Ala Ile Ile Asn Leu Phe Lys
1               5                   10                  15

Gln Tyr Ser Lys Lys Asp Lys Asn Thr Asp Thr Leu Ser Lys Lys Glu
                20                  25                  30

Leu Lys Glu Leu Leu Glu Lys Glu Phe Arg Gln Ile Leu Lys Asn Pro
            35                  40                  45

Asp Asp Pro Asp Met Val Asp Val Phe Met Asp His Leu Asp Ile Asp
        50                  55                  60

His Asn Lys Lys Ile Asp Phe Thr Glu Phe Leu Leu Met Val Phe Lys
65                  70                  75                  80

Leu Ala Gln Ala Tyr Tyr Glu Ser Thr Arg Lys Glu Asn Leu Pro Ile
                85                  90                  95

Ser Gly His Lys His Arg Lys His Ser His His Asp Lys His Glu Asp
                100                 105                 110

Asn Lys Gln Glu Glu Asn Lys Glu Asn Arg Lys Arg Pro Ser Ser Leu
            115                 120                 125

Glu Arg Arg Asn Asn Arg Lys Gly Asn Lys Gly Arg Ser Lys Ser Pro
        130                 135                 140

Arg Glu Thr Gly Gly Lys Arg His Glu Ser Ser Ser Glu Lys Lys Glu
145                 150                 155                 160

Arg Lys Gly Tyr Ser Pro Thr His Arg Glu Glu Glu Tyr Gly Lys Asn
                165                 170                 175

His His Asn Ser Ser Lys Lys Glu Lys Asn Lys Thr Glu Asn Thr Arg
                180                 185                 190

Leu Gly Asp Asn Arg Lys Arg Leu Ser Glu Arg Leu Glu Glu Lys Glu
            195                 200                 205

Asp Asn Glu Glu Gly Val Tyr Asp Tyr Glu Asn Thr Gly Arg Met Thr
        210                 215                 220

Gln Lys Trp Ile Gln Ser Gly His Ile Ala Thr Tyr Tyr Thr Ile Gln
225                 230                 235                 240
```

-continued

Asp Glu Ala Tyr Asp Thr Thr Asp Ser Leu Leu Glu Glu Asn Lys Ile
            245                 250                 255

Tyr Glu Arg Ser Arg Ser Ser Asp Gly Lys Ser Ser Ser Gln Val Asn
        260                 265                 270

Arg Ser Arg His Glu Asn Thr Ser Gln Val Pro Leu Gln Glu Ser Arg
        275                 280                 285

Thr Arg Lys Arg Arg Gly Ser Arg Val Ser Gln Asp Arg Asp Ser Glu
        290                 295                 300

Gly His Ser Glu Asp Glu Arg His Ser Gly Ser Ala Ser Arg Asn
305                 310                 315                 320

His His Gly Ser Ala Trp Glu Gln Ser Arg Asp Gly Ser Arg His Pro
                325                 330                 335

Arg Ser His Asp Glu Asp Arg Ala Ser His Gly His Ser Ala Asp Ser
            340                 345                 350

Ser Arg Gln Ser Gly Thr Arg His Ala Glu Thr Ser Ser Arg Gly Gln
        355                 360                 365

Thr Ala Ser Ser His Glu Gln Ala Arg Ser Ser Pro Gly Glu Arg His
    370                 375                 380

Gly Ser Gly His Gln Gln Ser Ala Asp Ser Ser Arg His Ser Ala Thr
385                 390                 395                 400

Gly Arg Gly Gln Ala Ser Ser Ala Val Ser Asp Arg Gly His Arg Gly
                405                 410                 415

Ser Ser Gly Ser Gln Ala Ser Asp Ser Glu Gly His Ser Glu Asn Ser
            420                 425                 430

Asp Thr Gln Ser Val Ser Gly His Gly Lys Ala Gly Leu Arg Gln Gln
        435                 440                 445

Ser His Gln Glu Ser Thr Arg Gly Arg Ser Gly Glu Arg Ser Gly Arg
    450                 455                 460

Ser Gly Ser Ser Leu Tyr Gln Val Ser Thr His Glu Gln Pro Asp Ser
465                 470                 475                 480

Ala His Gly Arg Thr Gly Thr Ser Thr Gly Arg Gln Gly Ser His
                485                 490                 495

His Glu Gln Ala Arg Asp Ser Ser Arg His Ser Ala Ser Gln Glu Gly
            500                 505                 510

Gln Asp Thr Ile Arg Gly His Pro Gly Ser Ser Arg Gly Gly Arg Gln
        515                 520                 525

Gly Ser His His Glu Gln Ser Val Asn Arg Ser Gly His Ser Gly Ser
    530                 535                 540

His His Ser His Thr Thr Ser Gln Gly Arg Ser Asp Ala Ser His Gly
545                 550                 555                 560

Gln Ser Gly Ser Arg Ser Ala Ser Arg Gln Thr Arg Asn Glu Glu Gln
                565                 570                 575

Ser Gly Asp Gly Thr Arg His Ser Gly Ser Arg His His Glu Ala Ser
            580                 585                 590

Ser Gln Ala Asp Ser Ser Arg His Ser Gln Val Gly Gln Gly Gln Ser
        595                 600                 605

Ser Gly Pro Arg Thr Ser Arg Asn Gln Gly Ser Ser Val Ser Gln Asp
    610                 615                 620

Ser Asp Ser Gln Gly His Ser Glu Asp Ser Glu Arg Trp Ser Gly Ser
625                 630                 635                 640

Ala Ser Arg Asn His His Gly Ser Ala Gln Glu Gln Ser Arg Asp Gly
                645                 650                 655

Ser Arg His Pro Arg Ser His His Glu Asp Arg Ala Gly His Gly His

```
              660                 665                 670
Ser Ala Asp Ser Ser Arg Lys Ser Gly Thr Arg His Thr Gln Asn Ser
            675                 680                 685

Ser Ser Gly Gln Ala Ala Ser Ser His Glu Gln Ala Arg Ser Ser Ala
            690                 695                 700

Gly Glu Arg His Gly Ser Arg His Gln Leu Gln Ser Ala Asp Ser Ser
705                 710                 715                 720

Arg His Ser Gly Thr Gly His Gly Gln Ala Ser Ser Ala Val Arg Asp
                725                 730                 735

Ser Gly His Arg Gly Ser Ser Gly Ser Gln Ala Thr Asp Ser Glu Gly
            740                 745                 750

His Ser Glu Asp Ser Asp Thr Gln Ser Val Ser Gly His Gly Gln Ala
            755                 760                 765

Gly His His Gln Gln Ser His Gln Glu Ser Ala Arg Asp Arg Ser Gly
            770                 775                 780

Glu Arg Ser Arg Arg Ser Gly Ser Phe Leu Tyr Gln Val Ser Thr His
785                 790                 795                 800

Lys Gln Ser Glu Ser Ser His Gly Trp Thr Gly Pro Ser Thr Gly Val
                805                 810                 815

Arg Gln Gly Ser His His Glu Gln Ala Arg Asp Asn Ser Arg His Ser
            820                 825                 830

Ala Ser Gln Asp Gly Gln Asp Thr Ile Arg Gly His Pro Gly Ser Ser
            835                 840                 845

Arg Arg Gly Arg Gln Gly Ser His His Glu Gln Ser Val Asp Arg Ser
850                 855                 860

Gly His Ser Gly Ser His His Ser His Thr Thr Ser Gln Gly Arg Ser
865                 870                 875                 880

Asp Ala Ser Arg Gly Gln Ser Gly Ser Arg Ser Ala Ser Arg Thr Thr
                885                 890                 895

Arg Asn Glu Glu Gln Ser Arg Asp Gly Ser Arg His Ser Gly Ser Arg
            900                 905                 910

His His Glu Ala Ser Ser His Ala Asp Ile Ser Arg His Ser Gln Ala
            915                 920                 925

Gly Gln Gly Gln Ser Glu Gly Ser Arg Thr Ser Arg Arg Gln Gly Ser
            930                 935                 940

Ser Val Ser Gln Asp Ser Asp Ser Glu Gly His Ser Glu Asp Ser Glu
945                 950                 955                 960

Arg Trp Ser Gly Ser Ala Ser Arg Asn His Arg Gly Ser Ala Gln Glu
                965                 970                 975

Gln Ser Arg His Gly Ser Arg His Pro Arg Ser His His Glu Asp Arg
            980                 985                 990

Ala Gly His Gly His Ser Ala Asp Ser Ser Arg Gln Ser Gly Thr Pro
            995                 1000                1005

His Ala Glu Thr Ser Ser Gly Gly Gln Ala Ala Ser Ser His Glu
            1010                1015                1020

Gln Ala Arg Ser Ser Pro Gly Glu Arg His Gly Ser Arg His Gln
            1025                1030                1035

Gln Ser Ala Asp Ser Ser Arg His Ser Gly Ile Pro Arg Arg Gln
            1040                1045                1050

Ala Ser Ser Ala Val Arg Asp Ser Gly His Trp Gly Ser Ser Gly
            1055                1060                1065

Ser Gln Ala Ser Asp Ser Glu Gly His Ser Glu Glu Ser Asp Thr
            1070                1075                1080
```

```
Gln Ser Val Ser Gly His Gly Gln Asp Gly Pro His Gln Gln Ser
    1085            1090            1095

His Gln Glu Ser Ala Arg Asp Trp Ser Gly Gly Arg Ser Gly Arg
    1100            1105            1110

Ser Gly Ser Phe Ile Tyr Gln Val Ser Thr His Glu Gln Ser Glu
    1115            1120            1125

Ser Ala His Gly Arg Thr Arg Thr Ser Thr Gly Arg Arg Gln Gly
    1130            1135            1140

Ser His His Glu Gln Ala Arg Asp Ser Ser Arg His Ser Ala Ser
    1145            1150            1155

Gln Glu Gly Gln Asp Thr Ile Arg Ala His Pro Gly Ser Arg Arg
    1160            1165            1170

Gly Gly Arg Gln Gly Ser His His Glu Gln Ser Val Asp Arg Ser
    1175            1180            1185

Gly His Ser Gly Ser His His Ser His Thr Thr Ser Gln Gly Arg
    1190            1195            1200

Ser Asp Ala Ser His Gly Gln Ser Gly Ser Arg Ser Ala Ser Arg
    1205            1210            1215

Gln Thr Arg Lys Asp Lys Gln Ser Gly Asp Gly Ser Arg His Ser
    1220            1225            1230

Gly Ser Arg His His Glu Ala Ala Ser Trp Ala Asp Ser Ser Arg
    1235            1240            1245

His Ser Gln Val Gly Gln Glu Gln Ser Gly Ser Arg Thr Ser
    1250            1255            1260

Arg His Gln Gly Ser Ser Val Ser Gln Asp Ser Asp Ser Glu Arg
    1265            1270            1275

His Ser Asp Asp Ser Glu Arg Leu Ser Gly Ser Ala Ser Arg Asn
    1280            1285            1290

His His Gly Ser Ser Arg Glu Gln Ser Arg Asp Gly Ser Arg His
    1295            1300            1305

Pro Gly Phe His Gln Glu Asp Arg Ala Ser His Gly His Ser Ala
    1310            1315            1320

Asp Ser Ser Arg Gln Ser Gly Thr His Thr Glu Ser Ser Ser
    1325            1330            1335

His Gly Gln Ala Val Ser Ser His Glu Gln Ala Arg Ser Ser Pro
    1340            1345            1350

Gly Glu Arg His Gly Ser Arg His Gln Gln Ser Ala Asp Ser Ser
    1355            1360            1365

Arg His Ser Gly Ile Gly His Arg Gln Ala Ser Ala Val Arg
    1370            1375            1380

Asp Ser Gly His Arg Gly Ser Gly Ser Gln Val Thr Asn Ser
    1385            1390            1395

Glu Gly His Ser Glu Asp Ser Asp Thr Gln Ser Val Ser Ala His
    1400            1405            1410

Gly Gln Ala Gly Pro His Gln Gln Ser His Lys Glu Ser Ala Arg
    1415            1420            1425

Gly Gln Ser Gly Glu Ser Ser Gly Arg Ser Arg Ser Phe Leu Tyr
    1430            1435            1440

Gln Val Ser Ser His Glu Gln Ser Glu Ser Thr His Gly Gln Thr
    1445            1450            1455

Ala Pro Ser Thr Gly Gly Arg Gln Gly Ser Arg His Glu Gln Ala
    1460            1465            1470
```

```
Arg Asn Ser Ser Arg His Ser Ala Ser Gln Asp Gly Gln Asp Thr
1475                1480                1485

Ile Arg Gly His Pro Gly Ser Ser Arg Gly Gly Arg Gln Gly Ser
1490                1495                1500

Tyr His Glu Gln Ser Val Asp Arg Ser Gly His Ser Gly Tyr His
1505                1510                1515

His Ser His Thr Thr Pro Gln Gly Arg Ser Asp Ala Ser His Gly
1520                1525                1530

Gln Ser Gly Pro Arg Ser Ala Ser Arg Gln Thr Arg Asn Glu Glu
1535                1540                1545

Gln Ser Gly Asp Gly Ser Arg His Ser Gly Ser Arg His His Glu
1550                1555                1560

Pro Ser Thr Arg Ala Gly Ser Ser Arg His Ser Gln Val Gly Gln
1565                1570                1575

Gly Glu Ser Ala Gly Ser Lys Thr Ser Arg Arg Gln Gly Ser Ser
1580                1585                1590

Val Ser Gln Asp Arg Asp Ser Glu Gly His Ser Glu Asp Ser Glu
1595                1600                1605

Arg Arg Ser Glu Ser Ala Ser Arg Asn His Tyr Gly Ser Ala Arg
1610                1615                1620

Glu Gln Ser Arg His Gly Ser Arg Asn Pro Arg Ser His Gln Glu
1625                1630                1635

Asp Arg Ala Ser His Gly His Ser Ala Glu Ser Ser Arg Gln Ser
1640                1645                1650

Gly Thr Arg His Ala Glu Thr Ser Ser Gly Gly Gln Ala Ala Ser
1655                1660                1665

Ser Gln Glu Gln Ala Arg Ser Ser Pro Gly Glu Arg His Gly Ser
1670                1675                1680

Arg His Gln Gln Ser Ala Asp Ser Ser Thr Asp Ser Gly Thr Gly
1685                1690                1695

Arg Arg Gln Asp Ser Ser Val Val Gly Asp Ser Gly Asn Arg Gly
1700                1705                1710

Ser Ser Gly Ser Gln Ala Ser Asp Ser Glu Gly His Ser Glu Glu
1715                1720                1725

Ser Asp Thr Gln Ser Val Ser Ala His Gly Gln Ala Gly Pro His
1730                1735                1740

Gln Gln Ser His Gln Glu Ser Thr Arg Gly Gln Ser Gly Glu Arg
1745                1750                1755

Ser Gly Arg Ser Gly Ser Phe Leu Tyr Gln Val Ser Thr His Glu
1760                1765                1770

Gln Ser Glu Ser Ala His Gly Arg Thr Gly Pro Ser Thr Gly Gly
1775                1780                1785

Arg Gln Arg Ser Arg His Glu Gln Ala Arg Asp Ser Ser Arg His
1790                1795                1800

Ser Ala Ser Gln Glu Gly Gln Asp Thr Ile Arg Gly His Pro Gly
1805                1810                1815

Ser Ser Arg Gly Gly Arg Gln Gly Ser His Tyr Glu Gln Ser Val
1820                1825                1830

Asp Ser Ser Gly His Ser Gly Ser His His Ser His Thr Thr Ser
1835                1840                1845

Gln Glu Arg Ser Asp Val Ser Arg Gly Gln Ser Gly Ser Arg Ser
1850                1855                1860

Val Ser Arg Gln Thr Arg Asn Glu Lys Gln Ser Gly Asp Gly Ser
```

```
            1865                1870                1875

Arg His Ser Gly Ser Arg His His Glu Ala Ser Ser Arg Ala Asp
            1880                1885                1890

Ser Ser Arg His Ser Gln Val Gly Gln Gly Gln Ser Ser Gly Pro
            1895                1900                1905

Arg Thr Ser Arg Asn Gln Gly Ser Ser Val Ser Gln Asp Ser Asp
            1910                1915                1920

Ser Gln Gly His Ser Glu Asp Ser Glu Arg Trp Ser Gly Ser Ala
            1925                1930                1935

Ser Arg Asn His Leu Gly Ser Ala Trp Glu Gln Ser Arg Asp Gly
            1940                1945                1950

Ser Arg His Pro Gly Ser His His Glu Asp Arg Ala Gly His Gly
            1955                1960                1965

His Ser Ala Asp Ser Ser Arg Gln Ser Gly Thr Arg His Thr Glu
            1970                1975                1980

Ser Ser Ser Arg Gly Gln Ala Ala Ser Ser His Glu Gln Ala Arg
            1985                1990                1995

Ser Ser Ala Gly Glu Arg His Gly Ser His His Gln Leu Gln Ser
            2000                2005                2010

Ala Asp Ser Ser Arg His Ser Gly Ile Gly His Gly Gln Ala Ser
            2015                2020                2025

Ser Ala Val Arg Asp Ser Gly His Arg Gly Tyr Ser Gly Ser Gln
            2030                2035                2040

Ala Ser Asp Ser Glu Gly His Ser Glu Asp Ser Asp Thr Gln Ser
            2045                2050                2055

Val Ser Ala Gln Gly Lys Ala Gly Pro His Gln Gln Ser His Lys
            2060                2065                2070

Glu Ser Ala Arg Gly Gln Ser Gly Glu Ser Ser Gly Arg Ser Gly
            2075                2080                2085

Ser Phe Leu Tyr Gln Val Ser Thr His Glu Gln Ser Glu Ser Thr
            2090                2095                2100

His Gly Gln Ser Ala Pro Ser Thr Gly Gly Arg Gln Gly Ser His
            2105                2110                2115

Tyr Asp Gln Ala Gln Asp Ser Ser Arg His Ser Ala Ser Gln Glu
            2120                2125                2130

Gly Gln Asp Thr Ile Arg Gly His Pro Gly Pro Ser Arg Gly Gly
            2135                2140                2145

Arg Gln Gly Ser His Gln Glu Gln Ser Val Asp Arg Ser Gly His
            2150                2155                2160

Ser Gly Ser His His Ser His Thr Thr Ser Gln Gly Arg Ser Asp
            2165                2170                2175

Ala Ser Arg Gly Gln Ser Gly Ser Arg Ser Ala Ser Arg Lys Thr
            2180                2185                2190

Tyr Asp Lys Glu Gln Ser Gly Asp Gly Ser Arg His Ser Gly Ser
            2195                2200                2205

His His His Glu Ala Ser Ser Trp Ala Asp Ser Ser Arg His Ser
            2210                2215                2220

Leu Val Gly Gln Gly Gln Ser Ser Gly Pro Arg Thr Ser Arg Pro
            2225                2230                2235

Arg Gly Ser Ser Val Ser Gln Asp Ser Asp Ser Glu Gly His Ser
            2240                2245                2250

Glu Asp Ser Glu Arg Arg Ser Gly Ser Ala Ser Arg Asn His His
            2255                2260                2265
```

-continued

```
Gly Ser Ala Gln Glu Gln Ser Arg Asp Gly Ser Arg His Pro Arg
    2270                2275                2280

Ser His His Glu Asp Arg Ala Gly His Gly His Ser Ala Glu Ser
    2285                2290                2295

Ser Arg Gln Ser Gly Thr His His Ala Glu Asn Ser Ser Gly Gly
    2300                2305                2310

Gln Ala Ala Ser Ser His Glu Gln Ala Arg Ser Ala Gly Glu
    2315                2320                2325

Arg His Gly Ser His His Gln Gln Ser Ala Asp Ser Ser Arg His
    2330                2335                2340

Ser Gly Ile Gly His Gly Gln Ala Ser Ser Ala Val Arg Asp Ser
    2345                2350                2355

Gly His Arg Gly Ser Ser Gly Ser Gln Ala Ser Asp Ser Glu Gly
    2360                2365                2370

His Ser Glu Asp Ser Asp Thr Gln Ser Val Ser Ala His Gly Gln
    2375                2380                2385

Ala Gly Pro His Gln Gln Ser His Gln Glu Ser Thr Arg Gly Arg
    2390                2395                2400

Ser Ala Gly Arg Ser Gly Arg Ser Gly Ser Phe Leu Tyr Gln Val
    2405                2410                2415

Ser Thr His Glu Gln Ser Glu Ser Ala His Gly Arg Thr Gly Thr
    2420                2425                2430

Ser Thr Gly Gly Arg Gln Gly Ser His His Lys Gln Ala Arg Asp
    2435                2440                2445

Ser Ser Arg His Ser Thr Ser Gln Glu Gly Gln Asp Thr Ile His
    2450                2455                2460

Gly His Pro Gly Ser Ser Ser Gly Gly Arg Gln Gly Ser His Tyr
    2465                2470                2475

Glu Gln Leu Val Asp Arg Ser Gly His Ser Gly Ser His His Ser
    2480                2485                2490

His Thr Thr Ser Gln Gly Arg Ser Asp Ala Ser His Gly His Ser
    2495                2500                2505

Gly Ser Arg Ser Ala Ser Arg Gln Thr Arg Asn Asp Glu Gln Ser
    2510                2515                2520

Gly Asp Gly Ser Arg His Ser Gly Ser Arg His His Glu Ala Ser
    2525                2530                2535

Ser Arg Ala Asp Ser Ser Gly His Ser Gln Val Gly Gln Gly Gln
    2540                2545                2550

Ser Glu Gly Pro Arg Thr Ser Arg Asn Trp Gly Ser Ser Phe Ser
    2555                2560                2565

Gln Asp Ser Asp Ser Gln Gly His Ser Glu Asp Ser Glu Arg Trp
    2570                2575                2580

Ser Gly Ser Ala Ser Arg Asn His His Gly Ser Ala Gln Glu Gln
    2585                2590                2595

Leu Arg Asp Gly Ser Arg His Pro Arg Ser His Gln Glu Asp Arg
    2600                2605                2610

Ala Gly His Gly His Ser Ala Asp Ser Ser Arg Gln Ser Gly Thr
    2615                2620                2625

Arg His Thr Gln Thr Ser Ser Gly Gly Gln Ala Ala Ser Ser His
    2630                2635                2640

Glu Gln Ala Arg Ser Ser Ala Gly Glu Arg His Gly Ser His His
    2645                2650                2655
```

-continued

```
Gln Gln Ser Ala Asp Ser Ser Arg His Ser Gly Ile Gly His Gly
2660                2665                2670

Gln Ala Ser Ser Ala Val Arg Asp Ser Gly His Arg Gly Tyr Ser
2675                2680                2685

Gly Ser Gln Ala Ser Asp Asn Glu Gly His Ser Glu Asp Ser Asp
2690                2695                2700

Thr Gln Ser Val Ser Ala His Gly Gln Ala Gly Ser His Gln Gln
2705                2710                2715

Ser His Gln Glu Ser Ala Arg Gly Arg Ser Gly Glu Thr Ser Gly
2720                2725                2730

His Ser Gly Ser Phe Leu Tyr Gln Val Ser Thr His Glu Gln Ser
2735                2740                2745

Glu Ser Ser His Gly Trp Thr Gly Pro Ser Thr Arg Gly Arg Gln
2750                2755                2760

Gly Ser Arg His Glu Gln Ala Gln Asp Ser Ser Arg His Ser Ala
2765                2770                2775

Ser Gln Asp Gly Gln Asp Thr Ile Arg Gly His Pro Gly Ser Ser
2780                2785                2790

Arg Gly Gly Arg Gln Gly Tyr His His Glu His Ser Val Asp Ser
2795                2800                2805

Ser Gly His Ser Gly Ser His His Ser His Thr Thr Ser Gln Gly
2810                2815                2820

Arg Ser Asp Ala Ser Arg Gly Gln Ser Gly Ser Arg Ser Ala Ser
2825                2830                2835

Arg Thr Thr Arg Asn Glu Glu Gln Ser Gly Asp Gly Ser Arg His
2840                2845                2850

Ser Gly Ser Arg His His Glu Ala Ser Thr His Ala Asp Ile Ser
2855                2860                2865

Arg His Ser Gln Ala Val Gln Gly Gln Ser Glu Gly Ser Arg Arg
2870                2875                2880

Ser Arg Arg Gln Gly Ser Ser Val Ser Gln Asp Ser Asp Ser Glu
2885                2890                2895

Gly His Ser Glu Asp Ser Glu Arg Trp Ser Gly Ser Ala Ser Arg
2900                2905                2910

Asn His His Gly Ser Ala Gln Glu Gln Leu Arg Asp Gly Ser Arg
2915                2920                2925

His Pro Arg Ser His Gln Glu Asp Arg Ala Gly His Gly His Ser
2930                2935                2940

Ala Asp Ser Ser Arg Gln Ser Gly Thr Arg His Thr Gln Thr Ser
2945                2950                2955

Ser Gly Gly Gln Ala Ala Ser His Glu Gln Ala Arg Ser Ser
2960                2965                2970

Ala Gly Glu Arg His Gly Ser His His Gln Gln Ser Ala Asp Ser
2975                2980                2985

Ser Arg His Ser Gly Ile Gly His Gly Gln Ala Ser Ser Ala Val
2990                2995                3000

Arg Asp Ser Gly His Arg Gly Tyr Ser Gly Ser Gln Ala Ser Asp
3005                3010                3015

Asn Glu Gly His Ser Glu Asp Ser Asp Thr Gln Ser Val Ser Ala
3020                3025                3030

His Gly Gln Ala Gly Ser His Gln Gln Ser His Gln Glu Ser Ala
3035                3040                3045

Arg Gly Arg Ser Gly Glu Thr Ser Gly His Ser Gly Ser Phe Leu
```

|                 |                 |                 |
|-----------------|-----------------|-----------------|
| 3050            | 3055            | 3060            |

Tyr Gln Val Ser Thr His Glu Gln Ser Glu Ser Ser His Gly Trp
3065                3070                3075

Thr Gly Pro Ser Thr Arg Gly Arg Gln Gly Ser Arg His Glu Gln
3080                3085                3090

Ala Gln Asp Ser Ser Arg His Ser Ala Ser Gln Tyr Gly Gln Asp
3095                3100                3105

Thr Ile Arg Gly His Pro Gly Ser Ser Arg Gly Gly Arg Gln Gly
3110                3115                3120

Tyr His His Glu His Ser Val Asp Ser Ser Gly His Ser Gly Ser
3125                3130                3135

His His Ser His Thr Thr Ser Gln Gly Arg Ser Asp Ala Ser Arg
3140                3145                3150

Gly Gln Ser Gly Ser Arg Ser Ala Ser Arg Thr Thr Arg Asn Glu
3155                3160                3165

Glu Gln Ser Gly Asp Ser Ser Arg His Ser Val Ser Arg His His
3170                3175                3180

Glu Ala Ser Thr His Ala Asp Ile Ser Arg His Ser Gln Ala Val
3185                3190                3195

Gln Gly Gln Ser Glu Gly Ser Arg Arg Ser Arg Arg Gln Gly Ser
3200                3205                3210

Ser Val Ser Gln Asp Ser Asp Ser Glu Gly His Ser Glu Asp Ser
3215                3220                3225

Glu Arg Trp Ser Gly Ser Ala Ser Arg Asn His Arg Gly Ser Val
3230                3235                3240

Gln Glu Gln Ser Arg His Gly Ser Arg His Pro Arg Ser His His
3245                3250                3255

Glu Asp Arg Ala Gly His Gly His Ser Ala Asp Arg Ser Arg Gln
3260                3265                3270

Ser Gly Thr Arg His Ala Glu Thr Ser Ser Gly Gly Gln Ala Ala
3275                3280                3285

Ser Ser His Glu Gln Ala Arg Ser Ser Pro Gly Glu Arg His Gly
3290                3295                3300

Ser Arg His Gln Gln Ser Ala Asp Ser Ser Arg His Ser Gly Ile
3305                3310                3315

Pro Arg Gly Gln Ala Ser Ser Ala Val Arg Asp Ser Arg His Trp
3320                3325                3330

Gly Ser Ser Gly Ser Gln Ala Ser Asp Ser Glu Gly His Ser Glu
3335                3340                3345

Glu Ser Asp Thr Gln Ser Val Ser Gly His Gly Gln Ala Gly Pro
3350                3355                3360

His Gln Gln Ser His Gln Glu Ser Ala Arg Asp Arg Ser Gly Gly
3365                3370                3375

Arg Ser Gly Arg Ser Gly Ser Phe Leu Tyr Gln Val Ser Thr His
3380                3385                3390

Glu Gln Ser Glu Ser Ala His Gly Arg Thr Arg Thr Ser Thr Gly
3395                3400                3405

Arg Arg Gln Gly Ser His His Glu Gln Ala Arg Asp Ser Ser Arg
3410                3415                3420

His Ser Ala Ser Gln Glu Gly Gln Asp Thr Ile Arg Gly His Pro
3425                3430                3435

Gly Ser Ser Arg Arg Gly Arg Gln Gly Ser His Tyr Glu Gln Ser
3440                3445                3450

-continued

Val Asp Arg Ser Gly His Ser Gly Ser His Ser His Thr Thr
3455                3460                3465

Ser Gln Gly Arg Ser Asp Ala Ser Arg Gly Gln Ser Gly Ser Arg
3470                3475                3480

Ser Ala Ser Arg Gln Thr Arg Asn Asp Glu Gln Ser Gly Asp Gly
3485                3490                3495

Ser Arg His Ser Trp Ser His His Glu Ala Ser Thr Gln Ala
3500                3505                3510

Asp Ser Ser Arg His Ser Gln Ser Gly Gln Gly Gln Ser Ala Gly
3515                3520                3525

Pro Arg Thr Ser Arg Asn Gln Gly Ser Ser Val Ser Gln Asp Ser
3530                3535                3540

Asp Ser Gln Gly His Ser Glu Asp Ser Glu Arg Trp Ser Gly Ser
3545                3550                3555

Ala Ser Arg Asn His Arg Gly Ser Ala Gln Glu Gln Ser Arg Asp
3560                3565                3570

Gly Ser Arg His Pro Thr Ser His His Glu Asp Arg Ala Gly His
3575                3580                3585

Gly His Ser Ala Glu Ser Ser Arg Gln Ser Gly Thr His His Ala
3590                3595                3600

Glu Asn Ser Ser Gly Gly Gln Ala Ala Ser Ser His Glu Gln Ala
3605                3610                3615

Arg Ser Ser Ala Gly Glu Arg His Gly Ser His His Gln Gln Ser
3620                3625                3630

Ala Asp Ser Ser Arg His Ser Gly Ile Gly His Gly Gln Ala Ser
3635                3640                3645

Ser Ala Val Arg Asp Ser Gly His Arg Gly Ser Ser Gly Ser Gln
3650                3655                3660

Ala Ser Asp Ser Glu Gly His Ser Glu Asp Ser Asp Thr Gln Ser
3665                3670                3675

Val Ser Ala His Gly Gln Ala Gly Pro His Gln Gln Ser His Gln
3680                3685                3690

Glu Ser Thr Arg Gly Arg Ser Ala Gly Arg Ser Gly Arg Ser Gly
3695                3700                3705

Ser Phe Leu Tyr Gln Val Ser Thr His Glu Gln Ser Glu Ser Ala
3710                3715                3720

His Gly Arg Ala Gly Pro Ser Thr Gly Gly Arg Gln Gly Ser Arg
3725                3730                3735

His Glu Gln Ala Arg Asp Ser Ser Arg His Ser Ala Ser Gln Glu
3740                3745                3750

Gly Gln Asp Thr Ile Arg Gly His Pro Gly Ser Arg Arg Gly Gly
3755                3760                3765

Arg Gln Gly Ser Tyr His Glu Gln Ser Val Asp Arg Ser Gly His
3770                3775                3780

Ser Gly Ser His His Ser His Thr Thr Ser Gln Gly Arg Ser Asp
3785                3790                3795

Ala Ser His Gly Gln Ser Gly Ser Arg Ser Ala Ser Arg Glu Thr
3800                3805                3810

Arg Asn Glu Glu Gln Ser Gly Asp Gly Ser Arg His Ser Gly Ser
3815                3820                3825

Arg His His Glu Ala Ser Thr Gln Ala Asp Ser Ser Arg His Ser
3830                3835                3840

Gln Ser Gly Gln Gly Glu Ser Ala Gly Ser Arg Arg Ser Arg Arg
    3845                3850                3855

Gln Gly Ser Ser Val Ser Gln Asp Ser Asp Ser Glu Ala Tyr Pro
    3860                3865                3870

Glu Asp Ser Glu Arg Arg Ser Glu Ser Ala Ser Arg Asn His His
    3875                3880                3885

Gly Ser Ser Arg Glu Gln Ser Arg Asp Gly Ser Arg His Pro Gly
    3890                3895                3900

Ser Ser His Arg Asp Thr Ala Ser His Val Gln Ser Ser Pro Val
    3905                3910                3915

Gln Ser Asp Ser Ser Thr Ala Lys Glu His Gly His Phe Ser Ser
    3920                3925                3930

Leu Ser Gln Asp Ser Ala Tyr His Ser Gly Ile Gln Ser Arg Gly
    3935                3940                3945

Ser Pro His Ser Ser Ser Tyr His Tyr Gln Ser Glu Gly Thr
    3950                3955                3960

Glu Arg Gln Lys Gly Gln Ser Gly Leu Val Trp Arg His Gly Ser
    3965                3970                3975

Tyr Gly Ser Ala Asp Tyr Asp Tyr Gly Glu Ser Gly Phe Arg His
    3980                3985                3990

Ser Gln His Gly Ser Val Ser Tyr Asn Ser Asn Pro Val Val Phe
    3995                4000                4005

Lys Glu Arg Ser Asp Ile Cys Lys Ala Ser Ala Phe Gly Lys Asp
    4010                4015                4020

His Pro Arg Tyr Tyr Ala Thr Tyr Ile Asn Lys Asp Pro Gly Leu
    4025                4030                4035

Cys Gly His Ser Ser Asp Ile Ser Lys Gln Leu Gly Phe Ser Gln
    4040                4045                4050

Ser Gln Arg Tyr Tyr Tyr Tyr Glu
    4055                4060

<210> SEQ ID NO 6
<211> LENGTH: 269
<212> TYPE: PRT
<213> ORGANISM: Mus musculus

<400> SEQUENCE: 6

Gly Ser Gly Phe Tyr Pro Val Tyr Tyr Tyr Glu Gln Glu His Ser
1               5                   10                  15

Glu Glu Glu Ser Asp Ser Gln His Gly His Gln His Glu Gln Arg
            20                  25                  30

Gly His Gln His Gln His Gln His Glu His Glu Gln Pro Glu Ser Gly
        35                  40                  45

His Arg Gln Gln Gln Ser Ser Gly Arg Gly His Gln Gly Ala His Gln
    50                  55                  60

Glu Gln Gly Arg Asp Ser Ala Arg Ser Arg Gly Ser Asn Gln Gly His
65                  70                  75                  80

Ser Ser Ser Arg His Gln Ala Asp Ser Pro Arg Val Ser Ala Arg Ser
                85                  90                  95

Gly Ser Gly Gly Arg Gly Gln Ser Pro Asp Ala Ser Gly Arg Ser Ser
            100                 105                 110

Asn Arg Arg Asp Arg Pro Arg Gln Pro Asn Pro Ser Gln Ser Ser Asp
        115                 120                 125

Ser Gln Val His Ser Gly Val Gln Val Glu Gly Arg Arg Gly Gln Ser
    130                 135                 140

Ser Ser Ala Asn Arg Arg Ala Gly Ser Ser Gly Ser Gly Val Gln
145                 150                 155                 160

Gly Ala Ser Ala Gly Gly Leu Ala Ala Asp Ala Ser Arg Arg Ser Gly
            165                 170                 175

Ala Arg Gln Gly Gln Ala Ser Ala Gln Gly Arg Ala Gly Ser Gln Gly
        180                 185                 190

Gln Ala Gln Gly Arg Val Gly Ser Ser Ala Asp Arg Gln Gly Arg Arg
    195                 200                 205

Gly Val Ser Glu Ser Gln Ala Ser Asp Ser Glu Gly His Ser Asp Phe
210                 215                 220

Ser Glu Gly Gln Ala Val Gly Ala His Arg Gln Ser Gly Ala Gly Gln
225                 230                 235                 240

Arg His Glu Gln Arg Ser Ser Arg Gly Gln His Gly Ser Gly Tyr Tyr
                245                 250                 255

Tyr Glu Gln Glu His Ser Glu Glu Ser Asp Ser Gln
        260                 265

<210> SEQ ID NO 7
<211> LENGTH: 554
<212> TYPE: PRT
<213> ORGANISM: Mus musculus

<400> SEQUENCE: 7

Met Ser Ala Leu Leu Glu Ser Ile Thr Ser Met Ile Glu Ile Phe Gln
1               5                   10                  15

Gln Tyr Ser Thr Ser Asp Lys Glu Glu Glu Thr Leu Ser Lys Glu Glu
            20                  25                  30

Leu Lys Glu Leu Leu Glu Gly Gln Leu Gln Ala Val Leu Lys Asn Pro
        35                  40                  45

Asp Asp Gln Asp Ile Ala Glu Val Phe Met Gln Met Leu Asp Val Asp
    50                  55                  60

His Asp Asp Lys Leu Asp Phe Ala Glu Tyr Leu Leu Leu Val Leu Lys
65                  70                  75                  80

Leu Ala Lys Ala Tyr Tyr Glu Ala Ser Lys Asn Glu Ser Phe Gln Thr
                85                  90                  95

His Gly Ser Asn Gly Arg Ser Lys Thr Asp Tyr Lys Gly Leu Glu Glu
            100                 105                 110

Glu Gly Glu Glu Gly Asn Glu Gln Asn Leu Arg Arg Arg His Gly Gly
        115                 120                 125

Thr Asp Gly Lys Arg Lys Ser Asp Arg Thr Arg Ser Pro Asn Gly Lys
    130                 135                 140

Arg Gly Lys Arg Gln Glu Ser Arg Cys Arg Ser Glu Gly Lys Asp Lys
145                 150                 155                 160

His Arg Arg Glu Pro Glu Lys His Arg His Gln Gln Asp Ser Lys Arg
                165                 170                 175

Lys Gln Arg His Gly Ser Gly Ser Thr Glu Arg Lys Asp Asn Arg Asn
            180                 185                 190

Lys Lys Asn Arg Gln Ser Lys Glu Arg Asn Tyr Asp Glu Ile Tyr Asp
        195                 200                 205

Asn Gly Lys Tyr Asn Glu Asp Trp Glu Ala Ser Tyr Asn Cys Tyr
    210                 215                 220

Tyr Lys Thr Gln Asn Thr Thr Leu Asp Gln Arg Glu Gly Asn Arg Arg
225                 230                 235                 240

Pro Arg Ala Asp Ser Gln Lys Glu Pro Gln Ser Phe His Gly Gln Ala

```
            245                 250                 255
Asp Asn Ser Asp Ser Glu Gly Gly Arg Gln Gln Ser His Ser Lys Pro
        260                 265                 270

Ser Pro Val Arg Ala Asp Gln Arg Arg Ser Arg Ala Gly Gln Ala Gly
    275                 280                 285

Ser Ser Lys Val Ser Ala Arg Ser Gly Ser Gly Arg Gly Gln Ser
290                 295                 300

Pro Asp Gly Ser Gly Arg Ser Ser Asn Arg Arg Asp Arg Pro Arg Gln
305                 310                 315                 320

Pro Ser Pro Ser Gln Ser Ser Asp Ser Gln Val His Ser Gly Val Gln
                325                 330                 335

Val Glu Gly Arg Arg Gly Gln Ser Ser Ala Asn Arg Arg Ala Gly
            340                 345                 350

Ser Ser Ser Gly Ser Gly Val Gln Gly Ala Ser Ala Gly Gly Leu Ala
        355                 360                 365

Ala Asp Ala Ser Arg Arg Thr Gly Ala Leu Gln Gly Gln Ala Ser Ala
    370                 375                 380

Gln Gly Arg Ala Gly Ser Gln Gly Gln Ala Gln Gly Arg Val Gly Ser
385                 390                 395                 400

Ser Ala Asp Arg Gln Gly Arg Arg Gly Val Ser Glu Ser Gln Ala Ser
                405                 410                 415

Asp Ser Glu Gly Gln Ser Asp Phe Ser Glu Gly Gln Ala Val Gly Ala
            420                 425                 430

His Arg Gln Ser Gly Ala Gly Gln Arg His Glu Gln Arg Ser Ser Arg
        435                 440                 445

Gly Gln Tyr Gly Ser Gly Phe Tyr Pro Val Tyr Tyr Tyr Glu Gln
    450                 455                 460

Glu His Ser Glu Glu Ser Asp Ser Gln His Gly His Gln His Glu
465                 470                 475                 480

Gln Gln Arg Gly His Gln His Gln His Glu His Glu Gln Pro
                485                 490                 495

Glu Ser Gly His Arg Gln Gln Gln Ser Ser Gly Arg Gly His Gln Gly
            500                 505                 510

Ala His Gln Glu Gln Gly Arg Asp Ser Ala Arg Ser Arg Gly Ser Asn
        515                 520                 525

Gln Gly His Ser Ser Arg His Gln Ala Asp Ser Pro Arg Val Ser
    530                 535                 540

Val Arg Ser Gly Ser Gly Gly Arg Gly Gln
545                 550

<210> SEQ ID NO 8
<211> LENGTH: 336
<212> TYPE: PRT
<213> ORGANISM: Mus musculus

<400> SEQUENCE: 8

Pro Asp Gly Ser Gly Arg Ser Ser Asn Arg Arg Asp Arg Pro Arg Gln
1               5                   10                  15

Leu Ser Pro Ser Gln Ser Ser Asp Ser Gln Val His Ser Gly Val Gln
            20                  25                  30

Val Glu Gly Arg Arg Gly His Ser Ser Ala Asn Arg Arg Ala Gly
        35                  40                  45

Ser Ser Ser Gly Ser Gly Val Gln Gly Ala Ser Ala Gly Gly Leu Ala
    50                  55                  60
```

-continued

```
Ala Asp Ala Ser Arg Arg Ser Gly Ala Arg Gln Gly Gln Ala Ser Ala
 65                  70                  75                  80

Gln Gly Arg Ala Gly Ser Gln Gly Gln Ala Gln Gly Arg Val Ser Ser
                 85                  90                  95

Ser Ala Asp Arg Gln Gly Arg Arg Gly Val Ser Glu Ser Arg Ala Ser
            100                 105                 110

Asp Ser Glu Gly His Ser Asp Phe Ser Glu Gly Gln Ala Val Gly Ala
        115                 120                 125

His Arg Gln Ser Gly Ala Gly Gln Arg His Glu Gln Arg Ser Ser Arg
    130                 135                 140

Gly Gln His Gly Ser Gly Tyr Tyr Tyr Glu Gln Glu His Ser Glu Glu
145                 150                 155                 160

Glu Ser Asp Ser Gln His Gln His Gly His Gln His Glu Gln Gln Arg
                165                 170                 175

Gly His Gln His Gln His Gln His Gln His Glu His Glu Gln Pro Glu
            180                 185                 190

Ser Gly His Arg Gln Gln Ser Ser Gly Arg Gly His Gln Gly Ala
        195                 200                 205

His Gln Glu Gln Gly Arg Asp Ser Ala Arg Pro Arg Gly Ser Asn Gln
    210                 215                 220

Gly His Ser Ser Ser Arg His Gln Ala Asp Ser Pro Arg Val Ser Ala
225                 230                 235                 240

Arg Ser Gly Ser Gly Arg Gly Gln Ser Pro Asp Ala Ser Gly Arg
                245                 250                 255

Ser Ser Asn Arg Arg Asp Arg Pro Arg Gln Pro Ser Pro Ser Gln Ser
            260                 265                 270

Ser Asp Ser Gln Val His Ser Gly Val Gln Val Glu Ala Gln Arg Gly
        275                 280                 285

Gln Ser Ser Ser Ala Asn Arg Arg Ala Gly Ser Ser Gly Ser Gly
    290                 295                 300

Val Gln Gly Ala Ala Ala Ser Gly Gln Gly Gly Tyr Glu Ser Ile Phe
305                 310                 315                 320

Thr Ala Lys His Leu Asp Phe Asn Gln Ser His Ser Tyr Tyr Tyr Tyr
                325                 330                 335

<210> SEQ ID NO 9
<211> LENGTH: 250
<212> TYPE: PRT
<213> ORGANISM: Mus musculus

<400> SEQUENCE: 9

Gly Gly Leu Ala Ala Asp Ala Ser Arg Arg Ser Gly Ala Leu Gln Gly
 1               5                  10                  15

Gln Ala Ser Ala Gln Gly Arg Ala Gly Ser Gln Gly Gln Ala Gln Gly
                20                  25                  30

Arg Val Gly Ser Ser Ala Asp Arg Gln Gly Arg Arg Gly Val Ser Glu
            35                  40                  45

Ser Gln Ala Ser Asp Ser Glu Gly His Ser Asp Phe Ser Glu Gly Gln
        50                  55                  60

Ala Val Gly Ala His Arg Gln Ser Gly Ala Gly Gln Arg His Glu Gln
 65                  70                  75                  80

Arg Ser Ser Arg Gly Gln His Gly Ser Gly Tyr Tyr Tyr Glu Gln Glu
                 85                  90                  95

His Ser Glu Glu Glu Ser Asp Ser Gln His Gln His Gly His Gln His
            100                 105                 110
```

```
Glu Gln Gln Arg Gly His Gln His Gln His Gln His Glu His
        115                 120                 125

Glu Gln Pro Glu Ser Gly His Arg Gln Gln Ser Ser Gly Arg Gly
130                 135                 140

His Gln Gly Ala His Gln Glu Gln Gly Arg Asp Ser Ala Arg Ser Arg
145                 150                 155                 160

Gly Ser Asn Gln Gly His Ser Ser Arg His Gln Ala Asp Ser Pro
                165                 170                 175

Arg Val Ser Ala Arg Ser Gly Ser Gly Arg Gly Gln Ser Pro Asp
                180                 185                 190

Ala Ser Gly Arg Ser Ser Asn Arg Arg Asp Arg Pro Arg Gln Pro Ser
            195                 200                 205

Pro Ser Gln Ser Ser Asp Ser Gln Val His Ser Gly Val Gln Val Glu
210                 215                 220

Gly Arg Arg Gly Gln Ser Ser Ala Asn Arg Arg Ala Gly Ser Ser
225                 230                 235                 240

Ser Ser Ser Gly Val Gln Gly Ala Ser Ala
                245                 250

<210> SEQ ID NO 10
<211> LENGTH: 255
<212> TYPE: PRT
<213> ORGANISM: Mus musculus

<400> SEQUENCE: 10

Gly Gly Leu Ala Ala Asp Ala Ser Arg Ser Gly Ala Arg Gln Gly
1               5                   10                  15

Gln Ala Ser Ala Gln Gly Arg Ala Gly Ser Gln Gly Gln Ala Gln Gly
                20                  25                  30

Arg Val Gly Ser Ser Ala Asp Arg Gln Gly Arg Arg Gly Val Ser Glu
            35                  40                  45

Ser Gln Ala Ser Asp Ser Glu Gly His Ser Asp Phe Ser Glu Gly Gln
    50                  55                  60

Ala Val Gly Ala His Arg Gln Ser Gly Ala Gly Gln Arg His Glu Gln
65                  70                  75                  80

Arg Ser Ser Arg Gly Gln His Gly Ser Gly Phe Tyr Pro Val Tyr Tyr
                85                  90                  95

Tyr Tyr Glu Gln Glu His Ser Glu Glu Glu Ser Asp Ser Gln His Gln
                100                 105                 110

His Gly His Gln His Glu Gln Gln Arg Gly His Gln His Gln His Gln
            115                 120                 125

His Gln His Glu His Glu Gln Pro Glu Ser Gly His Arg Gln Gln Gln
130                 135                 140

Ser Ser Gly Arg Gly His Gln Gly Ala His Gln Glu Gln Gly Arg Asp
145                 150                 155                 160

Ser Ala Arg Ser Arg Gly Ser Asn Gln Gly His Ser Ser Arg His
                165                 170                 175

Gln Ala Asp Ser Pro Arg Val Ser Ala Arg Ser Gly Ser Gly Arg
                180                 185                 190

Gly Gln Ser Pro Asp Ala Ser Gly Arg Ser Ser Asn Arg Arg Asp Arg
            195                 200                 205

Pro Arg Gln Pro Ser Pro Ser Gln Ser Ser Asp Ser Gln Val His Ser
210                 215                 220

Gly Val Gln Val Glu Gly Arg Arg Gly Gln Ser Ser Ser Ala Asn Arg
```

```
                225                 230                 235                 240
Arg Ala Gly Ser Ser Gly Ser Gly Val Gln Gly Ala Ser Ala
                245                 250                 255

<210> SEQ ID NO 11
<211> LENGTH: 3541
<212> TYPE: PRT
<213> ORGANISM: Mus musculus

<400> SEQUENCE: 11

Met Ser Ile Leu Glu Pro Arg Thr Lys Ala Arg Pro Arg Asp Ala Leu
1               5                   10                  15

Ile Cys Gly Leu Ala Ala Asp Ala Ser Arg Arg Ser Gly Ala Arg Gln
            20                  25                  30

Gly Gln Ala Ser Ala Gln Gly Arg Ala Gly Ser Gln Gly Gln Ala Gln
        35                  40                  45

Gly Arg Val Gly Ser Ser Ala Asp Arg Gln Gly Arg Arg Gly Val Ser
    50                  55                  60

Glu Ser Gln Ala Ser Asp Ser Glu Gly His Ser Asp Phe Ser Glu Gly
65                  70                  75                  80

Gln Ala Val Gly Ala His Arg Gln Ser Gly Ala Gly Gln Arg His Glu
                85                  90                  95

Gln Arg Ser Ser Arg Gly Gln His Gly Ser Arg Tyr Tyr Tyr Glu Gln
            100                 105                 110

Glu His Ser Glu Glu Glu Ser Asp Ser Gln His Gln His Gly His Gln
        115                 120                 125

His Glu Gln Gln Arg Gly His Gln His Gln His Gln His Glu Gln Pro
130                 135                 140

Glu Ser Gly His Arg Gln Gln Ser Ser Gly Arg Gly His Gln Gly
145                 150                 155                 160

Ala His Gln Glu Gln Gly Arg Asp Ser Ala Arg Ser Arg Gly Ser Asn
                165                 170                 175

Gln Gly His Ser Ser Ser Arg His Gln Ala Asp Ser Pro Arg Val Ser
            180                 185                 190

Ala Arg Ser Gly Ser Gly Gly Arg Gly Gln Ser Pro Asp Ala Ser Gly
        195                 200                 205

Arg Ser Ser Asn Arg Arg Asp Arg Pro Arg Gln Pro Ser Pro Ser Gln
    210                 215                 220

Ser Ser Asp Ser Gln Val His Ser Gly Val Gln Val Glu Gly Arg Arg
225                 230                 235                 240

Gly Gln Ser Ser Ser Ala Asn Arg Arg Ala Gly Ser Ser Ser Gly Ser
                245                 250                 255

Gly Val Gln Gly Ala Ser Ala Gly Gly Leu Ala Ala Asp Ala Ser Arg
            260                 265                 270

Arg Ser Gly Ala Arg Gln Gly Gln Ala Ser Ala Gln Gly Arg Ala Gly
        275                 280                 285

Ser Gln Gly Gln Ala Gln Gly Arg Ile Gly Ser Ser Ala Asp Arg Gln
    290                 295                 300

Gly Arg Arg Gly Val Ser Glu Ser Gln Ala Ser Asp Ser Glu Gly His
305                 310                 315                 320

Ser Asp Phe Ser Glu Gly Gln Ala Val Gly Ala His Arg Gln Ser Glu
                325                 330                 335

Ala Gly Gln Arg His Glu Gln Arg Ser Ser Arg Gly Gln His Gly Ser
            340                 345                 350
```

```
Gly Tyr Tyr Tyr Glu Gln Glu His Ser Glu Glu Ser Asp Ser Gln
            355                 360                 365
His Gln His Gly His Gln His Glu Gln Gln Arg Gly Thr Gln His Gln
    370                 375                 380
His Glu His Gln Gln Pro Glu Ser Gly His Arg Gln Gln Gln Ser Ser
385                 390                 395                 400
Gly Arg Gly His Gln Gly Thr His Gln Glu Gln Gly Arg Asp Ser Ala
                405                 410                 415
Arg Ser Arg Gly Ser Asn Gln Gly His Ser Ser Ser Arg His Gln Ala
            420                 425                 430
Asp Ser Pro Arg Val Ser Ala Arg Ser Gly Ser Gly Gly Arg Gly Gln
        435                 440                 445
Ser Pro Asp Ala Ser Gly Arg Ser Ser Asn Arg Arg Asp Arg Pro Arg
    450                 455                 460
Gln Pro Ser Pro Ser Gln Ser Ser Asp Ser Gln Val His Ser Gly Val
465                 470                 475                 480
Gln Val Glu Gly Arg Arg Gln Ser Ser Ser Ala Asn Arg Arg Ala
                485                 490                 495
Gly Ser Ser Ser Gly Ser Gly Val Gln Gly Ala Ser Ala Gly Gly Leu
            500                 505                 510
Ala Ala Asp Ala Ser Arg Arg Ser Gly Ala Arg Gln Gly Gln Ala Ser
        515                 520                 525
Ala Gln Gly Arg Ala Gly Ser Gln Gly Gln Ala Gln Gly Arg Val Gly
    530                 535                 540
Ser Ser Ala Asp Arg Gln Gly Arg Arg Gly Val Ser Glu Ser Gln Ala
545                 550                 555                 560
Ser Asp Ser Glu Gly His Ser Asp Phe Ser Glu Gly Gln Ala Val Gly
                565                 570                 575
Ala His Arg Gln Ser Gly Ala Gly Gln Arg His Glu Gln Arg Ser Ser
            580                 585                 590
Arg Gly Gln His Gly Ser Gly Phe Tyr Pro Val Tyr Tyr Tyr Tyr Glu
        595                 600                 605
Gln Glu His Ser Glu Glu Glu Ser Asp Ser Gln His Gln His Gly His
    610                 615                 620
Gln His Glu Gln Gln Arg Gly His Gln His Gln His Gln His Glu His
625                 630                 635                 640
Glu Gln Pro Glu Ser Gly His Arg Gln Gln Gln Ser Ser Gly Arg Gly
                645                 650                 655
His Gln Gly Ala His Gln Glu Gln Gly Arg Asp Ser Ala Arg Ser Arg
            660                 665                 670
Gly Ser Asn Gln Gly His Ser Ser Arg His Gln Ala Asp Ser Pro
        675                 680                 685
Arg Val Ser Ala Arg Ser Gly Ser Gly Arg Gly Gln Ser Pro Asp
    690                 695                 700
Ala Ser Gly Arg Ser Ser Asn Arg Arg Asp Arg Pro Arg Gln Pro Ser
705                 710                 715                 720
Pro Ser Gln Ser Ser Asp Ser Gln Val His Ser Gly Val Gln Val Glu
                725                 730                 735
Gly Arg Arg Gly Gln Ser Ser Ser Ala Asn Arg Arg Ala Gly Ser Ser
            740                 745                 750
Ser Gly Ser Gly Val Gln Gly Ala Ser Ala Gly Gly Leu Ala Ala Asp
        755                 760                 765
Ala Ser Arg Arg Ser Gly Ala Leu Gln Gly Gln Ala Ser Ala Gln Gly
```

```
                770              775              780
Arg Ala Gly Ser Gln Gly Gln Ala Gln Gly Arg Val Gly Ser Ser Ala
785              790              795              800

Asp Arg Gln Gly Arg Arg Gly Val Ser Gly Ser Gln Ala Ser Asp Ser
                805              810              815

Glu Gly His Ser Asp Phe Ser Glu Gly Gln Ala Val Gly Ala His Arg
                820              825              830

Gln Ser Gly Ala Gly Gln Arg His Glu Gln Arg Ser Ser Arg Gly Gln
                835              840              845

His Gly Ser Gly Tyr Tyr Tyr Glu Gln Glu His Ser Glu Glu Glu Ser
850              855              860

Asp Ser Gln His Gln His Gly Pro Pro Ala Arg Thr Ala Thr Gln Gln
865              870              875              880

Gln Phe Ser Gly Arg Gly His Gln Gly Ala His Gln Glu Gln Gly Arg
                885              890              895

Asp Ser Ala Arg Ser Arg Gly Ser Asn Gln Gly His Ser Ser Ser Arg
                900              905              910

His Gln Ala Asp Ser Pro Arg Val Ser Ala Arg Ser Gly Ser Gly Gly
                915              920              925

Arg Gly Gln Ser Pro Asp Ala Ser Gly Arg Ser Ser Asn Arg Arg Asp
930              935              940

Arg Pro Arg Gln Pro Ser Pro Ser Gln Ser Ser Asp Ser Gln Val His
945              950              955              960

Ser Gly Val Gln Val Glu Gly Arg Arg Gly Gln Ser Ser Ser Ala Asn
                965              970              975

Arg Arg Ala Gly Ser Ser Ser Gly Ser Gly Val Gln Gly Ala Ser Ala
                980              985              990

Gly Gly Leu Ala Ala Asp Ala Ser Arg Arg Ser Gly Ala Arg Gln Gly
                995              1000             1005

Gln Ala Ser Ala Gln Gly Arg Ala Gly Ser Gln Gly Gln Ala Gln
    1010             1015             1020

Gly Arg Val Gly Ser Ser Ala Asp Arg Gln Gly Arg Arg Gly Val
    1025             1030             1035

Ser Glu Ser Gln Ala Ser Asp Ser Glu Gly His Ser Asp Phe Ser
    1040             1045             1050

Glu Gly Gln Ala Val Gly Ala His Arg Gln Ser Gly Ala Gly Gln
    1055             1060             1065

Arg His Glu Gln Arg Ser Ser Arg Gly Gln His Gly Ser Gly Phe
    1070             1075             1080

Tyr Pro Val Tyr Tyr Tyr Glu Gln Glu His Ser Glu Glu Glu
    1085             1090             1095

Ser Asp Ser Gln His Gln His Gly His Gln His Glu Gln Gln Arg
    1100             1105             1110

Gly His Gln His Gln His Gln His Gln His Glu His Glu Gln Pro
    1115             1120             1125

Glu Ser Gly His Arg Gln Gln Gln Ser Ser Gly Arg Gly His Gln
    1130             1135             1140

Gly Ala His Gln Glu Gln Gly Arg Asp Ser Ala Arg Ser Arg Gly
    1145             1150             1155

Ser Asn Gln Gly His Ser Ser Arg His Gln Ala Asp Ser Pro
    1160             1165             1170

Arg Val Ser Ala Arg Ser Gly Ser Gly Gly Arg Gly Gln Ser Pro
    1175             1180             1185
```

```
Asp Ala Ser Gly Arg Ser Ser Asn Arg Arg Asp Arg Pro Arg Gln
    1190                1195                1200

Pro Ser Pro Ser Gln Ser Ser Asp Ser Gln Val His Ser Gly Val
    1205                1210                1215

Gln Val Glu Gly Arg Arg Gly Gln Ser Ser Ala Asn Arg Arg
    1220                1225                1230

Ala Gly Ser Ser Ser Gly Ser Gly Val Gln Gly Ala Ser Ala Gly
    1235                1240                1245

Gly Leu Ala Ala Asp Ala Ser Arg Arg Ser Gly Ala Arg Gln Gly
    1250                1255                1260

Gln Ala Ser Ala Gln Gly Arg Ala Gly Ser Gln Gly Gln Ala Gln
    1265                1270                1275

Gly Arg Val Gly Ser Ser Ala Asp Arg Gln Gly Arg Arg Gly Val
    1280                1285                1290

Ser Glu Ser Gln Ala Ser Asp Ser Glu Gly His Ser Asp Phe Ser
    1295                1300                1305

Glu Gly Gln Ala Val Gly Ala His Arg Gln Ser Gly Ala Gly Gln
    1310                1315                1320

Arg His Glu Gln Arg Ser Ser Arg Gly Gln His Gly Ser Gly Tyr
    1325                1330                1335

Tyr Tyr Glu Gln Glu His Ser Glu Glu Glu Ser Asp Ser Gln His
    1340                1345                1350

Gln His Ser His Gln His Glu Gln Gln Arg Gly His Gln His Gln
    1355                1360                1365

His Gln His Gln His Glu His Glu Gln Pro Glu Ser Gly His Arg
    1370                1375                1380

Gln Gln Gln Phe Ser Gly Arg Gly His Gln Gly Ala His Gln Glu
    1385                1390                1395

Gln Gly Arg Asp Ser Ala Arg Ser Arg Gly Ser Asn Gln Gly His
    1400                1405                1410

Ser Ser Ser Arg His Gln Ala Asp Ser Pro Arg Val Ser Ala Arg
    1415                1420                1425

Ser Gly Ser Gly Gly Arg Gly Gln Ser Pro Asp Ala Ser Gly Arg
    1430                1435                1440

Ser Ser Asn Arg Arg Asp Arg Pro Arg Gln Pro Ser Pro Ser Gln
    1445                1450                1455

Ser Ser Asp Ser Gln Val His Ser Gly Val Gln Val Glu Gly Arg
    1460                1465                1470

Arg Gly Gln Ser Ser Ser Ala Asn Arg Arg Ala Gly Ser Ser Ser
    1475                1480                1485

Gly Ser Gly Val Gln Gly Ala Ser Ala Gly Gly Leu Ala Ala Asp
    1490                1495                1500

Ala Ser Arg Arg Ser Gly Ala Arg Gln Gly Gln Ala Ser Ala Gln
    1505                1510                1515

Gly Arg Ala Gly Ser Gln Gly Gln Ala Gln Gly Arg Val Gly Ser
    1520                1525                1530

Ser Ala Asp Arg Gln Gly Arg Arg Gly Val Ser Glu Ser Gln Ala
    1535                1540                1545

Ser Asp Ser Glu Gly His Ser Asp Phe Ser Glu Gly Gln Ala Val
    1550                1555                1560

Gly Ala His Arg Gln Ser Gly Ala Gly Gln Arg His Glu Gln Arg
    1565                1570                1575
```

-continued

```
Ser Ser Arg Gly Gln His Gly Ser Gly Phe Tyr Pro Val Tyr Tyr
    1580            1585            1590

Tyr Tyr Glu Gln Glu His Ser Glu Glu Glu Ser Asp Ser Gln His
    1595            1600            1605

Gln His Gly His Gln His Glu Gln Gln Arg Gly His Gln His Gln
    1610            1615            1620

His Gln His Gln His Glu His Glu Gln Pro Glu Ser Gly His Arg
    1625            1630            1635

Gln Gln Gln Ser Ser Gly Arg Gly His Gln Gly Ala His Gln Glu
    1640            1645            1650

Gln Gly Arg Asp Ser Ala Arg Ser Arg Gly Ser Asn Gln Gly His
    1655            1660            1665

Ser Ser Ser Arg His Gln Ala Asp Ser Pro Arg Val Ser Ala Arg
    1670            1675            1680

Ser Gly Ser Gly Gly Arg Gly Gln Ser Pro Asp Ala Ser Gly Arg
    1685            1690            1695

Ser Ser Asn Arg Arg Asp Arg Pro Arg Gln Pro Ser Pro Ser Gln
    1700            1705            1710

Ser Ser Asp Ser Gln Val His Ser Gly Val Gln Val Glu Gly Arg
    1715            1720            1725

Arg Gly Gln Ser Ser Ser Ala Asn Arg Arg Ala Gly Ser Ser Ser
    1730            1735            1740

Gly Ser Gly Val Gln Gly Ala Ser Ala Gly Gly Leu Ala Ala Asp
    1745            1750            1755

Ala Ser Arg Arg Ser Gly Ala Arg Gln Gly Gln Ala Ser Ala Gln
    1760            1765            1770

Gly Arg Ala Gly Ser Gln Gly Gln Ala Gln Gly Arg Val Gly Ser
    1775            1780            1785

Ser Ala Asp Arg Gln Gly Arg Arg Gly Val Ser Glu Ser Gln Ala
    1790            1795            1800

Ser Asp Ser Glu Gly His Ser Asp Phe Ser Glu Gly Gln Ala Val
    1805            1810            1815

Gly Ala His Arg Gln Ser Gly Ala Gly Gln Arg His Glu Gln Arg
    1820            1825            1830

Ser Ser Arg Ser Gln His Gly Ser Gly Tyr Tyr Tyr Glu Gln Glu
    1835            1840            1845

His Ser Glu Glu Glu Ser Asp Ser Gln His Gln His Ser His Gln
    1850            1855            1860

His Glu Gln Gln Arg Gly His Gln His Gln His Gln His Gln His
    1865            1870            1875

Glu His Glu Gln Pro Glu Ser Gly His Arg Gln Gln Ser Ser
    1880            1885            1890

Gly Arg Gly Asn Gln Gly Ala His Gln Glu Gln Gly Arg Asp Ser
    1895            1900            1905

Ala Arg Ser Arg Gly Ser Asn Gln Gly His Ser Ser Ser Arg His
    1910            1915            1920

Gln Ala Asp Ser Pro Arg Val Ser Ala Arg Ser Gly Ser Gly Gly
    1925            1930            1935

Arg Gly Gln Ser Pro Asp Ala Ser Gly Arg Ser Ser Asn Arg Arg
    1940            1945            1950

Asp Arg Pro Arg Gln Pro Ser Pro Ser Gln Ser Ser Asp Ser His
    1955            1960            1965

Val His Ser Gly Val Gln Val Glu Gly Arg Arg Gly Gln Ser Ser
```

-continued

```
            1970                1975                1980
Ser Ala Asn Arg Arg Ala Gly Ser Ser Ser Gly Ser Gly Val Gln
        1985                1990                1995
Gly Ala Ser Ala Gly Gly Leu Ala Ala Asp Ala Ser Arg Arg Ser
        2000                2005                2010
Gly Ala Arg Gln Gly Gln Ala Ser Ala Gln Gly Arg Ala Gly Ser
        2015                2020                2025
Gln Gly Gln Ala Gln Gly Arg Val Gly Ser Ser Ala Asp Arg Gln
        2030                2035                2040
Gly Arg Arg Gly Val Ser Glu Ser Gln Ala Ser Asp Ser Glu Gly
        2045                2050                2055
His Ser Asp Phe Ser Glu Gly Gln Ala Val Gly Ala His Arg Gln
        2060                2065                2070
Ser Gly Ala Gly Gln Arg His Glu Gln Arg Ser Ser Arg Gly Gln
        2075                2080                2085
His Gly Ser Gly Phe Tyr Pro Val Tyr Tyr Tyr Glu Gln Glu
        2090                2095                2100
His Ser Glu Glu Glu Ser Asp Ser Gln His Gln His Gly His Gln
        2105                2110                2115
His Glu Gln Gln Arg Gly His Gln His Gln His Gln His Gln His
        2120                2125                2130
Glu His Glu Gln Pro Glu Ser Gly His Arg Gln Gln Ser Ser
        2135                2140                2145
Gly Arg Gly His Gln Gly Ala His Gln Glu Gln Gly Arg Asp Ser
        2150                2155                2160
Ala Arg Ser Arg Gly Ser Asn Gln Gly His Ser Ser Ser Arg His
        2165                2170                2175
Gln Ala Asp Ser Pro Arg Val Ser Ala Arg Ser Gly Ser Gly Gly
        2180                2185                2190
Arg Gly Gln Ser Pro Asp Ala Ser Gly Arg Ser Asn Arg Arg
        2195                2200                2205
Asp Arg Ser Arg Gln Pro Ser Pro Ser Gln Ser Ser Asp Ser Gln
        2210                2215                2220
Val His Ser Gly Val Gln Val Glu Gly Arg Arg Gly Gln Ser Ser
        2225                2230                2235
Ser Ala Asn Arg Arg Ala Gly Ser Ser Ser Gly Ser Gly Val Gln
        2240                2245                2250
Gly Ala Ser Ala Gly Gly Leu Ala Ala Asp Ala Ser Arg Arg Ser
        2255                2260                2265
Gly Ala Arg Gln Gly Gln Ala Ser Ala Gln Gly Arg Ala Gly Ser
        2270                2275                2280
Gln Gly Gln Ala Gln Gly Arg Val Gly Ser Ser Ala Asp Arg Gln
        2285                2290                2295
Gly Arg Arg Gly Val Ser Glu Ser Gln Ala Ser Asp Ser Glu Gly
        2300                2305                2310
His Ser Asp Phe Ser Glu Gly Gln Ala Val Gly Ala His Arg Gln
        2315                2320                2325
Ser Gly Ala Gly Gln Arg His Glu Gln Arg Ser Ser Arg Gly Gln
        2330                2335                2340
His Gly Ser Gly Phe Tyr Pro Val Tyr Tyr Tyr Glu Gln Glu
        2345                2350                2355
His Ser Glu Glu Glu Ser Asp Ser Gln His Gln His Gly His Gln
        2360                2365                2370
```

```
His Glu Gln Gln Arg Gly His Gln His Gln His Glu His
    2375                2380                2385

Glu Gln Pro Glu Ser Gly His Arg Gln Gln Ser Ser Gly Arg
    2390                2395                2400

Gly His Gln Gly Ala His Gln Glu Gln Gly Arg Asp Ser Ala Arg
    2405                2410                2415

Ser Arg Gly Ser Asn Gln Gly His Ser Ser Arg His Gln Ala
    2420                2425                2430

Asp Ser Pro Arg Val Ser Ala Arg Ser Gly Ser Gly Gly Arg Gly
    2435                2440                2445

Gln Ser Pro Asp Ala Ser Gly Arg Ser Ser Asn Arg Arg Asp Arg
    2450                2455                2460

Pro Arg Gln Pro Ser Pro Ser Gln Ser Ser Asp Ser Gln Val His
    2465                2470                2475

Ser Gly Val Gln Val Glu Gly Arg Arg Gly Gln Ser Ser Ser Ala
    2480                2485                2490

Asn Arg Arg Ala Gly Ser Ser Ser Gly Ser Gly Val Gln Gly Ala
    2495                2500                2505

Ser Ala Gly Gly Leu Ala Ala Asp Ala Ser Arg Arg Ser Gly Ala
    2510                2515                2520

Leu Gln Gly Gln Ala Ser Ala Gln Gly Arg Ala Gly Ser Gln Gly
    2525                2530                2535

Gln Ala Gln Gly Arg Val Gly Ser Ser Ala Asp Arg Gln Gly Arg
    2540                2545                2550

Arg Gly Val Ser Glu Ser Gln Ala Ser Asp Ser Glu Gly His Ser
    2555                2560                2565

Asp Phe Ser Glu Gly Gln Ala Val Gly Ala His Arg Gln Ser Gly
    2570                2575                2580

Ala Gly Gln Arg His Glu Gln Arg Ser Ser Arg Gly Gln His Gly
    2585                2590                2595

Ser Gly Tyr Tyr Tyr Glu Gln Glu His Ser Glu Glu Glu Ser Asp
    2600                2605                2610

Ser Gln His Gln His Gly His Gln His Glu Gln Gln Arg Gly His
    2615                2620                2625

Gln His Gln His Gln His Gln His Glu His Glu Gln Pro Glu Ser
    2630                2635                2640

Gly His Arg Gln Gln Ser Ser Gly Arg Gly His Gln Gly Ala
    2645                2650                2655

His Gln Glu Gln Gly Arg Asp Ser Ala Arg Ser Arg Gly Ser Asn
    2660                2665                2670

Gln Gly His Ser Ser Arg His Gln Ala Asp Ser Pro Arg Val
    2675                2680                2685

Ser Ala Arg Ser Gly Ser Gly Arg Gly Gln Ser Pro Asp Ala
    2690                2695                2700

Ser Gly Arg Ser Ser Asn Arg Arg Asp Arg Pro Arg Gln Pro Ser
    2705                2710                2715

Pro Ser Gln Ser Ser Asp Ser Gln Val His Ser Gly Val Gln Val
    2720                2725                2730

Glu Gly Arg Arg Gly Gln Ser Ser Ser Ala Asn Arg Arg Ala Gly
    2735                2740                2745

Ser Ser Ser Gly Ser Gly Val Gln Gly Ala Ser Ala Gly Gly Leu
    2750                2755                2760
```

```
Ala Ala Asp Ala Ser Arg Arg Ser Gly Ala Arg Gln Gly Gln Ala
    2765                2770                2775
Ser Ala Gln Gly Arg Ala Gly Ser Gln Gly Gln Ala Gln Gly Arg
    2780                2785                2790
Val Gly Ser Ser Ala Asp Arg Gln Gly Arg Arg Gly Val Ser Gly
    2795                2800                2805
Ser Gln Ala Ser Asp Ser Glu Gly His Ser Asp Phe Ser Glu Gly
    2810                2815                2820
Gln Ala Val Gly Ala His Arg Gln Ser Gly Ala Gly Gln Arg His
    2825                2830                2835
Glu Gln Arg Ser Ser Arg Gly Gln His Gly Ser Gly Tyr Tyr Tyr
    2840                2845                2850
Glu Gln Glu His Ser Glu Glu Glu Ser Asp Ser Gln His Gln His
    2855                2860                2865
Gly His Gln His Glu Gln Gln Arg Gly His Gln His Gln His Gln
    2870                2875                2880
His Gln His Glu His Glu Gln Pro Glu Ser Gly His Arg Gln Gln
    2885                2890                2895
Gln Phe Ser Gly Arg Gly His Gln Gly Ala His Gln Glu Gln Gly
    2900                2905                2910
Arg Asp Ser Ala Arg Ser Arg Gly Ser Asn Gln Gly His Ser Ser
    2915                2920                2925
Ser Arg His Gln Ala Asp Ser Pro Arg Val Ser Ala Arg Ser Gly
    2930                2935                2940
Ser Gly Gly Arg Gly Gln Ser Pro Asp Ala Ser Gly Arg Ser Ser
    2945                2950                2955
Asn Arg Arg Asp Arg Pro Arg Gln Pro Ser Pro Ser Gln Ser Ser
    2960                2965                2970
Asp Ser Gln Val His Ser Gly Val Gln Val Glu Gly Arg Arg Gly
    2975                2980                2985
Gln Ser Ser Ser Ala Asn Arg Arg Ala Gly Ser Ser Ser Ser Ser
    2990                2995                3000
Gly Val Gln Gly Ala Ser Ala Gly Gly Leu Ala Ala Asp Ala Ser
    3005                3010                3015
Arg Arg Ser Gly Ala Arg Gln Gly Gln Ala Ser Ala Gln Gly Arg
    3020                3025                3030
Ala Gly Ser Gln Gly Gln Ala Gln Gly Arg Val Gly Ser Ser Ala
    3035                3040                3045
Asp Arg Gln Gly Arg Arg Gly Val Ser Glu Ser Gln Ala Ser Asp
    3050                3055                3060
Ser Glu Gly His Ser Asp Phe Ser Glu Gly Gln Ala Val Gly Ala
    3065                3070                3075
His Arg Gln Ser Gly Ala Gly Gln Arg His Glu Gln Arg Ser Ser
    3080                3085                3090
Arg Gly Gln His Gly Ser Gly Phe Tyr Pro Val Tyr Tyr Tyr Tyr
    3095                3100                3105
Glu Gln Glu His Ser Glu Glu Glu Ser Asp Ser Gln His Gln His
    3110                3115                3120
Gly His Gln His Glu Gln Gln Arg Gly His Gln His Gln His Gln
    3125                3130                3135
His Gln His Glu His Glu Gln Pro Glu Ser Gly His Arg Gln Gln
    3140                3145                3150
Gln Phe Ser Gly Arg Gly His Gln Gly Ala His Gln Glu Gln Gly
```

```
                3155                3160                3165
Arg Asp Ser Ala Arg Ser Arg Gly Ser Asn Gln Gly His Ser Ser
        3170                3175                3180

Ser Arg His Gln Ala Asp Ser Pro Arg Val Ser Ala Arg Ser Gly
        3185                3190                3195

Ser Gly Gly Arg Gly Gln Ser Pro Asp Ala Ser Gly Arg Ser Ser
        3200                3205                3210

Asn Arg Arg Asp Arg Pro Gln Pro Ser Pro Ser Gln Ser Ser
        3215                3220                3225

Asp Ser Gln Val His Ser Gly Val Gln Val Glu Gly Arg Arg Gly
        3230                3235                3240

Gln Ser Ser Ser Ala Asn Arg Arg Ala Gly Ser Ser Ser Gly Ser
        3245                3250                3255

Gly Val Gln Gly Ala Ser Ala Gly Gly Leu Ala Ala Asp Ala Ser
        3260                3265                3270

Arg Arg Ser Gly Ala Arg Gln Gly Gln Ala Ser Ala Gln Gly Arg
        3275                3280                3285

Ala Gly Ser Gln Gly Gln Ala Gln Gly Arg Val Gly Ser Ser Ala
        3290                3295                3300

Asp Arg Gln Gly Arg Arg Gly Val Ser Glu Ser Gln Ala Ser Asp
        3305                3310                3315

Ser Glu Gly His Ser Asp Phe Ser Glu Gly Gln Ala Val Gly Ala
        3320                3325                3330

His Arg Gln Ser Gly Ala Gly Gln Arg His Glu Gln Arg Ser Ser
        3335                3340                3345

Arg Gly Gln His Gly Ser Gly Tyr Tyr Tyr Glu Gln Glu His Ser
        3350                3355                3360

Glu Glu Glu Ser Asp Ser Gln His Gln Gln Gly His Gln His Glu
        3365                3370                3375

Gln Gln Arg Gly His Gln His Gln His Gln His Gln His Glu His
        3380                3385                3390

Glu Gln Pro Glu Ser Gly His Arg Gln Gln Gln Ser Ser Gly Arg
        3395                3400                3405

Gly His Gln Gly Ala His Gln Glu Gln Gly Arg Asp Ser Ala Arg
        3410                3415                3420

Ser Arg Gly Ser Asn Gln Gly His Ser Ser Ser Arg His Gln Ala
        3425                3430                3435

Asp Ser Pro Arg Val Ser Ala Arg Ser Gly Ser Gly Gly Arg Gly
        3440                3445                3450

Gln Ser Pro Asp Gly Ser Gly Arg Ser Ser Asn Arg Arg Asp Arg
        3455                3460                3465

Pro Arg Gln Pro Ser Ala Ser Gln Ser Ser Asp Ser Gln Val His
        3470                3475                3480

Ser Gly Val Gln Val Glu Ala Gln Arg Gly Gln Ser Ser Ser Ala
        3485                3490                3495

Asn Arg Arg Ala Gly Ser Ser Gly Ser Gly Val Gln Ser Ala
        3500                3505                3510

Ala Ala Ser Gly Gln Gly Gly Tyr Glu Ser Ile Phe Thr Ala Lys
        3515                3520                3525

His Leu Asp Phe Asn Gln Ser His Ser Tyr Tyr Tyr Tyr
        3530                3535                3540

<210> SEQ ID NO 12
```

```
<211> LENGTH: 336
<212> TYPE: PRT
<213> ORGANISM: Mus musculus

<400> SEQUENCE: 12

Pro Asp Gly Ser Gly Arg Ser Ser Asn Arg Arg Asp Arg Pro Arg Gln
1               5                   10                  15

Leu Ser Pro Ser Gln Ser Ser Asp Ser Gln Val His Ser Gly Val Gln
            20                  25                  30

Val Glu Gly Arg Arg Gly His Ser Ser Ala Asn Arg Arg Ala Gly
        35                  40                  45

Ser Ser Ser Gly Ser Gly Val Gln Gly Ala Ser Ala Gly Gly Leu Ala
    50                  55                  60

Ala Asp Ala Ser Arg Arg Ser Gly Ala Arg Gln Gly Gln Ala Ser Ala
65                  70                  75                  80

Gln Gly Arg Ala Gly Ser Gln Gly Gln Ala Gln Gly Arg Val Ser Ser
                85                  90                  95

Ser Ala Asp Arg Gln Gly Arg Arg Gly Val Ser Glu Ser Arg Ala Ser
                100                 105                 110

Asp Ser Glu Gly His Ser Asp Phe Ser Glu Gly Gln Ala Val Gly Ala
            115                 120                 125

His Arg Gln Ser Gly Ala Gly Gln Arg His Glu Gln Arg Ser Ser Arg
        130                 135                 140

Gly Gln His Gly Ser Gly Tyr Tyr Tyr Glu Gln Glu His Ser Glu Glu
145                 150                 155                 160

Glu Ser Asp Ser Gln His Gln His Gly His Gln His Glu Gln Gln Arg
                165                 170                 175

Gly His Gln His Gln His Gln His Gln His Glu His Glu Gln Pro Glu
            180                 185                 190

Ser Gly His Arg Gln Gln Gln Ser Ser Gly Arg Gly His Gln Gly Ala
        195                 200                 205

His Gln Glu Gln Gly Arg Asp Ser Ala Arg Pro Arg Gly Ser Asn Gln
    210                 215                 220

Gly His Ser Ser Arg His Gln Ala Asp Ser Pro Arg Val Ser Ala
225                 230                 235                 240

Arg Ser Gly Ser Gly Arg Gly Gln Ser Pro Asp Ala Ser Gly Arg
                245                 250                 255

Ser Ser Asn Arg Arg Asp Arg Pro Arg Gln Pro Ser Pro Ser Gln Ser
                260                 265                 270

Ser Asp Ser Gln Val His Ser Gly Val Gln Val Glu Ala Gln Arg Gly
            275                 280                 285

Gln Ser Ser Ser Ala Asn Arg Arg Ala Gly Ser Ser Ser Gly Ser Gly
        290                 295                 300

Val Gln Gly Ala Ala Ala Ser Gly Gln Gly Gly Tyr Glu Ser Ile Phe
305                 310                 315                 320

Thr Ala Lys His Leu Asp Phe Asn Gln Ser His Ser Tyr Tyr Tyr Tyr
                325                 330                 335

<210> SEQ ID NO 13
<211> LENGTH: 357
<212> TYPE: PRT
<213> ORGANISM: Mus musculus

<400> SEQUENCE: 13

Met Ser Ala Leu Leu Glu Ser Ile Thr Ser Met Ile Glu Ile Phe Gln
1               5                   10                  15
```

Gln Tyr Ser Thr Ser Asp Lys Glu Glu Thr Leu Ser Lys Glu Glu
            20                  25                  30

Leu Lys Glu Leu Leu Glu Gly Gln Leu Gln Ala Val Leu Lys Asn Pro
        35                  40                  45

Asp Asp Gln Asp Ile Ala Glu Val Phe Met Gln Met Leu Asp Val Asp
    50                  55                  60

His Asp Asp Lys Leu Asp Phe Ala Glu Tyr Leu Leu Leu Val Leu Lys
65                  70                  75                  80

Leu Ala Lys Ala Tyr Tyr Glu Ala Ser Lys Asn Glu Ser Phe Gln Thr
                85                  90                  95

His Gly Ser Asn Gly Arg Ser Lys Thr Asp Tyr Lys Gly Leu Glu Glu
            100                 105                 110

Glu Gly Glu Glu Gly Asn Lys Gln Asn Leu Arg Arg Arg His Gly Gly
        115                 120                 125

Thr Asp Gly Lys Arg Lys Ser Asp Arg Thr Arg Ser Pro Asn Gly Lys
    130                 135                 140

Arg Gly Lys Arg Gln Glu Ser Arg Cys Arg Ser Gly Lys Asp Lys
145                 150                 155                 160

His Arg Arg Glu Pro Glu Lys His Arg His Gln Gln Asp Ser Lys Arg
                165                 170                 175

Lys Gln Arg His Gly Ser Gly Ser Thr Glu Arg Lys Asp Asn Arg Asn
            180                 185                 190

Lys Lys Asn Arg Gln Ser Lys Glu Arg Asn Tyr Asp Glu Ile Tyr Asp
        195                 200                 205

Asn Gly Lys Tyr Asn Glu Asp Trp Glu Ala Ser Tyr Asn Asn Cys Tyr
    210                 215                 220

Tyr Lys Thr Gln Asn Thr Thr Leu Asp Gln Arg Glu Gly Asn Arg Arg
225                 230                 235                 240

Pro Arg Ala Asp Ser Gln Lys Glu Pro Gln Ser Ser His Gly Gln Ala
                245                 250                 255

Asp Asn Ser Asp Ser Glu Gly Gly Arg Gln Gln Ser His Ser Lys Pro
            260                 265                 270

Ser Pro Val Arg Ala Asp Gln Arg Arg Ser Arg Ala Gly Gln Ala Gly
        275                 280                 285

Ser Ser Lys Val Ser Ala Arg Ser Gly Ser Gly Gly Arg Gly Gln Ser
    290                 295                 300

Pro Asp Gly Ser Gly Arg Ser Ser Asn Arg Arg Asp Arg Pro Arg Gln
305                 310                 315                 320

Pro Ser Pro Ser Gln Ser Ser Asp Ser Gln Val His Ser Gly Val Gln
                325                 330                 335

Val Glu Gly Arg Arg Gly Gln Ser Ser Ser Ala Asn Arg Arg Ala Gly
            340                 345                 350

Ser Ser Ser Gly Ser
        355

<210> SEQ ID NO 14
<211> LENGTH: 366
<212> TYPE: PRT
<213> ORGANISM: Rattus norvegicus

<400> SEQUENCE: 14

Met Ser Thr Leu Leu Glu Ser Ile Thr Ser Met Ile Asp Ile Phe Gln
1               5                   10                  15

Gln Tyr Ser Asn Asn Asp Lys Glu Glu Glu Thr Leu Ser Lys Glu Glu

```
                20                  25                  30
Leu Lys Glu Leu Leu Glu Gly Glu Leu Gln Ala Val Leu Lys Asn Pro
            35                  40                  45
Asn Asp Gln Asp Ile Ala Glu Val Phe Met Gln Met Leu Asp Val Asp
        50                  55                  60
His Asp Asp Lys Ile Asp Phe Thr Glu Tyr Leu Leu Met Val Leu Lys
65                  70                  75                  80
Leu Ala Gln Ala Tyr Tyr Glu Thr Ser Lys Lys Arg Arg Ser Gln Thr
                85                  90                  95
Lys Glu Ser Gly Lys Arg Asn Glu His Asp Tyr Lys Gly Tyr Glu Glu
            100                 105                 110
Arg Arg Glu Lys Val Gln Arg His Arg Arg Asn Ser Gly Thr
        115                 120                 125
Asp Gly Lys Gln Glu Asn Glu Arg Ser Lys Ser Pro Arg Gly Arg Gly
        130                 135                 140
Asn Lys Arg Arg Gly Ser Ser Thr Ile Ser Glu Glu Ser Asp Thr Asn
145                 150                 155                 160
Arg Asn Ser Asp Thr Glu Asn Lys Arg His His Gly Ser Asn Arg
                165                 170                 175
Arg Gln Arg Arg Gly Ser Asn Ser Ser Asp Arg Lys Glu Thr Arg Ser
            180                 185                 190
Lys Lys His Arg Glu Val Lys Glu Arg Asn Ala Gly Ile Tyr Asn Asp
        195                 200                 205
Gly Lys Asp Gly Gln Asp Trp Glu Val Asn Tyr Glu Asn Cys Tyr Tyr
        210                 215                 220
Lys Thr Glu Glu Ser Asn Arg Glu Gln Arg Glu Gly Arg Asn His Lys
225                 230                 235                 240
Thr Lys Glu Ser His Ser Glu Ser Glu Ala Ser Gly Gly Gln Ala Gly
                245                 250                 255
Arg Arg Gly Thr Ala Ala Thr Arg His Thr Ser Arg Pro Glu Gln Ser
            260                 265                 270
Pro Asp Thr Ala Gly Arg Thr Gly Ser Ser Arg Gly Gln Gln Ser Ala
        275                 280                 285
Gln Arg His Ala Asp Ser Thr Pro Gly Ser Thr Arg Thr Gly Ser Arg
        290                 295                 300
Gly Arg Gly Glu Ser Pro Ala Gly Gln Gln Ser Pro Asp Arg Ala Arg
305                 310                 315                 320
His Ile Glu Ser Arg Arg Gly Arg Thr Arg Glu Ala Ser Ala Ser Gln
                325                 330                 335
Ser Ser Asp Ser Glu Gly His Ser Gly Ala His Ala Gly Ile Gly Gln
            340                 345                 350
Gly Gln Thr Ser Thr Thr His Arg Arg Ala Gly Ser Ser Ser
        355                 360                 365

<210> SEQ ID NO 15
<211> LENGTH: 3088
<212> TYPE: PRT
<213> ORGANISM: Pan troglodytes

<400> SEQUENCE: 15

Met Ser Thr Leu Leu Glu Asn Ile Phe Ala Ile Ile Asn Leu Phe Lys
1               5                   10                  15
Gln Tyr Ser Lys Lys Asp Lys Asn Thr Asp Thr Leu Ser Lys Lys Glu
            20                  25                  30
```

```
Leu Lys Glu Leu Leu Glu Lys Glu Phe Arg Gln Ile Leu Lys Asn Pro
             35                  40                  45

Asp Asp Pro Asp Met Val Asp Val Phe Met Asp His Leu Asp Ile Asp
 50                  55                  60

His Asn Lys Lys Ile Asp Phe Thr Glu Phe Leu Leu Met Val Phe Lys
 65                  70                  75                  80

Leu Ala Gln Ala Tyr Tyr Glu Ser Thr Arg Lys Glu Asn Leu Pro Ile
                 85                  90                  95

Ser Gly His Lys His Arg Lys His Ser His His Asp Lys His Glu Asp
            100                 105                 110

Asn Lys Gln Glu Glu Asn Lys Glu Asn Arg Lys Arg Pro Ser Ser Leu
            115                 120                 125

Glu Arg Arg Asn Asn Arg Lys Gly Asn Lys Gly Arg Ser Lys Ser Pro
130                 135                 140

Arg Glu Thr Gly Gly Lys Arg His Glu Ser Ser Ser Glu Lys Lys Glu
145                 150                 155                 160

Arg Lys Gly Tyr Ser Pro Thr His Arg Glu Glu Tyr Gly Lys Asn
                165                 170                 175

His His Asn Ser Ser Lys Lys Gln Lys Asn Lys Thr Glu Asn Thr Arg
            180                 185                 190

Leu Glu Asp Asn Arg Lys Arg Leu Ser Glu Arg Leu Glu Glu Lys Glu
            195                 200                 205

Asp Asn Glu Glu Gly Gly Tyr Asp Tyr Glu Asn Thr Gly Arg Met Thr
            210                 215                 220

Gln Lys Trp Ile Gln Ser Gly His Ile Ala Thr Tyr Tyr Thr Ile Gln
225                 230                 235                 240

Asp Glu Ala Tyr Asp Thr Thr Asp Asn Leu Leu Glu Glu Asn Lys Ile
                245                 250                 255

Tyr Glu Arg Ser Arg Ser Ser Asp Asp Lys Ser Ser Ser Gln Val Asn
            260                 265                 270

Arg Ser Arg His Glu Asn Thr Ser Gln Val Pro Leu Gln Glu Ser Arg
            275                 280                 285

Thr Arg Lys Arg Arg Gly Ser Arg Val Ser Gln Asp Arg Asp Ser Glu
290                 295                 300

Gly His Ser Glu Asp Ser Glu Arg His Ser Gly Ser Ala Ser Arg Asn
305                 310                 315                 320

His Pro Gly Ser Ala Arg Gln Gln Ser Arg Asp Gly Ser Arg His Pro
                325                 330                 335

Arg Ser His Asp Glu Asp Arg Ala Ser His Gly His Ser Ala Asp Ser
            340                 345                 350

Ser Arg Gln Ser Gly Thr Arg His Ala Glu Thr Ser Ser Arg Gly Gln
            355                 360                 365

Thr Ala Ser Ser His Glu Gln Ala Arg Ser Ser Pro Gly Glu Arg His
            370                 375                 380

Gly Ser Arg His Gln Gln Ser Ala Asp Ser Ser Arg His Ser Ala Thr
385                 390                 395                 400

Gly Arg Gly Gln Ala Ser Ser Ala Val Ser Asp Arg Gly Pro Arg Gly
                405                 410                 415

Ser Ser Gly Ser Gln Ala Ser Asp Glu Gly His Ser Glu Asn Ser
            420                 425                 430

Asp Thr Gln Ser Val Ser Gly His Gly Lys Ala Gly Pro Arg Gln Gln
            435                 440                 445

Ser His Gln Glu Ser Ala Arg Gly Arg Ser Gly Glu Arg Ser Gly His
```

```
            450                 455                 460
Ser Gly Ser Phe Leu Tyr Gln Val Ser Thr His Glu Gln Ser Asp Ser
465                 470                 475                 480

Ala His Gly Arg Thr Gly Thr Ser Thr Gly Gly Arg Gln Gly Ser His
                485                 490                 495

His Glu Gln Ala Arg Asp Ser Ser Arg His Ser Ala Ser Gln Glu Gly
            500                 505                 510

Gln Asp Thr Ile Arg Gly His Pro Gly Ser Ser Arg Gly Gly Arg Gln
            515                 520                 525

Gly Ser His His Glu Gln Leu Val Asn Arg Ser Gly His Ser Gly Ser
            530                 535                 540

His His Ser His Thr Thr Ser Gln Gly Arg Ser Asp Ala Ser His Gly
545                 550                 555                 560

Gln Ser Gly Ser Arg Ser Ala Ser Arg Gln Thr Arg Asn Glu Glu Gln
                565                 570                 575

Ser Gly Asp Gly Ser Arg His Ser Gly Ser Arg His His Glu Ala Ser
                580                 585                 590

Ser Gln Ala Asp Ser Ser Arg His Ser Gln Val Gly Gln Gly Gln Ser
            595                 600                 605

Ser Gly Pro Arg Thr Ser Ser His Gln Gly Ser Ser Val Ser Gln Asp
            610                 615                 620

Ser Asp Ser Glu Gly His Ser Glu Asp Ser Glu Arg Trp Ser Gly Ser
625                 630                 635                 640

Ala Ser Arg Asn His His Gly Ser Ala Arg Glu Gln Ser Arg Asp Gly
                645                 650                 655

Ser Arg His Pro Arg Ser His His Glu Asp Arg Ala Gly His Gly His
                660                 665                 670

Ser Ala Asp Ser Ser Arg Gln Ser Gly Thr Arg His Thr Glu Ser Ser
            675                 680                 685

Ser Arg Gly Gln Ala Val Ser Ser His Glu Gln Ala Arg Ser Ser Pro
            690                 695                 700

Gly Glu Arg His Gly Ser Arg His Gln Ser Ala Asp Ser Ser Arg
705                 710                 715                 720

His Ser Gly Ile Gly His Gly Gln Ala Ser Ser Ala Val Arg Asp Ser
                725                 730                 735

Gly His Arg Gly Ser Gly Ser Gln Ala Ile Asp Ser Glu Gly His
                740                 745                 750

Ser Glu Asp Ser Asp Thr Gln Ser Val Ser Ser His Gly Gln Ala Gly
            755                 760                 765

Pro His Gln Gln Ser His Lys Glu Ser Ala Arg Gly Gln Ser Gly Glu
            770                 775                 780

Ser Ser Gly Arg Ser Gly Ser Phe Leu Tyr Gln Val Ser Ser His Glu
785                 790                 795                 800

Gln Ser Glu Ser Thr Tyr Gly Gln Thr Ala Pro Ser Thr Gly Gly Arg
                805                 810                 815

Gln Gly Ser Arg His Glu Gln Ala Arg Asn Ser Ser Arg His Ser Ala
                820                 825                 830

Ser Gln Asp Gly Gln Asp Thr Ile Arg Gly His Pro Gly Ser Ser Arg
            835                 840                 845

Gly Gly Arg Gln Gly Ser Tyr His Glu Gln Ser Val Asp Arg Ser Gly
            850                 855                 860

His Ser Gly Tyr His His Ser His Thr Thr Pro Gln Gly Arg Ser Asp
865                 870                 875                 880
```

```
Ala Ser His Gly Gln Ser Gly Pro Arg Ser Ala Ser Arg Gln Thr Arg
            885                 890                 895

Asn Glu Glu Gln Ser Gly Asp Gly Ser Arg His Ser Gly Ser Arg His
            900                 905                 910

His Glu Pro Ser Thr Arg Ala Ser Ser Arg His Ser Gln Val Gly
            915                 920                 925

Gln Gly Glu Ser Ala Val Ser Lys Thr Ser Arg Gln Gly Ser Ser
            930                 935                 940

Val Ser Gln Asp Arg Asp Ser Glu Gly His Ser Glu Asp Ser Glu Arg
945                 950                 955                 960

Gln Ser Glu Ser Ala Ser Arg Asn His Tyr Gly Ser Ala Arg Glu Gln
            965                 970                 975

Ser Arg His Gly Ser Arg Asn Pro Arg Ser His Gln Glu Asp Arg Ala
            980                 985                 990

Ser His Gly His Ser Ala Glu Ser  Ser Arg Gln Ser Gly  Thr His His
            995                 1000                1005

Ala Glu  Thr Ser Ser His Gly  Gln Ala Ser  Gln Glu Gln
    1010                1015                1020

Ala Arg  Ser Ser Arg Gly Glu  Arg His Gly Ser Arg  His Gln Gln
    1025                1030                1035

Ser Ala  Asp Ser Ser Thr Asp  Ser Gly Thr Gly  Arg Gln Ala
    1040                1045                1050

Ser Ser  Val Val Gly Asp Ser  Gly Asn Arg Gly  Ser Gly Ser
    1055                1060                1065

Gln Ala  Ser Asp Ser Glu Gly  His Ser Glu Asp Ser  Asp Thr Gln
    1070                1075                1080

Ser Val  Ser Ala His Gly Gln  Ala Gly Pro Arg Gln  Gln Ser His
    1085                1090                1095

Gln Glu  Ser Thr Arg Gly Gln  Ser Gly Glu Arg Ser  Gly Arg Ser
    1100                1105                1110

Gly Ser  Phe Leu Tyr Gln Val  Ser Thr His Glu Gln  Ser Glu Ser
    1115                1120                1125

Ala His  Gly Arg Thr Gly Pro  Ser Thr Gly Gly Arg  Gln Arg Ser
    1130                1135                1140

Arg His  Glu Gln Ala Arg Asp  Ser Ser Arg His Ser  Ala Ser Gln
    1145                1150                1155

Glu Ser  Gln Asp Ile Ile His  Ala His Pro Gly Ser  Ser Arg Gly
    1160                1165                1170

Gly Arg  Gln Gly Ser His Tyr  Glu Gln Ser Val Asp  Arg Ser Gly
    1175                1180                1185

His Ser  Gly Ser His His Ser  His Thr Thr Ser Gln  Glu Arg Ser
    1190                1195                1200

Asn Ala  Ser His Gly Gln Ser  Gly Ser Arg Ser Ala  Ser Arg Gln
    1205                1210                1215

Thr Arg  Asn Glu Glu Gln Ser  Gly Asp Gly Ser Arg  His Ser Gly
    1220                1225                1230

Ser Arg  His His Glu Ala Ser  Ser Arg Ala Asp Ser  Ser Arg His
    1235                1240                1245

Ser Gln  Val Gly Gln Gly Gln  Ser Ser Gly Pro Arg  Thr Ser Arg
    1250                1255                1260

Asn Gln  Gly Ser Ser Val Ser  Gln Asp Ser Asp Ser  Gln Gly His
    1265                1270                1275
```

```
Ser Glu Asp Ser Glu Arg Trp Ser Gly Ser Ala Ser Arg Asn His
    1280            1285                1290

His Gly Ser Ala Trp Glu Gln Ser Arg Asp Gly Ser Arg His Pro
    1295            1300                1305

Gly Ser His Gln Glu Asp Arg Ala Gly His Gly His Ser Ala Asp
    1310            1315                1320

Ser Ser Arg Gln Ser Gly Thr His His Thr Glu Ser Ser Ser Arg
    1325            1330                1335

Gly Gln Ala Ala Ser Ser His Glu His Ala Arg Ser Ser Ala Gly
    1340            1345                1350

Glu Arg His Gly Ser His His Gln Gln Ser Ala Asp Ser Ser Arg
    1355            1360                1365

His Ser Gly Ile Gly His Gly Gln Ala Ser Ser Ala Val Arg Asp
    1370            1375                1380

Ser Gly His Arg Gly Ser Ser Gly Ser Gln Ala Ser Asp Ser Glu
    1385            1390                1395

Gly His Ser Glu Asp Ser Asp Thr Gln Ser Leu Ser Ala His Gly
    1400            1405                1410

Gln Ala Gly Pro His Gln Gln Ser His Gln Glu Ser Thr Arg Gly
    1415            1420                1425

Arg Ser Ala Glu Arg Ser Gly Arg Ser Gly Ser Phe Leu Tyr Gln
    1430            1435                1440

Val Ser Thr His Glu Gln Ser Glu Ser Ala His Gly Arg Thr Gly
    1445            1450                1455

Thr Ser Thr Gly Gly Arg Lys Arg Ser Leu His Glu Gln Ala Arg
    1460            1465                1470

Asp Ser Ser Arg His Ser Val Ser Gln Glu Gly Gln Asp Thr Ile
    1475            1480                1485

His Gly His Ala Gly Ser Ser Ser Gly Gly Arg Gln Gly Ser His
    1490            1495                1500

Tyr Glu Gln Leu Val Asp Arg Ser Gly His Ser Gly Ser His His
    1505            1510                1515

Ser His Thr Thr Ser Gln Gly Arg Ser Asp Ala Tyr His Gly Gln
    1520            1525                1530

Ser Gly Ser Arg Ser Ala Ser Arg Gln Thr His Asn Asp Glu Gln
    1535            1540                1545

Ser Gly Asp Gly Phe Arg His Ser Gly Ser His His His Glu Ala
    1550            1555                1560

Ser Ser Arg Ala Asp Ser Ser Arg His Ser Gln Val Gly Gln Gly
    1565            1570                1575

Gln Ser Glu Gly Pro Arg Thr Ser Arg His Arg Glu Ser Ser Val
    1580            1585                1590

Ser Gln Asp Ser Asp Ser Glu Gly His Ser Glu Asp Ser Glu Arg
    1595            1600                1605

Trp Ser Gly Ser Ala Ser Arg Asn His His Gly Ser Ala Arg Glu
    1610            1615                1620

Gln Ser Arg Asp Gly Ser Arg His Pro Arg Ser His His Glu Asp
    1625            1630                1635

Arg Ala Gly His Gly His Ser Ala Asp Ser Ser Arg Gln Ser Gly
    1640            1645                1650

Thr Arg His Thr Gln Thr Ser Ser Gly Gly Gln Ala Ala Ser Ser
    1655            1660                1665

His Glu Gln Gly Arg Ser Ser Ala Gly Glu Arg His Gly Ser Arg
```

```
            1670                1675                1680

His Gln Gln Ser Ala Asp Ser  Ser Arg His Ser Gly  Ile Gly His
    1685                1690                1695

Gly Gln Ala Ser Ser Ala Val  Arg Asp Ser Gly His  Arg Gly Tyr
    1700                1705                1710

Ser Gly Ser Gln Ala Ser Asp  Ser Glu Gly His Ser  Glu Asp Ser
    1715                1720                1725

Asp Thr Gln Ser Val Ser Ala  His Gly Gln Ala Gly  Ser His Gln
    1730                1735                1740

Gln Ser His Gln Glu Ser Ala  Arg Gly Arg Ser Gly  Glu Arg Ser
    1745                1750                1755

Gly Arg Ser Gly Ser Phe Leu  Tyr Gln Val Ser Thr  His Glu Gln
    1760                1765                1770

Ser Glu Ser Ser His Gly Trp  Thr Gly Pro Ser Thr  Arg Gly Arg
    1775                1780                1785

Gln Gly Ser Arg His Glu Gln  Ala Gln Asp Ser Ser  Arg His Ser
    1790                1795                1800

Ala Ser Gln Glu Gly Gln Asp  Thr Ile Arg Gly His  Pro Gly Pro
    1805                1810                1815

Ser Arg Gly Gly Arg Gln Gly  Tyr His His Glu Gln  Ser Val Asp
    1820                1825                1830

Ser Ser Gly His Ser Gly Ser  His His Ser His Ile  Thr Ser Gln
    1835                1840                1845

Gly Ser Ser His Ala Ser His  Gly Gln Ser Gly Ser  Arg Ser Ala
    1850                1855                1860

Ser Arg Thr Thr Arg Asn Asp  Glu Gln Ser Val Asp  Gly Ser Arg
    1865                1870                1875

His Ser Gly Ser Arg His His  Glu Ala Ser Thr His  Ala Asp Ile
    1880                1885                1890

Ser Arg His Ser Gln Ala Gly  Gln Gly Gln Ser Glu  Gly Ser Arg
    1895                1900                1905

Thr Ser Arg Arg Gln Gly Ser  Ser Val Ser Gln Asp  Ser Asp Ser
    1910                1915                1920

Glu Gly His Ser Glu Asp Ser  Glu Arg Trp Ser Gly  Ser Ala Ser
    1925                1930                1935

Arg Asn His Arg Gly Ser Ala  Gln Glu Gln Ser Arg  Asp Gly Ser
    1940                1945                1950

Arg His Pro Arg Ser His His  Glu Asp Arg Ala Gly  His Gly His
    1955                1960                1965

Ser Ala Asp Ser Ser Arg Gln  Ser Gly Thr His His  Ala Glu Thr
    1970                1975                1980

Ser Ser Gly Gly Gln Ala Ala  Ser Ser Arg Glu Gln  Ala Arg Ser
    1985                1990                1995

Ser Pro Gly Glu Arg His Gly  Ser Arg His Gln Gln  Ser Ala Asp
    2000                2005                2010

Ser Ser Arg His Ser Gly Ile  Arg Arg Gly Gln Ala  Ser Ser Ala
    2015                2020                2025

Val Arg Asp Ser Gly His Trp  Gly Ser Gly Ser Gln  Ala Ser
    2030                2035                2040

Asp Ser Glu Gly His Ser Glu  Glu Ser Asp Thr Gln  Ser Val Ser
    2045                2050                2055

Gly His Gly Gln Asp Gly Pro  His Gln Gln Ser His  Gln Glu Ser
    2060                2065                2070
```

```
Ala Arg Asp Arg Ser Gly Gly Arg Ser Gly Arg Ser Gly Ser Phe
2075             2080                2085

Leu Tyr Gln Val Ser Thr His Glu Gln Ser Glu Ser Thr His Gly
2090             2095                2100

Gln Thr Gly Thr Ser Thr Gly Gly Arg Gln Gly Ser His His Glu
2105             2110                2115

Gln Ala Arg Asp Ser Ser Arg His Ser Ala Ser Gln Glu Gly Gln
2120             2125                2130

Asp Thr Ile His Ala His Pro Gly Ser Ser Arg Gly Gly Arg Gln
2135             2140                2145

Gly Ser His His Glu Gln Ser Val Asp Thr Ser Gly His Ser Gly
2150             2155                2160

Ser His His Ser His Thr Thr Ser Gln Gly Arg Ser Asp Ala Ser
2165             2170                2175

His Gly Gln Ser Gly Ser Arg Ser Ala Ser Arg Gln Thr Arg Asn
2180             2185                2190

Asp Glu Gln Ser Gly Asp Gly Ser Arg His Ser Gly Ser His His
2195             2200                2205

His Glu Ala Phe Thr Gln Ala Asp Ser Ser Arg His Ser Gln Ser
2210             2215                2220

Gly Gln Gly Glu Ser Ala Gly Ser Arg Arg Ser Arg Arg Gln Gly
2225             2230                2235

Ser Ser Val Ser Gln Asp Ser Asp Ser Gln Gly His Ser Glu Asp
2240             2245                2250

Ser Glu Arg Trp Ser Gly Ser Ala Ser Arg Asn Gln His Gly Ser
2255             2260                2265

Ala Arg Glu Gln Ser Arg Asp Gly Ser Arg His Pro Gly Ser His
2270             2275                2280

Gln Glu Asp Arg Ala Gly His Gly His Ser Ala Asp Ser Ser Arg
2285             2290                2295

Gln Ser Gly Thr Arg His Thr Glu Ser Ser Arg Gly Gln Ala
2300             2305                2310

Ala Ser Ser His Glu Gln Ala Arg Ser Ser Ala Gly Glu Arg His
2315             2320                2325

Gly Ser Arg His Gln Leu Gln Ser Ala Asp Ser Ser Arg His Ser
2330             2335                2340

Gly Ile Gly His Gly Gln Ala Ser Ser Ala Val Arg Asp Ser Gly
2345             2350                2355

His Arg Gly Ser Ser Gly Ser Gln Ala Ile Asp Ser Glu Gly His
2360             2365                2370

Ser Glu Asp Ser Asp Thr Gln Ser Val Ser Ala Gln Gly Gln Ala
2375             2380                2385

Gly Pro His Gln Arg Ser His Lys Glu Ser Ala Arg Gly Gln Ser
2390             2395                2400

Gly Glu Ser Ser Gly Arg Ser Gly Ser Phe Leu Tyr Gln Val Ser
2405             2410                2415

Thr His Glu Gln Pro Glu Ser Thr His Gly Gln Ser Ala Pro Ser
2420             2425                2430

Thr Gly Gly Arg Gln Gly Ser His His Asp Gln Ala Gln Asp Ser
2435             2440                2445

Ser Arg His Ser Ala Ser Gln Glu Gly Gln Asp Thr Ile Arg Gly
2450             2455                2460
```

```
His Pro Gly Pro Ser Arg Gly Gly Arg Gln Gly Ser His His Lys
2465                2470                2475

Gln Ser Val Asp Arg Ser Gly His Ser Gly Ser His His Ser His
    2480                2485                2490

Thr Thr Ser Gln Gly Arg Ser Asp Ala Ser Arg Gly Gln Ser Gly
        2495                2500                2505

Ser Arg Ser Ala Ser Arg Gln Thr His Asp Lys Glu Gln Ser Gly
    2510                2515                2520

Asp Gly Ser Arg His Ser Gly Ser Arg His His Glu Ala Ser Ser
    2525                2530                2535

Trp Ala Asp Ser Ser Arg His Ser Gln Ala Gly Gln Gly Gln Ser
    2540                2545                2550

Glu Gly Ser Arg Thr Ser Arg Arg Gln Gly Ser Ser Phe Ser Gln
    2555                2560                2565

Asp Ser Asp Ser Glu Gly His Ser Glu Asp Ser Glu Arg Arg Ser
    2570                2575                2580

Gly Ser Ala Ser Arg Asn His Arg Gly Ser Ala Gln Glu Gln Ser
    2585                2590                2595

Arg Asp Gly Ser Arg His Pro Arg Ser His His Glu Asp Arg Ala
    2600                2605                2610

Gly His Gly His Ser Ala Asp Ser Ser Arg Gln Ser Gly Thr His
    2615                2620                2625

His Ala Gln Asn Ser Ser Gly Gly Gln Ala Ala Ser Phe His Glu
    2630                2635                2640

Gln Ala Arg Ser Ser Ala Gly Glu Arg His Gly Ser His His Gln
    2645                2650                2655

Gln Ser Ala Asp Ser Ser Arg His Ser Gly Ile Gly His Gly Gln
    2660                2665                2670

Ala Ser Ser Ala Val Arg Asp Ser Gly His Arg Gly Ser Ser Gly
    2675                2680                2685

Ser Gln Ala Ser Asp Ser Gly His Ser Glu Asp Ser Asp Thr
    2690                2695                2700

Gln Ser Val Ser Ala His Gly Gln Ala Gly Pro His Gln Gln Ser
    2705                2710                2715

His Gln Glu Ser Thr Arg Gly Arg Ser Ala Glu Arg Ser Gly Arg
    2720                2725                2730

Ser Gly Ser Phe Leu Tyr Gln Val Ser Thr His Glu Gln Ser Glu
    2735                2740                2745

Ser Ala His Gly Arg Thr Gly Pro Ser Thr Gly Gly Arg Gln Gly
    2750                2755                2760

Ser Arg His Glu Gln Ala Arg Asp Ser Ser Arg His Ser Ala Ser
    2765                2770                2775

Gln Glu Gly Gln Asp Thr Ile His Gly His Pro Gly Ser Arg Arg
    2780                2785                2790

Gly Gly Arg Gln Gly Ser Tyr His Glu Gln Ser Val Asp Arg Ser
    2795                2800                2805

Gly His Ser Gly Ser His His Ser His Thr Thr Ser Gln Gly Arg
    2810                2815                2820

Ser Asp Ala Ser His Gly Gln Ser Gly Ser Arg Ser Ala Ser Arg
    2825                2830                2835

Gln Thr Arg Asn Glu Gln Gln Ser Gly Asp Gly Ser Arg His Ser
    2840                2845                2850

Gly Ser Ser His His Glu Ala Ser Thr Gln Ala Asp Ser Ser Arg
```

2855                2860                2865

His Ser Gln Ser Gly Gln Gly Glu Ser Ala Gly Ser Arg Arg Ser
        2870                2875                2880

Arg Arg Gln Gly Ser Ser Val Ser Gln Asp Ser Asp Ser Glu Ala
        2885                2890                2895

Tyr Pro Glu Asp Ser Glu Arg Arg Ser Glu Ser Ala Ser Arg Asn
        2900                2905                2910

Arg His Gly Ser Ser Arg Glu Gln Ser Arg Asp Gly Ser Arg His
        2915                2920                2925

Pro Gly Ser Ser His Arg Asp Thr Thr Arg His Val Gln Ser Ser
        2930                2935                2940

Pro Val Gln Ser Asp Ser Ser Thr Ala Lys Glu His Gly His Phe
        2945                2950                2955

Ser Ser Leu Ser Gln Asp Ser Ala Tyr Arg Ser Gly Ile Gln Ser
        2960                2965                2970

Arg Gly Ser Pro His Ser Ser Ser Ser Tyr His Tyr Gln Ser Glu
        2975                2980                2985

Gly Thr Glu Arg Gln Lys Gly Gln Ser Gly Leu Val Trp Arg His
        2990                2995                3000

Gly Ser Tyr Gly Ser Ala Asp Tyr Asp Tyr Gly Glu Ser Gly Phe
        3005                3010                3015

Arg His Ser Gln His Gly Ser Val Ser Tyr Asn Ser Asn Pro Val
        3020                3025                3030

Val Phe Lys Glu Arg Ser Asp Ile Cys Lys Ala Ser Ala Phe Gly
        3035                3040                3045

Lys Asp His Pro Arg Tyr Tyr Ala Thr Tyr Ile Asn Lys Asp Pro
        3050                3055                3060

Gly Leu Cys Gly His Ser Ser Asp Ile Ser Lys Gln Leu Gly Phe
        3065                3070                3075

Ser Gln Ser Gln Arg Tyr Tyr Tyr Glu
        3080                3085

<210> SEQ ID NO 16
<211> LENGTH: 2764
<212> TYPE: PRT
<213> ORGANISM: Pan troglodytes

<400> SEQUENCE: 16

Met Ser Thr Leu Leu Glu Asn Ile Phe Ala Ile Ile Asn Leu Phe Lys
1               5                   10                  15

Gln Tyr Ser Lys Lys Asp Lys Asn Thr Asp Thr Leu Ser Lys Lys Glu
            20                  25                  30

Leu Lys Glu Leu Leu Glu Lys Glu Phe Arg Gln Ile Leu Lys Asn Pro
        35                  40                  45

Asp Asp Pro Asp Met Val Asp Val Phe Met Asp His Leu Asp Ile Asp
    50                  55                  60

His Asn Lys Lys Ile Asp Phe Thr Glu Phe Leu Leu Met Val Phe Lys
65                  70                  75                  80

Leu Ala Gln Ala Tyr Tyr Glu Ser Thr Arg Lys Glu Asn Leu Pro Ile
                85                  90                  95

Ser Gly His Lys His Arg Lys His Ser His His Asp Lys His Glu Asp
            100                 105                 110

Asn Lys Gln Glu Glu Asn Lys Glu Asn Arg Lys Arg Pro Ser Ser Leu
        115                 120                 125

```
Glu Arg Arg Asn Asn Arg Lys Gly Asn Lys Gly Arg Ser Lys Ser Pro
130                 135                 140

Arg Glu Thr Gly Gly Lys Arg His Glu Ser Ser Glu Lys Lys Glu
145                 150                 155                 160

Arg Lys Gly Tyr Ser Pro Thr His Arg Glu Glu Tyr Gly Lys Asn
                165                 170                 175

His His Asn Ser Ser Lys Lys Gln Lys Asn Lys Thr Glu Asn Thr Arg
                180                 185                 190

Leu Glu Asp Asn Arg Lys Arg Leu Ser Glu Arg Leu Glu Glu Lys Glu
                195                 200                 205

Asn Asn Glu Glu Gly Gly Tyr Asp Tyr Glu Asn Thr Gly Arg Met Thr
210                 215                 220

Gln Lys Trp Ile Gln Ser Gly His Ile Ala Thr Tyr Tyr Thr Ile Gln
225                 230                 235                 240

Asp Glu Ala Tyr Asp Thr Thr Asp Asn Leu Leu Glu Glu Asn Lys Ile
                245                 250                 255

Tyr Glu Arg Ser Arg Ser Ser Asp Asp Lys Ser Ser Ser Gln Val Asn
                260                 265                 270

Arg Ser Arg His Glu Asn Thr Ser Gln Val Pro Leu Gln Glu Ser Arg
                275                 280                 285

Thr Arg Lys Arg Arg Gly Ser Arg Val Ser Gln Asp Arg Asp Ser Glu
290                 295                 300

Gly His Ser Glu Asp Ser Glu Arg His Ser Gly Ser Ala Ser Arg Asn
305                 310                 315                 320

His Pro Gly Ser Ala Arg Gln Gln Ser Arg Asp Gly Ser Arg His Pro
                325                 330                 335

Arg Ser His Asp Glu Asp Arg Ala Ser His Gly His Ser Ala Asp Ser
                340                 345                 350

Ser Arg Gln Ser Gly Thr Arg His Ala Glu Thr Ser Ser Arg Gly Gln
                355                 360                 365

Thr Ala Ser Ser His Glu Gln Ala Arg Ser Ser Pro Gly Glu Arg His
370                 375                 380

Gly Ser Arg His Gln Gln Ser Ala Asp Ser Ser Arg His Ser Ala Thr
385                 390                 395                 400

Gly Arg Gly Gln Ala Ser Ser Ala Val Ser Asp Arg Gly Pro Arg Gly
                405                 410                 415

Ser Ser Gly Ser Gln Ala Ser Asp Ser Glu Gly His Ser Glu Asn Ser
                420                 425                 430

Asp Thr Gln Ser Val Ser Gly His Gly Lys Ala Gly Pro Arg Gln Gln
                435                 440                 445

Ser His Gln Glu Ser Ala Arg Gly Arg Ser Gly Glu Arg Ser Gly His
                450                 455                 460

Ser Gly Ser Phe Leu Tyr Gln Val Ser Thr His Glu Gln Ser Asp Ser
465                 470                 475                 480

Ala His Gly Arg Thr Gly Thr Ser Thr Gly Gly Arg Gln Gly Ser His
                485                 490                 495

His Glu Gln Ala Arg Asp Ser Ser Arg His Ser Ala Ser Gln Glu Gly
                500                 505                 510

Gln Asp Thr Ile Arg Gly His Pro Gly Ser Ser Arg Gly Gly Arg Gln
                515                 520                 525

Gly Ser His His Glu Gln Leu Val Asn Arg Ser Gly His Ser Gly Ser
530                 535                 540

His His Ser His Thr Thr Ser Gln Gly Arg Ser Asp Ala Ser His Gly
```

```
         545                 550                 555                 560
Gln Ser Gly Ser Arg Ser Ala Ser Arg Gln Thr Arg Asn Glu Glu Gln
                565                 570                 575
Ser Gly Asp Gly Ser Arg His Ser Gly Ser Arg His His Glu Ala Ser
                580                 585                 590
Ser Gln Ala Asp Ser Ser Arg His Ser Gln Val Gly Gln Gly Gln Ser
                595                 600                 605
Ser Gly Pro Arg Thr Ser Ser His Gln Gly Ser Ser Val Ser Gln Asp
                610                 615                 620
Ser Asp Ser Glu Gly His Ser Glu Asp Ser Glu Arg Trp Ser Gly Ser
625                 630                 635                 640
Ala Ser Arg Asn His His Gly Ser Ala Arg Glu Gln Ser Arg Asp Gly
                645                 650                 655
Ser Arg His Pro Arg Ser His His Glu Asp Arg Ala Gly His Gly His
                660                 665                 670
Ser Ala Asp Ser Ser Arg Gln Ser Gly Thr Arg His Thr Glu Ser Ser
                675                 680                 685
Ser Arg Gly Gln Ala Val Ser Ser His Glu Gln Ala Arg Ser Ser Pro
                690                 695                 700
Gly Glu Arg His Gly Ser Arg His Gln Gln Ser Ala Asp Ser Ser Arg
705                 710                 715                 720
His Ser Gly Ile Gly His Gly Gln Ala Ser Ser Ala Val Arg Asp Ser
                725                 730                 735
Gly His Arg Gly Ser Ser Gly Ser Gln Ala Ile Asp Ser Glu Gly His
                740                 745                 750
Ser Glu Asp Ser Asp Thr Gln Ser Val Ser Ser His Gly Gln Ala Gly
                755                 760                 765
Pro His Gln Gln Ser His Lys Glu Ser Ala Arg Gly Ser Gly Glu
                770                 775                 780
Ser Ser Gly Arg Ser Gly Ser Phe Leu Tyr Gln Val Ser Ser His Glu
785                 790                 795                 800
Gln Ser Glu Ser Thr Tyr Gly Gln Thr Ala Pro Ser Thr Gly Gly Arg
                805                 810                 815
Gln Gly Ser Arg His Glu Gln Ala Arg Asn Ser Ser Arg His Ser Ala
                820                 825                 830
Ser Gln Asp Gly Gln Asp Thr Ile Arg Gly His Pro Gly Ser Ser Arg
                835                 840                 845
Gly Gly Arg Gln Gly Ser Tyr His Glu Gln Ser Val Asp Arg Ser Gly
                850                 855                 860
His Ser Gly Tyr His His Ser His Thr Thr Pro Gln Gly Arg Ser Asn
865                 870                 875                 880
Ala Ser His Gly Gln Ser Gly Ser Arg Ser Ala Ser Arg Gln Thr Arg
                885                 890                 895
Asn Glu Glu Gln Ser Gly Asp Gly Ser Arg His Ser Gly Ser Arg His
                900                 905                 910
His Glu Ala Ser Ser Arg Ala Asp Ser Ser Arg His Ser Gln Val Gly
                915                 920                 925
Gln Gly Gln Ser Ser Gly Pro Arg Thr Ser Arg Asn Gln Gly Ser Ser
                930                 935                 940
Val Ser Gln Asp Ser Asp Ser Gln Gly His Ser Glu Asp Ser Glu Arg
945                 950                 955                 960
Trp Ser Gly Ser Ala Ser Arg Asn His His Gly Ser Ala Trp Glu Gln
                965                 970                 975
```

-continued

Ser Arg Asp Gly Ser Arg His Pro Gly Ser His Gln Glu Asp Arg Ala
        980                 985                 990

Gly His Gly His Ser Ala Asp Ser  Ser Arg Gln Ser Gly  Thr His His
    995                 1000                 1005

Thr Glu  Ser Ser Ser Arg Gly  Gln Ala Ala Ser Ser  His Glu His
    1010                 1015                 1020

Ala Arg  Ser Ser Ala Gly Glu  Arg His Gly Ser His  His Gln Gln
    1025                 1030                 1035

Ser Ala  Asp Ser Ser Arg His  Ser Gly Ile Gly His  Gly Gln Ala
    1040                 1045                 1050

Ser Ser  Ala Val Arg Asp Ser  Gly His Arg Gly Ser  Ser Gly Ser
    1055                 1060                 1065

Gln Ala  Ser Asp Ser Glu Gly  His Ser Glu Asp Ser  Asp Thr Gln
    1070                 1075                 1080

Ser Leu  Ser Ala His Gly Gln  Ala Gly Pro His Gln  Gln Ser His
    1085                 1090                 1095

Gln Glu  Ser Thr Arg Gly Arg  Ser Ala Glu Arg Ser  Gly Arg Ser
    1100                 1105                 1110

Gly Ser  Phe Leu Tyr Gln Val  Ser Thr His Glu Gln  Ser Glu Ser
    1115                 1120                 1125

Ala His  Gly Arg Thr Gly Thr  Ser Thr Gly Gly Arg  Lys Arg Ser
    1130                 1135                 1140

Leu His  Glu Gln Ala Arg Asp  Ser Ser Arg His Ser  Val Ser Gln
    1145                 1150                 1155

Glu Gly  Gln Asp Thr Ile His  Gly His Ala Gly Ser  Ser Ser Gly
    1160                 1165                 1170

Gly Arg  Gln Gly Ser His Tyr  Glu Gln Leu Val Asp  Arg Ser Gly
    1175                 1180                 1185

His Ser  Gly Ser His His Ser  His Thr Thr Ser Gln  Gly Arg Ser
    1190                 1195                 1200

Asp Ala  Tyr His Gly Gln Ser  Gly Ser Arg Ser Ala  Ser Arg Gln
    1205                 1210                 1215

Thr His  Asn Asp Glu Gln Ser  Gly Asp Gly Phe Arg  His Ser Gly
    1220                 1225                 1230

Ser His  His His Glu Ala Ser  Ser Arg Ala Asp Ser  Ser Arg His
    1235                 1240                 1245

Ser Gln  Val Gly Gln Gly Gln  Ser Glu Gly Pro Arg  Thr Ser Arg
    1250                 1255                 1260

His Arg  Glu Ser Ser Val Ser  Gln Asp Ser Asp Ser  Glu Gly His
    1265                 1270                 1275

Ser Glu  Asp Ser Glu Arg Trp  Ser Gly Ser Ala Ser  Arg Asn His
    1280                 1285                 1290

His Gly  Ser Ala Arg Glu Gln  Ser Arg Asp Gly Ser  Arg His Pro
    1295                 1300                 1305

Arg Ser  His His Glu Asp Arg  Ala Gly His Gly His  Ser Ala Asp
    1310                 1315                 1320

Ser Ser  Arg Gln Ser Gly Thr  Arg His Thr Gln Thr  Ser Ser Gly
    1325                 1330                 1335

Gly Gln  Ala Ala Ser Ser His  Glu Gln Gly Arg Ser  Ser Ala Gly
    1340                 1345                 1350

Glu Arg  His Gly Ser Arg His  Gln Gln Ser Ala Asp  Ser Ser Arg
    1355                 1360                 1365

```
His Ser Gly Ile Gly His Gly Gln Ala Ser Ser Ala Val Arg Asp
    1370            1375                1380

Ser Gly His Arg Gly Tyr Ser Gly Ser Gln Ala Ser Asp Ser Glu
1385                1390                1395

Gly His Ser Glu Asp Ser Asp Thr Gln Ser Val Ser Ala His Gly
    1400            1405                1410

Gln Ala Gly Ser His Gln Gln Ser His Gln Glu Ser Ala Arg Gly
1415                1420                1425

Arg Ser Gly Glu Arg Ser Gly Arg Ser Gly Ser Phe Leu Tyr Gln
    1430            1435                1440

Val Ser Thr His Glu Gln Ser Glu Ser Ser His Gly Trp Thr Gly
1445                1450                1455

Pro Ser Thr Arg Gly Arg Gln Gly Ser Arg His Glu Gln Ala Gln
    1460            1465                1470

Asp Ser Ser Arg His Ser Ala Ser Gln Glu Gly Gln Asp Thr Ile
1475                1480                1485

Arg Gly His Pro Gly Pro Ser Arg Gly Gly Arg Gln Gly Tyr His
    1490            1495                1500

His Glu Gln Ser Val Asp Ser Ser Gly His Ser Gly Ser His His
1505                1510                1515

Ser His Ile Thr Ser Gln Gly Ser Ser His Ala Ser His Gly Gln
    1520            1525                1530

Ser Gly Ser Arg Ser Ala Ser Arg Thr Thr Arg Asn Asp Glu Gln
1535                1540                1545

Ser Val Asp Gly Ser Arg His Ser Gly Ser Arg His His Glu Ala
    1550            1555                1560

Ser Thr His Ala Asp Ile Ser Arg His Ser Gln Ala Gly Gln Gly
1565                1570                1575

Gln Ser Glu Gly Ser Arg Thr Ser Arg Arg Gln Gly Ser Ser Val
    1580            1585                1590

Ser Gln Asp Ser Asp Ser Glu Gly His Ser Glu Asp Ser Glu Arg
1595                1600                1605

Trp Ser Gly Ser Ala Ser Arg Asn His Arg Gly Ser Ala Gln Glu
    1610            1615                1620

Gln Ser Arg Asp Gly Ser Arg His Pro Arg Ser His His Glu Asp
1625                1630                1635

Arg Ala Gly His Gly His Ser Ala Asp Ser Ser Arg Gln Ser Gly
    1640            1645                1650

Thr His His Ala Glu Thr Ser Ser Gly Gly Gln Ala Ala Ser Ser
1655                1660                1665

Arg Glu Gln Ala Arg Ser Ser Pro Gly Glu Arg His Gly Ser Arg
    1670            1675                1680

His Gln Gln Ser Ala Asp Ser Ser Arg His Ser Gly Ile Arg Arg
1685                1690                1695

Gly Gln Ala Ser Ser Ala Val Arg Asp Ser Gly His Trp Gly Ser
    1700            1705                1710

Ser Gly Ser Gln Ala Ser Asp Ser Glu Gly His Ser Glu Glu Ser
1715                1720                1725

Asp Thr Gln Ser Val Ser Gly His Gly Gln Asp Gly Pro His Gln
    1730            1735                1740

Gln Ser His Gln Glu Ser Ala Arg Asp Arg Ser Gly Gly Arg Ser
1745                1750                1755

Gly Arg Ser Gly Ser Phe Leu Tyr Gln Val Ser Thr His Glu Gln
```

-continued

```
             1760                1765                 1770

Ser Glu Ser Thr His Gly Gln Thr Gly Thr Ser Thr Gly Gly Arg
    1775                1780                 1785

Gln Gly Ser His His Glu Gln Ala Arg Asp Ser Arg His Ser
    1790                1795                1800

Ala Ser Gln Glu Gly Gln Asp Thr Ile His Ala His Pro Gly Ser
    1805                1810                1815

Ser Arg Gly Gly Arg Gln Gly Ser His His Glu Gln Ser Val Asp
    1820                1825                1830

Thr Ser Gly His Ser Gly Ser His His Ser His Thr Thr Ser Gln
    1835                1840                 1845

Gly Arg Ser Asp Ala Ser His Gly Gln Ser Gly Ser Arg Ser Ala
    1850                1855                 1860

Ser Arg Gln Thr Arg Asn Asp Glu Gln Ser Gly Asp Gly Ser Arg
    1865                1870                1875

His Ser Gly Ser His His His Glu Ala Phe Thr Gln Ala Asp Ser
    1880                1885                 1890

Ser Arg His Ser Gln Ser Gly Gln Gly Glu Ser Ala Gly Ser Arg
    1895                1900                 1905

Arg Ser Arg Arg Gln Gly Ser Ser Val Ser Gln Asp Ser Asp Ser
    1910                1915                1920

Gln Gly His Ser Glu Asp Ser Glu Arg Trp Ser Gly Ser Ala Ser
    1925                1930                 1935

Arg Asn Gln His Gly Ser Ala Arg Glu Gln Ser Arg Asp Gly Ser
    1940                1945                1950

Arg His Pro Gly Ser His Gln Glu Asp Arg Ala Gly His Gly His
    1955                1960                 1965

Ser Ala Asp Ser Ser Arg Gln Ser Gly Thr Arg His Thr Glu Ser
    1970                1975                1980

Ser Ser Arg Gly Gln Ala Ala Ser Ser His Glu Gln Ala Arg Ser
    1985                1990                 1995

Ser Ala Gly Glu Arg His Gly Ser Arg His Gln Leu Gln Ser Ala
    2000                2005                 2010

Asp Ser Ser Arg His Ser Gly Ile Gly His Gly Gln Ala Ser Ser
    2015                2020                2025

Ala Val Arg Asp Ser Gly His Arg Gly Ser Ser Gly Ser Gln Ala
    2030                2035                 2040

Ile Asp Ser Glu Gly His Ser Glu Asp Ser Asp Thr Gln Ser Val
    2045                2050                 2055

Ser Ala Gln Gly Gln Ala Gly Pro His Gln Arg Ser His Lys Glu
    2060                2065                2070

Ser Ala Arg Gly Gln Ser Gly Glu Ser Ser Gly Arg Ser Gly Ser
    2075                2080                 2085

Phe Leu Tyr Gln Val Ser Thr His Glu Gln Pro Glu Ser Thr His
    2090                2095                 2100

Gly Gln Ser Ala Pro Ser Thr Gly Gly Arg Gln Gly Ser His His
    2105                2110                2115

Asp Gln Ala Gln Asp Ser Ser Arg His Ser Ala Ser Gln Glu Gly
    2120                2125                2130

Gln Asp Thr Ile Arg Gly His Pro Gly Pro Ser Arg Gly Gly Arg
    2135                2140                2145

Gln Gly Ser His His Lys Gln Ser Val Asp Arg Ser Gly His Ser
    2150                2155                2160
```

-continued

```
Gly Ser His His Ser His Thr Thr Ser Gln Gly Arg Ser Asp Ala
    2165                2170                2175

Ser Arg Gly Gln Ser Gly Ser Arg Ser Ala Ser Arg Gln Thr His
    2180                2185                2190

Asp Lys Glu Gln Ser Gly Asp Gly Ser Arg His Ser Gly Ser Arg
    2195                2200                2205

His His Glu Ala Ser Ser Trp Ala Asp Ser Ser Arg His Ser Gln
    2210                2215                2220

Ala Gly Gln Gly Gln Ser Glu Gly Ser Arg Thr Ser Arg Arg Gln
    2225                2230                2235

Gly Ser Ser Phe Ser Gln Asp Ser Asp Ser Glu Gly His Ser Glu
    2240                2245                2250

Asp Ser Glu Arg Arg Ser Gly Ser Ala Ser Arg Asn His Arg Gly
    2255                2260                2265

Ser Ala Gln Glu Gln Ser Arg Asp Gly Ser Arg His Pro Arg Ser
    2270                2275                2280

His His Glu Asp Arg Ala Gly His Gly His Ser Ala Asp Ser Ser
    2285                2290                2295

Arg Gln Ser Gly Thr His His Ala Gln Asn Ser Ser Gly Gly Gln
    2300                2305                2310

Ala Ala Ser Phe His Glu Gln Ala Arg Ser Ser Ala Gly Glu Arg
    2315                2320                2325

His Gly Ser His His Gln Gln Ser Ala Asp Ser Ser Arg His Ser
    2330                2335                2340

Gly Ile Gly His Gly Gln Ala Ser Ser Ala Val Arg Asp Ser Gly
    2345                2350                2355

His Arg Gly Ser Ser Gly Ser Gln Ala Ser Asp Ser Glu Gly His
    2360                2365                2370

Ser Glu Asp Ser Asp Thr Gln Ser Val Ser Ala His Gly Gln Ala
    2375                2380                2385

Gly Pro His Gln Gln Ser His Gln Glu Ser Thr Arg Gly Arg Ser
    2390                2395                2400

Ala Glu Arg Ser Gly Arg Ser Gly Ser Phe Leu Tyr Gln Val Ser
    2405                2410                2415

Thr His Glu Gln Ser Glu Ser Ala His Gly Arg Thr Gly Pro Ser
    2420                2425                2430

Thr Gly Gly Arg Gln Gly Ser Arg His Glu Gln Ala Arg Asp Ser
    2435                2440                2445

Ser Arg His Ser Ala Ser Gln Glu Gly Gln Asp Thr Ile His Gly
    2450                2455                2460

His Pro Gly Ser Arg Arg Gly Gly Arg Gln Gly Ser Tyr His Glu
    2465                2470                2475

Gln Ser Val Asp Arg Ser Gly His Ser Gly Ser His His Ser His
    2480                2485                2490

Thr Thr Ser Gln Gly Arg Ser Asp Ala Ser His Gly Gln Ser Gly
    2495                2500                2505

Ser Arg Ser Ala Ser Arg Gln Thr Arg Asn Glu Gln Gln Ser Gly
    2510                2515                2520

Asp Gly Ser Arg His Ser Gly Ser Ser His His Glu Ala Ser Thr
    2525                2530                2535

Gln Ala Asp Ser Ser Arg His Ser Gln Ser Gly Gln Gly Glu Ser
    2540                2545                2550
```

```
Ala Gly Ser Arg Arg Ser Arg Arg Gln Gly Ser Ser Val Ser Gln
    2555                2560                2565

Asp Ser Asp Ser Glu Ala Tyr Pro Glu Asp Ser Glu Arg Arg Ser
    2570                2575                2580

Glu Ser Ala Ser Arg Asn Arg His Gly Ser Ser Arg Glu Gln Ser
    2585                2590                2595

Arg Asp Gly Ser Arg His Pro Gly Ser Ser His Arg Asp Thr Thr
    2600                2605                2610

Arg His Val Gln Ser Ser Pro Val Gln Ser Asp Ser Ser Thr Ala
    2615                2620                2625

Lys Glu His Gly His Phe Ser Ser Leu Ser Gln Asp Ser Ala Tyr
    2630                2635                2640

Arg Ser Gly Ile Gln Ser Arg Gly Ser Pro His Ser Ser Ser Ser
    2645                2650                2655

Tyr His Tyr Gln Ser Glu Gly Thr Glu Arg Gln Lys Gly Gln Ser
    2660                2665                2670

Gly Leu Val Trp Arg His Gly Ser Tyr Gly Ser Ala Asp Tyr Asp
    2675                2680                2685

Tyr Gly Glu Ser Gly Phe Arg His Ser Gln His Gly Ser Val Ser
    2690                2695                2700

Tyr Asn Ser Asn Pro Val Val Phe Lys Glu Arg Ser Asp Ile Cys
    2705                2710                2715

Lys Ala Ser Ala Phe Gly Lys Asp His Pro Arg Tyr Tyr Ala Thr
    2720                2725                2730

Tyr Ile Asn Lys Asp Pro Gly Leu Cys Gly His Ser Ser Asp Ile
    2735                2740                2745

Ser Lys Gln Leu Gly Phe Ser Gln Ser Gln Arg Tyr Tyr Tyr Tyr
    2750                2755                2760

Glu

<210> SEQ ID NO 17
<211> LENGTH: 1656
<212> TYPE: PRT
<213> ORGANISM: Bos taurus

<400> SEQUENCE: 17

Met Ser Thr Leu Leu Glu Asn Ile Asn Asp Ile Ile Lys Ile Phe His
1               5                   10                  15

Lys Tyr Ser Lys Thr Asp Lys Glu Thr Asp Thr Leu Ser Glu Lys Glu
                20                  25                  30

Leu Lys Glu Leu Val Glu Val Glu Phe Arg Pro Ile Leu Lys Asn Pro
            35                  40                  45

Gly Asp Pro Asp Thr Ala Glu Val Phe Met Tyr Asn Leu Asp Arg Asp
        50                  55                  60

His Asn Asn Lys Ile Asp Phe Thr Glu Phe Phe Leu Met Val Phe Lys
65                  70                  75                  80

Val Ala Gln Val Tyr Tyr Ser Tyr Thr Gln Arg Gln Asn Leu Gln Arg
                85                  90                  95

Ala Gly Gln Lys Gln Lys Lys Cys Thr Tyr His Tyr Gly Asp Glu Glu
            100                 105                 110

Asp Asp Thr Glu Glu Asp Lys Glu Glu Thr Glu Arg Lys Tyr Ser His
        115                 120                 125

Ser Arg Ser Asp Gly Lys Thr Gln Asp Arg Ser Lys Pro Arg Gly
    130                 135                 140
```

```
Arg Gly Lys Lys Arg His Gly Ser Lys Ser Ser Lys Gln Arg Arg
145                 150                 155                 160

Gly Asp Thr Pro Thr Ser Gly Leu Arg His Gly Cys Ser Lys Lys His
                165                 170                 175

Glu Ser Arg Arg Glu Lys Lys Arg Arg Pro Ser Ser Thr Glu Pro Lys
            180                 185                 190

Glu Arg Arg His Met Ser Ser Val Ser Pro Thr Arg Gly Tyr Glu Glu
        195                 200                 205

Lys Glu Glu Glu His Gly Tyr Glu Asn Lys Gly Lys Thr Ser Ala Lys
    210                 215                 220

Cys Ile Gly Ser Glu Tyr Asp Asp Ser Tyr Gln Val Cys Glu Asp Lys
225                 230                 235                 240

Val Thr Thr Asn Phe Gln Pro Ser His Ser Lys Asn Tyr Gly Ser Asn
                245                 250                 255

Ile Thr Lys Gly Arg Asp Thr Glu Gly His Ser Arg Asp Thr Gly Arg
                260                 265                 270

Lys Ser Val Phe Thr His Ala Arg Ser Gly Ser Ser Arg Asn Gln
            275                 280                 285

Asn Gly Ser Val Gln Thr His Thr Gly Asp Asn Ser Thr His Ser Glu
    290                 295                 300

Ser Gln Gln Glu Thr Asn Ser Glu Ser Val His Arg Arg Ser Arg Asn
305                 310                 315                 320

Thr Gly Gln Arg Gln Gly Ser His His Glu Gln Ser Arg Asp Ser Ser
                325                 330                 335

Arg His Ser Gly Thr Arg His Gly Gln Pro Ser Thr Gly Ser Gly Gly
            340                 345                 350

Ser Arg His Arg Glu Ser Ser Val Ser Gln Ala Ser Asp Ser Glu Gly
            355                 360                 365

His Ser Glu Asp Ser Gly Arg Gln Ser Val Thr Thr His Gly Arg Pro
    370                 375                 380

Gly Ser Ser Ser Arg Asn Gln His Gly Ser Ser Gln Gly Gln Thr Gly
385                 390                 395                 400

Asp Ser Ser Arg His Ser Glu Ser His Gln Gly Arg His Ser Asp Ser
                405                 410                 415

Leu Gln Arg Arg Ser Gly Thr Ser Thr Gly Gln Arg Gln Gly Ser His
            420                 425                 430

His Glu Gln Ser Arg Asp Ser Ser Arg His Ser Gly Thr Gln Gln Gly
        435                 440                 445

Gln Thr Ser Thr Gly Ser Gly Ser Ser Arg His Arg Asp Ser Ser Val
    450                 455                 460

Ser Gln Ala Ser Asp Ser Glu Gly His Ser Glu Asp Ser Gly Arg Gln
465                 470                 475                 480

Ser Val Thr Thr His Gly Arg Pro Gly Ser Ser Ser Arg Asn Gln His
                485                 490                 495

Gly Ser Ser His Gly Gln Thr Gly Asp Ser Ser Arg His Ser Glu Ser
            500                 505                 510

His Gln Arg Ser His Ser Glu Ala Val His Glu Arg Ser Gly Ser Ser
        515                 520                 525

Thr Gly Gln Arg Gln Arg Ser His His Glu Gln Ser Arg Asp Ser Ser
    530                 535                 540

Arg His Ser Gly Thr Gly His Gly Gln Ile Ser Ala Glu Ser Gly Asn
545                 550                 555                 560

Gly Arg His Arg Glu Ser Ser Val Ser Gln Ala Ser Asp Ser Glu Gly
```

-continued

```
              565                 570                 575

His Ala Arg Asp Ser Gly Arg His Ser Glu Thr Thr His Gly Arg Tyr
            580                 585                 590

Gly Ser Ser Ser Arg Asn Gln His Gly Ser Ser His Gly Gln Thr Gly
            595                 600                 605

Asp Ser Tyr Arg His Ser Glu Thr Asn Gln Gly Arg His Asn Lys Arg
            610                 615                 620

His Thr Arg Asp Ser Gly Arg His Ser Glu Thr Thr His Gly Arg Pro
625                 630                 635                 640

Gly Ser Ser Ser Arg Asn Gln His Gly Ser Ser His Gly Gln Ser Gly
            645                 650                 655

Asp Ser Ser Arg His Ser Glu Ser His Gln Glu Arg His Ser Glu Ser
            660                 665                 670

Val His Gly Arg Ser Gly Ser Ser Thr Gly Gln Arg Gln Gly Ser His
            675                 680                 685

His Glu Gln Ser Arg Asp Ser Ser Arg His Ser Gly Thr Arg His Gly
            690                 695                 700

Gln Thr Ser Ala Glu Ser Gly Asn Gly Arg His Arg Glu Ser Ser Val
705                 710                 715                 720

Ser Gln Ala Ser Asp Ser Glu Gly His Thr Arg Asp Ser Gly Arg His
            725                 730                 735

Ser Glu Thr Thr His Gly Arg Pro Gly Ser Ser Arg Asn Gln His
            740                 745                 750

Gly Ser Ser Gln Gly Gln Thr Gly Asp Ser Ser Arg Tyr Ser Ala Tyr
            755                 760                 765

His Gln Gly Arg His Ser Glu Ser Val His Glu Arg Ser Ala Ser Arg
            770                 775                 780

Thr Gly Gln Arg Gln Gly Ser His His Glu Gln Ser Arg Asp Ser Ser
785                 790                 795                 800

Arg Gln Ser Gly Thr Gly His Gly His Thr Ser Ala Gly Ser Gly Asn
            805                 810                 815

Gly Arg His Arg Glu Ser Ser Val Ser Gln Ser Ser Asp Arg Glu Gly
            820                 825                 830

His Ala Arg Asp Ser Gly Arg Gln Ser Val Thr Thr His Gly Arg Pro
            835                 840                 845

Gly Ser Ser Ser Arg Asn Gln His Val Ser Ser His Gly Gln Ile Gly
            850                 855                 860

Asp Ser Ser His Ser Glu Thr Asn Gln Gly Ser His Asn Glu Arg
865                 870                 875                 880

His Thr Arg Asp Ser Gly Arg His Ser Glu Thr Thr His Gly Arg Leu
            885                 890                 895

Gly Ser Ser Ser Arg Asn Gln His Gly Ser Val His Gly Gln Thr Arg
            900                 905                 910

Asp Ser Pro Arg His Ser Glu Ser His Gln Glu Arg His Ser Glu Ser
            915                 920                 925

Val His Gly Arg Ser Gly Ser Ser Thr Gly Gln Arg Gln Glu Ser His
            930                 935                 940

His Glu Gln Ser Arg Asp Ser Ser Arg Gln Ser Gly Thr Gly His Gly
945                 950                 955                 960

His Thr Ser Ala Gly Ser Gly Asn Ser Arg His Arg Glu Ser Ser Val
            965                 970                 975

Ser Gln Ala Ser Asp Ser Glu Gly His Ser Glu Asp Ser Gly Arg Gln
            980                 985                 990
```

```
Asn Val Thr Thr His Gly Arg Pro  Gly Ser Ser Ser Arg  Asn Gln His
        995             1000                 1005

Gly Ser  Ser Gln Gly Gln Thr  Gly Asp Ser Ser Arg  Tyr Ser Ala
    1010             1015                 1020

Tyr His  Gln Gly Arg His Ser  Glu Ser Val His Glu  Arg Ser Ala
    1025             1030                 1035

Ser Arg  Thr Gly Gln Arg Gln  Gly Ser His His Glu  Gln Ser Arg
    1040             1045                 1050

Asp Ser  Ser Arg Gln Ser Gly  Thr Gly His Gly His  Ala Ser Ala
    1055             1060                 1065

Gly Ser  Gly Ile Asn Arg His  Arg Glu Ser Ser Val  Ser Gln Ala
    1070             1075                 1080

Ser Asp  Arg Glu Gly His Ala  Arg Asp Ser Gly Arg  Gln Ser Val
    1085             1090                 1095

Thr Thr  His Gly Arg Pro Gly  Ser Ser Ser Arg Asn  Gln His Val
    1100             1105                 1110

Ser Ser  His Gly Gln Ile Gly  Asp Ser Ser His  Ser Glu Thr
    1115             1120                 1125

Asn Gln  Gly Ser His Asn Glu  Arg His Thr Arg Asp  Ser Gly Arg
    1130             1135                 1140

His Ser  Glu Thr Thr His Gly  Arg Leu Gly Ser Ser  Ser Arg Asn
    1145             1150                 1155

Gln His  Gly Ser Val His Gly  Gln Thr Arg Asp Ser  Pro Arg His
    1160             1165                 1170

Ser Glu  Ser His Gln Glu Arg  His Ser Glu Ser Val  His Glu Arg
    1175             1180                 1185

Ser Gly  Ser Ser Thr Gly Gln  Arg Gln Gly Ser His  His Glu Gln
    1190             1195                 1200

Ser Arg  Asp Ser Ser Arg His  Ser Gly Thr Arg His  Gly Gln Thr
    1205             1210                 1215

Ser Thr  Val Ser Gly Gly Ser  Arg His Arg Glu Pro  Ser Val Ser
    1220             1225                 1230

Gln Ala  Ser Asp Ser Glu Gly  His Ser Glu Asp Ser  Gly Arg Gln
    1235             1240                 1245

Ser Val  Thr Thr His Gly Arg  Pro Gly Ser Thr Ser  Arg Asn Gln
    1250             1255                 1260

His Gly  Ser Val His Gly Gln  Thr Arg Asp Ser Pro  Arg His Ser
    1265             1270                 1275

Glu Ser  His Gln Glu Arg His  Ser Glu Ser Val His  Gln Arg Ser
    1280             1285                 1290

Gly Ser  Ser Thr Gly Gln Arg  Gln Gly Ser His His  Glu Gln Ser
    1295             1300                 1305

Arg Asp  Ser Ser Arg His Ser  Gly Thr Gly His Gly  Gln Thr Ser
    1310             1315                 1320

Ala Gly  Ser Gly Ser Ser Arg  His Arg Glu Ser Ser  Val Ser Gln
    1325             1330                 1335

Ala Ser  Asp Ser Glu Gly His  Ser Glu Asp Ser Gly  Arg Gln Asn
    1340             1345                 1350

Val Thr  Thr His Gly Arg Pro  Gly Ser Ser Ser Arg  Asn Gln His
    1355             1360                 1365

Gly Ser  Ser Gln Gly Gln Thr  Gly Asp Ser Ser Arg  Tyr Ser Ala
    1370             1375                 1380
```

```
Ser His Gln Gly Arg His Ser Glu Ser Val His Glu Arg Ser Thr
    1385                1390                1395

Ser Arg Thr Gly Gln Arg Gln Gly Ser His His Glu Gln Ser Arg
    1400                1405                1410

Asp Ser Ser Arg Gln Ser Gly Thr Gly His Gly His Ala Ser Ala
    1415                1420                1425

Gly Ser Gly Ile Asn Arg His Arg Glu Ser Ser Val Ser Gln Ala
    1430                1435                1440

Ser Asp Ser Glu Gly His Ser Glu Asp Ser Gly Arg Gln Asn Val
    1445                1450                1455

Thr Thr His Gly Arg Pro Gly Ser Ser Ser Ser Asn Gln His Gly
    1460                1465                1470

Ser Ser His Gly Gln Thr Gly Asp Ser Ser Arg His Ser Glu Ser
    1475                1480                1485

His Gln Gly Ser His Gly Glu Ser Val His Gln Arg Ser Gly Ser
    1490                1495                1500

Ser Thr Gly Gln Arg Gln Gly Ser His His Glu Gln Ser Arg Asp
    1505                1510                1515

Ser Ser Arg His Ser Gly Thr Gly His Gly Glu Thr Ser Thr Gly
    1520                1525                1530

Ser Gly Ser Ser Arg His Arg Glu Ser Ser Val Ser Gln Ser Ser
    1535                1540                1545

Asp Ser Lys Gly His Ser Arg Gly Ser Gly Asn Gln Thr Val Thr
    1550                1555                1560

Asn Gln Arg Met Ser Ala Phe Tyr Ser Arg Phe Gln Asn His Gly
    1565                1570                1575

Ala Gly Gln Val Trp Arg His Gly Ser Tyr Gly Ser Ser Asn Tyr
    1580                1585                1590

Asp Tyr Gly Gln Leu Gly Thr Gly His Ser Pro Asp Glu Asn Phe
    1595                1600                1605

Ser His Asp Ser Ser His Val Glu Lys Arg Asp Lys Pro Glu Tyr
    1610                1615                1620

Arg Gly Glu Leu Met Arg Ser Asn Ile Thr Val Arg Asn Ile His
    1625                1630                1635

Pro Gly Thr Tyr Gly His Ser Asn Tyr Ile Ser Lys Gln Leu Gly
    1640                1645                1650

Phe Gly Gln
    1655

<210> SEQ ID NO 18
<211> LENGTH: 1183
<212> TYPE: PRT
<213> ORGANISM: Macaca mulatta

<400> SEQUENCE: 18

Met Ser Thr Leu Leu Glu Asn Ile Phe Ala Ile Ile Asn Leu Phe Lys
1               5                   10                  15

Gln Tyr Ser Lys Lys Asp Lys Asn Thr Asp Thr Leu Ser Lys Lys Glu
                20                  25                  30

Leu Lys Glu Leu Leu Glu Lys Glu Phe Arg Pro Ile Leu Lys Asn Pro
            35                  40                  45

Asp Asp Pro Asp Thr Val Glu Val Phe Met Asp His Leu Asp Ile Asp
        50                  55                  60

His Asn Lys Lys Ile Asp Phe Thr Glu Phe Leu Leu Met Val Phe Lys
65                  70                  75                  80
```

```
Leu Ala Gln Ala Tyr Tyr Glu Ser Thr Arg Lys Gln Asn Leu Pro Ile
                85                  90                  95
Ala Gly His Lys His Arg Lys His Ser His His Asp Lys His Glu Asp
            100                 105                 110
Asn Lys Glu Glu Glu Asn Lys Glu Lys Arg Lys Arg Pro Leu Ser Leu
            115                 120                 125
Glu Arg Arg Asn Asn Arg Lys Gly Asn Thr Gly Arg Ser Lys Ser Pro
    130                 135                 140
Arg Glu Arg Gly Gly Lys Arg His Glu Ser Ser Phe Glu Lys Lys Glu
145                 150                 155                 160
Arg Lys Gly Tyr Ser Pro Thr Tyr Glu Glu Glu Tyr Gly Gln Asn
                165                 170                 175
His His Lys Ser Ser Lys Lys Glu Lys Asn Lys Thr Glu Ile Thr Arg
            180                 185                 190
Leu Glu His Glu Gly Lys Arg Ile Ser Glu Arg Pro Glu Lys Lys Glu
            195                 200                 205
Glu Lys Glu Asp Gly Gln Phe Asp Tyr Glu Asn Ala Gly Arg Met Asp
    210                 215                 220
Glu Lys Trp Thr Glu Ser Gly His Ile Ala Ile Tyr His Ala Ile Gln
225                 230                 235                 240
Asp Glu Val Asp Thr Thr Glu Asn Ile Leu Glu Glu Asn Arg Arg
                245                 250                 255
Tyr Glu Thr Ser Arg Ser Pro His Asp Lys Ser Ser Leu Arg Val Asn
                260                 265                 270
Arg Ser Pro Asn Ala Asn Thr Ser Gln Ile Pro Leu Val Glu Pro Arg
            275                 280                 285
Arg Arg Thr Arg Gln Arg Ser Ser Val Ser Gln Asp Ser Asp Ser Glu
    290                 295                 300
Gly His Ser Glu Asp Ser Glu Arg Gln Ser Glu Ser Ala Ser Arg Asn
305                 310                 315                 320
His His Gly Ser Val Arg Glu Gln Ser Arg His Gly Ser Arg His Pro
                325                 330                 335
Gly Ser His His Glu Asp Arg Ala Gly His Gly His Ser Ala Asp Ser
            340                 345                 350
Ser Thr Gln Ser Gly Thr Arg His Thr Glu Thr Ser Ser Arg Gly Gln
            355                 360                 365
Ala Val Ser Ser His Glu Gln Ala Arg Ser Ser Pro Gly Glu Arg His
    370                 375                 380
Gly Ser Arg His Gln Gln Ser Ala Glu Ser Ser Arg His Ser Gly Ile
385                 390                 395                 400
Gly Arg Gly Gln Ala Ser Ser Ala Val Ser Asp Arg Gly His Gln Gly
                405                 410                 415
Pro Ser Gly Ser His Phe Ser Asp Ser Glu Gly His Ser Glu His Ser
            420                 425                 430
Asp Thr Gln Ser Val Ser Gly His Gly Gln Ala Gly Pro His Pro His
            435                 440                 445
Ser His Gln Glu Ser Ala Arg Gly Arg Ser Arg Glu Arg Ser Gly Arg
    450                 455                 460
Ser Gly Ser Phe Leu Tyr Gln Val Ser Thr His Glu Gln Ser Glu Ser
465                 470                 475                 480
Thr His Gly Arg Thr Gly Pro Ser Ser Ala Gly Arg Gln Gly Ser Arg
                485                 490                 495
```

```
Asn Glu Gln Ala Arg Asp Ser Ser Arg His Ser Ala Ser His Glu Val
                500                 505                 510

Gln Asp Thr Val His Gly His His Gly Ser Ser Arg Gly Arg Gln
            515                 520                 525

Gly Ser His His Glu Gln Leu Val Asp Ser Ser Gly His Ser Gly Ser
        530                 535                 540

His His Ser His Thr Thr Ser Gln Gly Arg Ser Asp Ala Ser Arg Gly
545                 550                 555                 560

Glu Ser Gly Ala Arg Ser Ala Ser Arg Gln Thr Arg His Glu Glu Gln
                565                 570                 575

Ser Gly Asp Gly Ser Arg His Ser Gly Ser Arg His His Glu Ser Ser
            580                 585                 590

Asn Arg Ala Asp Ser Ser Arg His Ala Gln Ser Ser Gln Gly Gln Ser
        595                 600                 605

Ala Gly Phe Arg Thr Ser Thr Arg Arg Gly Ser Ser Val Ser Gln Asp
    610                 615                 620

Ser Asp Ser Glu Gly His Ser Glu Asp Ser Glu Arg Gln Ser Glu Ser
625                 630                 635                 640

Ala Ser Arg Asn His His Gly Ser Val Arg Glu Gln Ser Arg His Gly
                645                 650                 655

Ser Gly His Ser Gly Ser His His Gln Asp Lys Val Gly His Arg Tyr
            660                 665                 670

Ser Gly Asp Ser Ser Arg Gln Ser Gly Thr His His Val Glu Thr Ser
        675                 680                 685

Ser His Gly Gln Ala Ala Ser Ser His Glu Gln Thr Arg Ser Ser Pro
    690                 695                 700

Gly Glu Arg His Gly Ser His His Gln Gln Ser Ala Asp Ser Ser Arg
705                 710                 715                 720

His Ser Gly Thr Gly Arg Gly Gln Ala Ser Ser Ala Val Ser Asp Arg
                725                 730                 735

Gly His Gln Gly Pro Ser Gly Ser His Phe Ser Asp Ser Glu Gly His
            740                 745                 750

Ser Glu His Ser Asp Thr Gln Ser Val Ser Gly Gln Gly Gln Ala Gly
        755                 760                 765

Arg His Pro His Ser His Gln Glu Ser Ala Arg Gly Arg Ser Gly Glu
    770                 775                 780

Arg Ser Gly Arg Ser Gly Ser Phe Val Tyr Gln Val Ser Thr His Glu
785                 790                 795                 800

Gln Ser Glu Ser Thr His Gly Arg Thr Gly Pro Ser Thr Gly Gly Arg
                805                 810                 815

Gln Gly Ser Arg Asn Glu Gln Ala Arg Asp Ser Ser Arg His Ser Val
            820                 825                 830

Ser His Glu Gly Gln Asp Thr Ile His Gly His His Gly Ser Ser Arg
        835                 840                 845

Gly Gly Arg Gln Gly Ser His His Glu Gln Ser Val Asp Ser Ser Gly
    850                 855                 860

His Ser Gly Ser His His Ser His Thr Thr Ser Gln Gly Arg Ser Asp
865                 870                 875                 880

Ala Ser Arg Gly Glu Ser Gly Ala Arg Ser Ala Ser Arg Gln Thr Arg
                885                 890                 895

His Glu Glu Gln Ser Gly Asp Gly Ser Arg His Ser Gly Ser Arg His
            900                 905                 910

His Glu Ala Ser Asn Arg Ala Asp Ser Ser Arg His Ala Gln Ser Gly
```

```
                    915                 920                 925
Gln Gly Gln Ser Ala Gly Phe Arg Thr Ser Thr Arg Arg Gly Ser Ser
    930                 935                 940
Val Ser Gln Asp Ser Asp Ser Glu Gly His Ser Glu Asp Ser Glu Arg
945                 950                 955                 960
Gln Ser Glu Ser Ala Ser Arg Asn His His Gly Ser Val Arg Glu Gln
                965                 970                 975
Ser Arg His Gly Ser Arg His Pro Gly Ser His His Glu Asp Arg Ala
            980                 985                 990
Gly His Gly His Ser Ala Asp Ser Ser Arg Gln Ser Gly Thr Arg His
        995                 1000                1005
Thr Glu Thr Ser Ser Arg Gly Gln Ala Val Ser Ser His Glu Gln
    1010                1015                1020
Ala Arg Ser Ser Pro Gly Glu Arg His Gly Ser Arg His Gln Gln
    1025                1030                1035
Ser Ala Glu Ser Ser Arg His Ser Gly Ile Gly Arg Gly Gln Ala
    1040                1045                1050
Ser Ser Ala Val Ser Asp Arg Gly His Gln Gly Pro Ser Gly Ser
    1055                1060                1065
His Phe Ser Asp Ser Glu Gly His Ser Glu His Ser Asp Thr Gln
    1070                1075                1080
Ser Val Ser Gly His Gly Gln Ala Gly Pro His Pro His Ser His
    1085                1090                1095
Gln Glu Ser Ala Arg Gly Arg Ser Gly Glu Arg Ser Gly Arg Ser
    1100                1105                1110
Gly Ser Phe Leu Tyr Gln Val Ser Thr His Glu Gln Ser Glu Ser
    1115                1120                1125
Thr His Gly Arg Thr Gly Pro Ser Ser Ala Gly Arg Gln Gly Ser
    1130                1135                1140
Arg Asn Glu Gln Ala Arg Asp Ser Ser Arg His Ser Ala Ser His
    1145                1150                1155
Glu Val Gln Asp Thr Val His Gly His His Gly Ser Ser Arg Gly
    1160                1165                1170
Gly Arg Gln Gly Ser His His Glu Gln Ser
    1175                1180

<210> SEQ ID NO 19
<211> LENGTH: 2265
<212> TYPE: PRT
<213> ORGANISM: Macaca mulatta

<400> SEQUENCE: 19

Met Thr Asp Leu Leu Arg Ser Val Val Thr Val Ile Asp Val Phe Tyr
1               5                   10                  15

Lys Tyr Thr Lys Gln Asp Gly Glu Cys Gly Thr Leu Ser Lys Asp Glu
                20                  25                  30

Leu Lys Glu Leu Leu Glu Lys Glu Phe His Pro Val Leu Lys Asn Pro
            35                  40                  45

Asp Asp Pro Asp Thr Val Asp Val Ile Met His Met Leu Asp Arg Asp
50                  55                  60

His Asp Arg Arg Leu Asp Phe Thr Glu Phe Leu Leu Met Ile Phe Lys
65                  70                  75                  80

Leu Thr Met Ala Cys Asn Lys Val Leu Ser Lys Glu Tyr Cys Lys Ala
                85                  90                  95
```

```
Ser Gly Ser Lys Lys His Arg Arg Gly His Arg His Gln Glu Glu
            100                 105                 110
Ser Glu Thr Glu Glu Asp Glu Glu Asp Thr Pro Glu His Lys Ser Gly
            115                 120                 125
Tyr Arg His Ser Ser Trp Ser Glu Gly Glu Glu His Gly Tyr Ser Ser
        130                 135                 140
Gly His Ser Arg Gly Thr Val Lys Arg His Gly Ser Asn Ser Arg
145                 150                 155                 160
Arg Leu Gly Arg Gln Gly His Leu Ser Ser Gly Asn Gln Glu Arg
                165                 170                 175
Ser Gln Lys Arg Tyr His Arg Ser Ser Gly His Ser Trp Ser Ser
            180                 185                 190
Gly Lys Glu Arg His Gly Phe Ser Ser Gly Leu Arg Glu Arg Ile
            195                 200                 205
Asn Lys Ser His Val Ser Pro Ser Arg Glu Phe Gly Glu Glu Tyr Glu
        210                 215                 220
Ser Gly Ser Gly Ser Lys Ser Trp Glu Arg Lys Gly His Gly Gly Leu
225                 230                 235                 240
Ser Cys Gly Leu Glu Ile Ser Gly His Glu Ser Asn Ser Thr Gln Ser
                245                 250                 255
Arg Ser Ser Gly Gln Lys Leu Gly Ser Ser Arg Ser Cys Ser Gly Asp
            260                 265                 270
Ser Arg Arg Arg Ser His Ala Cys Gly Tyr Ser Asn Ser Ser Gly Cys
            275                 280                 285
Gly Arg Pro Gln Asn Ala Ser Asn Ser Cys Gln Ser His Arg Phe Gly
290                 295                 300
Gly Gln Val Asn Gln Ser Ser Tyr Ile Gln Ser Gly Cys Gln Ser Gly
305                 310                 315                 320
Ile Asn Gly Glu Gln Gly His Asp Cys Val Ser Gly Gly Gln Pro Ser
            325                 330                 335
Gly Cys Gly Gln Pro Glu Ser Asn Ser Cys Ser Gln Ser Tyr Ser Gln
            340                 345                 350
Arg Gly Tyr Gly Ala Arg Glu Asn Gly Gln Pro Gln Asn Cys Gly Gly
            355                 360                 365
Gln Gln Arg Thr Gly Ser Ser Gln Ser Ser Phe Cys Gly Gln Tyr Glu
        370                 375                 380
Ser Gly Gly Ser Gln Ser Cys Ser Asn Gly Gln His Glu His Gly Ser
385                 390                 395                 400
Cys Gly Arg Phe Ser Asn Ser Ser Ser Asn Glu Phe Ser Lys Cys
            405                 410                 415
Gly Lys His Arg Ser Gly Ser Gly Gln Phe Thr Ser Cys Glu Gln His
            420                 425                 430
Gly Thr Gly Leu Ser Gln Ser Ser Gly Phe Glu Gln Gln Val Ala Gly
            435                 440                 445
Ser Ser Gln Thr Cys Ser Gln Tyr Gly Ser Arg Ser Ser Gln Ser Ser
            450                 455                 460
Gly Tyr Asp Glu His Gly Ser Ser Ser Gly Lys Thr Ser Gly Phe Gly
465                 470                 475                 480
Gln His Arg Ser Gly Ser His Ser Gly Phe Gly Gln His Gly
                485                 490                 495
Ser Gly Ser Gly Gln Ser Phe Gly Phe Gly Gln His Gly Ser Gly Ser
            500                 505                 510
Gly Gln Ser Ser Gly Phe Gly Gln His Glu Ser Arg Ser Cys Gln Ser
```

-continued

```
                515                 520                 525
Ser Tyr Gly Gln His Gly Ser Gly Ser Ser Gln Ser Ser Gly Tyr Gly
530                 535                 540

Gln His Ala Ser Arg Gln Thr Ser Gly Phe Gly Gln His Gly Leu Gly
545                 550                 555                 560

Ser Gly Gln Ser Thr Gly Phe Gly Gln Tyr Gly Ser Ser Gly Gln
                565                 570                 575

Ser Ser Gly Phe Gly Gln His Gly Ser Gly Ser Gln Ser Ser Gly
                580                 585                 590

Phe Gly Gln His Glu Ser Arg Ser Gly Gln Ser Ser Tyr Gly Gln His
                595                 600                 605

Ser Ser Ser Ser Gln Ser Ser Gly Tyr Gly Gln His Gly Ser Arg
610                 615                 620

Gln Thr Ser Gly Phe Gly Gln His Gly Ser Gly Ser Gln Ser Thr
625                 630                 635                 640

Gly Phe Gly Gln Tyr Gly Ser Ser Leu Gly Gln Ser Ser Gly Phe Gly
                645                 650                 655

Gln His Gly Ser Gly Ser Gly Gln Ser Ser Gly Phe Gly Gln His Glu
                660                 665                 670

Ser Thr Ser Gly Gln Ser Ser Tyr Gly Gln His Gly Phe Gly Ser Ser
                675                 680                 685

Gln Ser Ser Gly Cys Gly Gln His Gly Leu Ser Ser Gly Gln Thr Ser
690                 695                 700

Gly Phe Gly Gln His Glu Leu Ser Ser Gly Gln Ser Ser Phe Gly
705                 710                 715                 720

Gln His Gly Ser Gly Ser Gly Gln Ser Ser Gly Phe Arg Gln His Glu
                725                 730                 735

Ser Gly Ser Gly Gln Ser Ser Gly Phe Gly Gln His Glu Ser Arg Ser
                740                 745                 750

His Gln Ser Ser Tyr Gly Pro His Gly Ser Gly Ser Gly Gln Ser Ser
                755                 760                 765

Gly Tyr Gly Gln His Gly Ser Ser Ser Gly Gln Thr Ser Gly Phe Gly
                770                 775                 780

Gln Gln Gly Ser Ser Ser Gln Tyr Ser Gly Phe Gly Gln His Gly
785                 790                 795                 800

Ser Gly Leu Gly Gln Ser Ser Gly Phe Gly Gln His Gly Thr Gly Ser
                805                 810                 815

Gly Gln Phe Ser Gly Phe Gly Gln His Glu Ser Arg Ser His Gln Ser
                820                 825                 830

Ser Tyr Gly Gln His Gly Ser Gly Ser Ser Gln Ser Ser Gly Tyr Gly
                835                 840                 845

Gln His Gly Ser Ser Ser Gly His Thr Thr Gly Phe Gly Gln His Arg
                850                 855                 860

Ser Ser Ser Gly Gln Tyr Ser Gly Phe Gly Gln His Gly Ser Gly Leu
865                 870                 875                 880

Gly Gln Ser Ser Gly Phe Gly Gln His Gly Thr Gly Ser Gly Gln Ser
                885                 890                 895

Ser Gly Phe Gly Gln His Glu Ser Arg Ser His Gln Ser Ser Tyr Gly
                900                 905                 910

Gln His Gly Ser Gly Ser Ser Gln Ser Ser Tyr Gly Gln His Gly
                915                 920                 925

Ser Ser Ser Gly Gln Thr Ser Gly Phe Gly Gln His Arg Ser Gly Ser
930                 935                 940
```

```
Gly Gln Ser Ser Gly Phe Gln Tyr Gly Leu Gly Ser Gly Gln Ser
945                 950                 955                 960

Ser Gly Phe Gly Gln His Gly Ser Gly Thr Gly Gln Ser Ser Gly Phe
            965                 970                 975

Ala Arg His Glu Tyr Arg Ser Gly Gln Ser Ser Tyr Gly Gln His Gly
                980                 985                 990

Thr Gly Ser Ser Gln Ser Ser Gly Cys Gly Gln Arg Glu Ser Gly Ser
            995                 1000                1005

Gly Pro Thr Thr Gly Phe Gly Gln His Val Ser Gly Ser Asp Asn
        1010                1015                1020

Phe Ser Ser Ser Gly Gln His Ile Ser Gly Ser Asp Gln Ser Thr
        1025                1030                1035

Gly Phe Gly Gln Tyr Gly Ser Gly Ser Gly Gln Ser Thr Gly Leu
        1040                1045                1050

Gly Gln Val Glu Ser Gln Gln Val Ala Ser Gly Ser Thr Val His
        1055                1060                1065

Gly Arg Gln Glu Thr Thr His Gly Gln Thr Ile Asn Thr Ala Arg
        1070                1075                1080

His Ser Gln Ser Gly Gln Gly Gln Ser Thr Gln Thr Gly Ser Arg
        1085                1090                1095

Val Ser Arg Arg Arg Arg Ser Ser Gln Ser Glu Asn Ile Asp Ser
        1100                1105                1110

Glu Val His Ser Arg Val Ser His Arg His Ser Glu His Ile Asp
        1115                1120                1125

Thr Gln Val Gly Ser His Tyr Pro Glu Ser Gly Ser Thr Val His
        1130                1135                1140

Arg Arg Gln Gly Thr Thr His Gly Gln Arg Gly Asp Thr Thr Arg
        1145                1150                1155

His Ser His Ser Gly His Gly Gln Ser Thr Gln Thr Gly Ser Arg
        1160                1165                1170

Thr Thr Gly Arg Gln Arg Phe Ser His Ser Asp Ala Thr Asp Ser
        1175                1180                1185

Glu Val His Ser Gly Val Ser His Arg Pro His Ser Gln Glu His
        1190                1195                1200

Thr His Gly Gln Asp Gly Ser Gln Leu Gly Glu Ser Gln Ser Thr
        1205                1210                1215

Val His Glu Arg His Glu Thr Thr Tyr Gly Gln Thr Gly Asp Ala
        1220                1225                1230

Thr Gly His Gly Tyr Ser Gly His Gly Gln Ser Thr Gln Ile Gly
        1235                1240                1245

Ser Arg Thr Ser Gly Arg Arg Gly Ser Gly His Ser Glu Ser Ser
        1250                1255                1260

Asp Thr Glu Val His Ser Gly Ser His Arg Pro His Ser Gln
        1265                1270                1275

Glu Gln Thr His Gly Gln Ala Arg Ser Gln His Gly Glu Ser Arg
        1280                1285                1290

Ser Thr Val His Glu Arg His Gly Thr Thr His Gly Gln Thr Gly
        1295                1300                1305

Asp Thr Thr Arg Tyr Ala His Tyr His Asn Gly Gln Ser Ala Gln
        1310                1315                1320

Arg Gly Ser Arg Thr Thr Gly Arg Gly Ser Gly His Ser Glu Tyr
        1325                1330                1335
```

```
Ser Asp Ser Glu Leu Tyr Ser Gly Gly Ser His Thr Tyr Ser Gly
    1340                1345                1350

His Thr His Gly Gln Ala Gly Ser Gln His Gly Glu Ser Asp Ser
    1355                1360                1365

Ile Val His Glu Arg Tyr Gly Thr Thr His Gly Gln Thr Gly Asp
    1370                1375                1380

Thr Thr Arg His Ala His Tyr Ser His Gly Gln Ser Lys Gln Arg
    1385                1390                1395

Gly Ser Arg Thr Thr Gly Arg Arg Gly Ser Gly His Ser Glu Tyr
    1400                1405                1410

Ser Asp Ser Glu Gly His Ser Gly Gly Ser His Thr His Ser Gly
    1415                1420                1425

His Thr His Gly His Thr His Gly Gln Ala Gly Ser Gln His Gly
    1430                1435                1440

Glu Ser Gly Ser Ser Gly His Gly Gly Gln Gly Thr Thr His Gly
    1445                1450                1455

Gln Thr Gly Asp Thr Thr Arg His Ala His Tyr Gly His Gly Gln
    1460                1465                1470

Ser Thr Gln Arg Gly Ser Arg Thr Ala Gly Arg Arg Gly Ser Gly
    1475                1480                1485

His Ser Glu Tyr Ser Asp Ser Glu Gly His Ser Gly Val Ser His
    1490                1495                1500

Thr His Ser Gly His Thr His Gly Gln Ala Gly Ser Gln His Gly
    1505                1510                1515

Glu Ser Glu Ser Thr Val His Glu Arg Gln Gln Thr Thr His Gly
    1520                1525                1530

Gln Thr Gly Asp Thr Thr Arg His Ala His Tyr Gly His Gly Gln
    1535                1540                1545

Ser Thr Gln Thr Gly Ser Arg Thr Thr Gly Arg Arg Gly Ser Gly
    1550                1555                1560

His Ser Glu Tyr Ser Asp Ser Glu Gly His Ser Gly Val Ser His
    1565                1570                1575

Thr His Ser Gly His Thr His Gly Gln Ala Arg Ser Gln His Gly
    1580                1585                1590

Glu Ser Gly Ser Ala Ile His Gly Arg Gln Gly Thr Ile His Gly
    1595                1600                1605

Gln Thr Gly Asp Thr Thr Arg His Gly Gln Ser Gly His Gly Gln
    1610                1615                1620

Ser Thr Gln Thr Gly Ser Arg Thr Thr Gly Arg Arg Gly Ser Gly
    1625                1630                1635

His Ser Glu Tyr Ser Asp Ser Glu Gly His Ser Gly Gly Ser His
    1640                1645                1650

Thr His Ser Gly His Thr His Gly Gln Ala Gly Ser Gln His Gly
    1655                1660                1665

Glu Ser Gly Ser Thr Val His Gly Arg Gln Gly Thr Ile His Gly
    1670                1675                1680

Gln Thr Gly Asp Thr Thr Arg His Gly Gln Ser Gly His Gly Gln
    1685                1690                1695

Ser Ile Glu Thr Gly Ser Arg Thr Thr Gly Arg Arg Gly Ser Gly
    1700                1705                1710

His Ser Glu Tyr Ser Asp Ser Glu Gly His Ser Gly Val Ser His
    1715                1720                1725

Thr His Ser Gly His Thr His Gly Gln Ala Gly Ser Gln His Gly
```

-continued

```
                1730                1735                1740
Glu Ser Glu Ser Thr Val His Glu Arg Gln Gln Thr Thr His Gly
    1745                1750                1755
Gln Thr Gly Asp Ile Thr Glu His Gly His Ser Ser His Gly Gln
    1760                1765                1770
Thr Thr Gln Thr Gly Ser Arg Thr Thr Gly Arg Arg Gly Ser Gly
    1775                1780                1785
His Ser Glu Tyr Ser Asp Ser Glu Trp His Ser Gly Gly Ser His
    1790                1795                1800
Thr His Ser Gly His Thr His Gly Gln Ala Gly Phe Gln His Gly
    1805                1810                1815
Glu Ser Gly Ser Ala Val His Gly Arg Gln Gly Thr Ile His Gly
    1820                1825                1830
Gln Thr Gly Asp Thr Thr Arg His Gly Gln Ser Gly His Gly Glu
    1835                1840                1845
Ser Ile Gln Thr Gly Ser Arg Thr Ile Gly Arg Arg Gly Ser Gly
    1850                1855                1860
His Ser Glu Tyr Ser Asp Ser Glu Gly His Ser Gly Ile Ser His
    1865                1870                1875
Thr His Ser Gly His Thr His Gly Gln Ala Gly Ser Gln His Gly
    1880                1885                1890
Glu Ser Gly Ser Ser Gly His Gly Arg Gln Gly Thr Ala His Gly
    1895                1900                1905
Gln Thr Gly Asp Thr Thr Arg His Ala His Tyr Asp His Gly Gln
    1910                1915                1920
Ser Thr Gln Arg Gly Ser Arg Thr Ala Gly Arg Arg Gly Ser Gly
    1925                1930                1935
His Ser Glu Tyr Ser Asp Ser Glu Gly His Ser Gly Val Ser His
    1940                1945                1950
Thr His Ser Gly His Thr His Gly Gln Ala Gly Ser Gln His Gly
    1955                1960                1965
Glu Ser Gly Ala Ala Val His Gly Arg Gln Gly Ile Ile His Gly
    1970                1975                1980
Gln Thr Gly Asp Thr Thr Arg His Gly Gln Ser Gly Gln Gly Gln
    1985                1990                1995
Ser Thr Gln Arg Gly Ser Arg Thr Thr Gly Arg Arg Gly Ser Gly
    2000                2005                2010
His Ser Glu Tyr Ser Asp Ser Val Gly His Ser Gly Val Ser His
    2015                2020                2025
Thr His Ser Gly His Thr His Gly Leu Ala Gly Ser Gln His Gly
    2030                2035                2040
Glu Ser Gly Ser Ser Gly His Gly Arg Gln Gly Thr Leu His Gly
    2045                2050                2055
Gln Thr Gly Asp Thr Thr Arg His Ala His Tyr Gly His Gly Gln
    2060                2065                2070
Ser Thr Gln Arg Gly Ser Arg Thr Ala Gly Arg Arg Gly Ser Gly
    2075                2080                2085
His Ser Glu Tyr Ser Asp Ser Glu Trp His Ser Gly Gly Ser His
    2090                2095                2100
Thr His Ser Gly His Thr His Gly Gln Ala Gly Ser Gln His Gly
    2105                2110                2115
Glu Ser Gly Ser Ala Val His Gly Arg Gln Gly Thr Ile His Gly
    2120                2125                2130
```

```
Gln Thr Gly Asp Thr Thr Arg His Gly Gln Ser Gly His Gly Gln
    2135                2140                2145

Ser Thr Gln Ile Gly Pro His Ser Ser Ser Ser Tyr Asn Tyr His
    2150                2155                2160

Ser Glu Gly Thr Glu Arg Glu Arg Gly Gln Ser Gly Leu Val Trp
    2165                2170                2175

Arg His Gly Ser Tyr Gly Ser Ala Asp Tyr Asp Tyr Gly Glu Ser
    2180                2185                2190

Arg Phe Arg His Ser Gln His Gly Ser Val Ser Tyr Asn Ser Asn
    2195                2200                2205

Pro Val Val Phe Lys Glu Arg Ser Asp Ile Arg Lys Ala Ser Ala
    2210                2215                2220

Phe Gly Glu Asp His Pro Arg Tyr Tyr Ala Arg Tyr Val Asn Arg
    2225                2230                2235

Gln Pro Gly Leu Tyr Arg His Ser Ser Asp Ile Ser Lys Gln Leu
    2240                2245                2250

Gly Phe Ser Gln Ser Gln Arg Tyr Tyr Tyr Tyr Glu
    2255                2260                2265

<210> SEQ ID NO 20
<211> LENGTH: 10
<212> TYPE: PRT
<213> ORGANISM: Artificial Sequence
<220> FEATURE:
<223> OTHER INFORMATION: Synthetic peptide

<400> SEQUENCE: 20

Arg Met Arg Arg Met Arg Arg Met Arg Arg
1               5                   10

<210> SEQ ID NO 21
<211> LENGTH: 354
<212> TYPE: PRT
<213> ORGANISM: Artificial Sequence
<220> FEATURE:
<223> OTHER INFORMATION: Synthetic peptide

<400> SEQUENCE: 21

Arg Ser Gly Glu Thr Ser Gly Arg Ser Gly Ser Phe Leu Tyr Gln Val
1               5                   10                  15

Ser Thr His Glu Gln Ser Glu Ser Thr His Gly Gln Thr Ala Pro Ser
                20                  25                  30

Thr Gly Gly Arg Gln Gly Ser Arg His Glu Gln Ala Arg Asn Ser Ser
            35                  40                  45

Arg His Ser Ala Ser Gln Asp Gly Gln Asp Thr Ile Arg Gly His Pro
        50                  55                  60

Gly Ser Ser Arg Gly Gly Arg Gln Gly Ser Tyr His Glu Gln Ser Val
65                  70                  75                  80

Asp Arg Ser Gly His Ser Gly Tyr His His Ser His Thr Thr Pro Gln
                85                  90                  95

Gly Arg Ser Asp Ala Ser His Gly Gln Ser Gly Pro Arg Ser Ala Ser
            100                 105                 110

Arg Gln Thr Arg Asn Glu Glu Gln Ser Gly Asp Gly Ser Arg His Ser
        115                 120                 125

Gly Ser Arg His His Glu Pro Ser Thr Arg Ala Gly Ser Ser Arg His
    130                 135                 140

Ser Gln Val Gly Gln Gly Glu Ser Ala Gly Ser Lys Thr Ser Arg Arg
```

```
            145                 150                 155                 160
Gln Gly Ser Ser Val Ser Gln Asp Arg Asp Ser Glu Gly His Ser Glu
                165                 170                 175
Asp Ser Glu Arg Arg Ser Glu Ser Ala Ser Arg Asn His Tyr Gly Ser
            180                 185                 190
Ala Arg Glu Gln Ser Arg His Gly Ser Arg Asn Pro Arg Ser His Gln
        195                 200                 205
Glu Asp Arg Ala Ser His Gly His Ser Ala Glu Ser Ser Arg Gln Ser
    210                 215                 220
Gly Thr Arg His Ala Glu Thr Ser Ser Gly Gly Gln Ala Ala Ser Ser
225                 230                 235                 240
Gln Glu Gln Ala Arg Ser Ser Pro Gly Glu Arg His Gly Ser Arg His
                245                 250                 255
Gln Gln Ser Ala Asp Ser Ser Thr Asp Ser Gly Thr Gly Arg Arg Gln
            260                 265                 270
Asp Ser Ser Val Val Gly Asp Ser Gly Asn Arg Gly Ser Ser Gly Ser
        275                 280                 285
Gln Ala Ser Asp Ser Glu Gly His Ser Glu Glu Ser Asp Thr Gln Ser
    290                 295                 300
Val Ser Ala His Gly Gln Ala Gly Pro His Gln Gln Ser His Gln Glu
305                 310                 315                 320
Ser Thr Arg Gly Gln Ser Gly Glu Arg Ser Gly Arg Ser Gly Ser Phe
                325                 330                 335
Tyr Gln Val Ser Thr His Glu Gln Arg Met Arg Arg Met Arg Arg Met
            340                 345                 350
Arg Arg

<210> SEQ ID NO 22
<211> LENGTH: 279
<212> TYPE: PRT
<213> ORGANISM: Artificial Sequence
<220> FEATURE:
<223> OTHER INFORMATION: Synthetic peptide

<400> SEQUENCE: 22

Gly Ser Gly Phe Tyr Pro Val Tyr Tyr Tyr Glu Gln Glu His Ser
1               5                   10                  15
Glu Glu Glu Ser Asp Ser Gln His Gly His Gln His Glu Gln Gln Arg
                20                  25                  30
Gly His Gln His Gln His Gln His Glu His Glu Gln Pro Glu Ser Gly
            35                  40                  45
His Arg Gln Gln Gln Ser Ser Gly Arg Gly His Gln Gly Ala His Gln
        50                  55                  60
Glu Gln Gly Arg Asp Ser Ala Arg Ser Arg Ser Asn Gln Gly His
65                  70                  75                  80
Ser Ser Ser Arg His Gln Ala Asp Ser Pro Arg Val Ser Ala Arg Ser
                85                  90                  95
Gly Ser Gly Gly Arg Gly Gln Ser Pro Asp Ala Ser Gly Arg Ser Ser
            100                 105                 110
Asn Arg Arg Asp Arg Pro Arg Gln Pro Asn Pro Ser Gln Ser Ser Asp
        115                 120                 125
Ser Gln Val His Ser Gly Val Gln Val Glu Gly Arg Arg Gly Gln Ser
    130                 135                 140
Ser Ser Ala Asn Arg Arg Ala Gly Ser Ser Ser Gly Ser Gly Val Gln
145                 150                 155                 160
```

Gly Ala Ser Ala Gly Gly Leu Ala Ala Asp Ala Ser Arg Arg Ser Gly
                165                 170                 175

Ala Arg Gln Gly Gln Ala Ser Ala Gln Gly Arg Ala Gly Ser Gln Gly
            180                 185                 190

Gln Ala Gln Gly Arg Val Gly Ser Ala Asp Arg Gln Gly Arg Arg
        195                 200                 205

Gly Val Ser Glu Ser Gln Ala Ser Asp Ser Glu Gly His Ser Asp Phe
    210                 215                 220

Ser Glu Gly Gln Ala Val Gly Ala His Arg Gln Ser Gly Ala Gly Gln
225                 230                 235                 240

Arg His Glu Gln Arg Ser Ser Arg Gly Gln His Gly Ser Gly Tyr Tyr
                245                 250                 255

Tyr Glu Gln Glu His Ser Glu Glu Glu Ser Asp Ser Gln Arg Met Arg
            260                 265                 270

Arg Met Arg Arg Met Arg Arg
        275

<210> SEQ ID NO 23
<211> LENGTH: 10
<212> TYPE: PRT
<213> ORGANISM: Artificial Sequence
<220> FEATURE:
<223> OTHER INFORMATION: Synthetic peptide

<400> SEQUENCE: 23

Arg Met Arg Arg Met Arg Arg Met Arg Arg
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Synthetic peptide

<400> SEQUENCE: 24

Arg Gly Arg Arg Gly Arg Arg Gly Arg Arg
1               5                   10

<210> SEQ ID NO 25
<211> LENGTH: 10
<212> TYPE: PRT
<213> ORGANISM: Artificial Sequence
<220> FEATURE:
<223> OTHER INFORMATION: Synthetic peptide

<400> SEQUENCE: 25

Arg Arg Arg Arg Arg Arg Arg Arg Arg Arg
1               5                   10

<210> SEQ ID NO 26
<211> LENGTH: 10
<212> TYPE: PRT
<213> ORGANISM: Artificial Sequence
<220> FEATURE:
<223> OTHER INFORMATION: Synthetic peptide

<400> SEQUENCE: 26

Arg Ala Arg Arg Ala Arg Arg Ala Arg Arg
1               5                   10

```
<210> SEQ ID NO 27
<211> LENGTH: 10
<212> TYPE: PRT
<213> ORGANISM: Artificial Sequence
<220> FEATURE:
<223> OTHER INFORMATION: Synthetic peptide

<400> SEQUENCE: 27

Arg Thr Arg Arg Thr Arg Arg Thr Arg Arg
1               5                   10

<210> SEQ ID NO 28
<211> LENGTH: 10
<212> TYPE: PRT
<213> ORGANISM: Artificial Sequence
<220> FEATURE:
<223> OTHER INFORMATION: Synthetic peptide

<400> SEQUENCE: 28

Arg Ser Arg Arg Ser Arg Arg Ser Arg Arg
1               5                   10

<210> SEQ ID NO 29
<211> LENGTH: 10
<212> TYPE: PRT
<213> ORGANISM: Artificial Sequence
<220> FEATURE:
<223> OTHER INFORMATION: Synthetic peptide

<400> SEQUENCE: 29

Arg Val Arg Arg Val Arg Arg Val Arg Arg
1               5                   10

<210> SEQ ID NO 30
<211> LENGTH: 10
<212> TYPE: PRT
<213> ORGANISM: Artificial Sequence
<220> FEATURE:
<223> OTHER INFORMATION: Synthetic peptide

<400> SEQUENCE: 30

Arg Lys Arg Arg Lys Arg Arg Lys Arg Arg
1               5                   10

<210> SEQ ID NO 31
<211> LENGTH: 7
<212> TYPE: PRT
<213> ORGANISM: Artificial Sequence
<220> FEATURE:
<223> OTHER INFORMATION: Synthetic peptide

<400> SEQUENCE: 31

Arg Arg Arg Arg Arg Arg Arg
1               5

<210> SEQ ID NO 32
<211> LENGTH: 8
<212> TYPE: PRT
<213> ORGANISM: Artificial Sequence
<220> FEATURE:
<223> OTHER INFORMATION: Synthetic peptide

<400> SEQUENCE: 32

Arg Arg Arg Arg Arg Arg Arg Arg
1               5
```

```
<210> SEQ ID NO 33
<211> LENGTH: 9
<212> TYPE: PRT
<213> ORGANISM: Artificial Sequence
<220> FEATURE:
<223> OTHER INFORMATION: Synthetic peptide

<400> SEQUENCE: 33

Arg Arg Arg Arg Arg Arg Arg Arg Arg
1               5

<210> SEQ ID NO 34
<211> LENGTH: 11
<212> TYPE: PRT
<213> ORGANISM: Artificial Sequence
<220> FEATURE:
<223> OTHER INFORMATION: Synthetic peptide

<400> SEQUENCE: 34

Arg Arg Arg Arg Arg Arg Arg Arg Arg Arg Arg
1               5                   10

<210> SEQ ID NO 35
<211> LENGTH: 12
<212> TYPE: PRT
<213> ORGANISM: Artificial Sequence
<220> FEATURE:
<223> OTHER INFORMATION: Synthetic peptide

<400> SEQUENCE: 35

Arg Arg Arg Arg Arg Arg Arg Arg Arg Arg Arg Arg
1               5                   10

<210> SEQ ID NO 36
<211> LENGTH: 13
<212> TYPE: PRT
<213> ORGANISM: Artificial Sequence
<220> FEATURE:
<223> OTHER INFORMATION: Synthetic peptide

<400> SEQUENCE: 36

Arg Arg Arg Arg Arg Arg Arg Arg Arg Arg Arg Arg Arg
1               5                   10

<210> SEQ ID NO 37
<211> LENGTH: 14
<212> TYPE: PRT
<213> ORGANISM: Artificial Sequence
<220> FEATURE:
<223> OTHER INFORMATION: Synthetic peptide

<400> SEQUENCE: 37

Arg Arg Arg Arg Arg Arg Arg Arg Arg Arg Arg Arg Arg Arg
1               5                   10

<210> SEQ ID NO 38
<211> LENGTH: 15
<212> TYPE: PRT
<213> ORGANISM: Artificial Sequence
<220> FEATURE:
<223> OTHER INFORMATION: Synthetic peptide

<400> SEQUENCE: 38

Arg Arg Arg Arg Arg Arg Arg Arg Arg Arg Arg Arg Arg Arg Arg
1               5                   10                  15
```

```
<210> SEQ ID NO 39
<211> LENGTH: 5
<212> TYPE: PRT
<213> ORGANISM: Artificial Sequence
<220> FEATURE:
<223> OTHER INFORMATION: Synthetic peptide

<400> SEQUENCE: 39

Gly Gly Gly Gly Ser
1               5

<210> SEQ ID NO 40
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 40

Glu Gly Lys Ser Ser Gly Ser Gly Ser Glu Ser Lys Val Asp
1               5                  10

<210> SEQ ID NO 41
<211> LENGTH: 18
<212> TYPE: PRT
<213> ORGANISM: Artificial Sequence
<220> FEATURE:
<223> OTHER INFORMATION: Synthetic peptide

<400> SEQUENCE: 41

Lys Glu Ser Gly Ser Val Ser Ser Glu Gln Leu Ala Gln Phe Arg Ser
1               5                  10                  15

Leu Asp
```